(12) United States Patent
Villegas et al.

(10) Patent No.: US 7,776,558 B2
(45) Date of Patent: Aug. 17, 2010

(54) HUMAN G PROTEIN-COUPLED RECEPTOR AND MODULATORS THEREOF FOR THE TREATMENT OF CELL DEATH-RELATED DISORDERS

(75) Inventors: Sonia Villegas, San Diego, CA (US); Gregory S. Kelner, San Diego, CA (US); David J. Unett, San Diego, CA (US); Joel Gatlin, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 487 days.

(21) Appl. No.: 10/549,228

(22) PCT Filed: Mar. 15, 2004

(86) PCT No.: PCT/US2004/008191

§ 371 (c)(1),
(2), (4) Date: Mar. 5, 2007

(87) PCT Pub. No.: WO2004/083867

PCT Pub. Date: Sep. 30, 2004

(65) Prior Publication Data

US 2008/0125491 A1    May 29, 2008

Related U.S. Application Data

(60) Provisional application No. 60/455,316, filed on Mar. 17, 2003, provisional application No. 60/532,001, filed on Dec. 22, 2003.

(51) Int. Cl.
*G01N 33/567* (2006.01)
*C07K 14/705* (2006.01)

(52) U.S. Cl. .................. 435/7.21; 435/7.1; 435/7.2; 436/501

(58) Field of Classification Search .................. None
See application file for complete search history.

(56) References Cited

FOREIGN PATENT DOCUMENTS

| EP | 1514930 A1 | 3/2005 |
|---|---|---|
| WO | WO 02/068600 A | 9/2002 |
| WO | WO 03/046205 A | 6/2003 |
| WO | WO 03/080098 A | 10/2003 |
| WO | WO 03/106683 A | 12/2003 |
| WO | WO 2004/008141 A | 1/2004 |

OTHER PUBLICATIONS

Hashimoto et al. Involvement of Tyrosine Kinases and STAT3 in Humanin-mediated neuroprotection, Oct. 28, 2005, Life Sciences vol. 77(24):3092-3104.*
Migeotte et al. Formyl Peptide Receptors: A Promiscuous Subfamily of G protein-coupled Receptors Controlling Immune Response, Dec. 2006, Cytokine & Growth Factor Reviews vol. 17(6):501-519.*
Betten A et al: "A proinflammatory peptide from *Heliobacter pylori* activates monocytes to induce lymphocyte dysfunction and apoptosis", J Clin Invest (2001) 108:1221-1228.
Christophe T et al: "The synthetic peptide Trp-Lys-Tyr-Met-Val-Met-NH2 specifically activates neutrophils through FPRL1/lipoxin A4 . . . ", J Biol Chem (2001) 276:21585-21593.
Hashimoto Y et al: "A rescue factor abolishing neuronal cell death by a wide spectrum of familial Alzheimer's disease genes . . . ", Proc Natl Acad Sci U S A (2001) 98:6336-6341.
Kariya A et al: "Humanin accelerates the transcription of . . . ", 32nd Annual Meeting of the Society for Neuroscience, Orlando, FL, Nov. 2-7, 2002, Abstract No. 786.2.
Ying GG et al: "Humanin, a newly identified neuroprotective factor, uses the G-protein coupled . . . ", J Interferon Cytokine Res (2002) 22(Suppl 1):S-180, Abstract No. P-17-10.
Ernst S et al: "An annexin 1 N-terminal peptide activates leukocytes by triggering different members of the formyl peptide receptor family", J Immunol (2004) 172:7669-7676.
Database WPI, Section Ch, Week 200411, Derwent Publications Ltd., London, GB; AN 2004-108321, XP002291796, (2004).
Database WPI, Section Ch, Week 200414, Derwent Publications Ltd., London, GB; AN 2004-143116, XP002291797, (2002).
Hashimoto Y et al: "Mechanisms of neuroprotection by a novel rescue factor humanin from Swedish mutant amyloid precursor . . . ", Biochem Biophys Res Commun (2001) 283:460-468.
Akal-Strader et al., Residues in the first extracellular loop of a G protein-coupled receptor play a role in signal transduction. J Biol Chem. 2002 277:30581-90.
Bai et al., "Structure and function of the extracellular calcium-sensing receptor," Int J Mol Med. 1999 4:115-25 (Review).
Califano, "SPLASH: structural pattern localization analysis by sequential histograms,"Bioinformatics. 2000 16:341-57.
Chollet et al., "Biophysical approaches to G protein-coupled receptors: structure, function and dynamics" J Comput Aided Mol Des. 1999 13:209-19 (Review).
Chung Da et al., "Mutagenesis and peptide analysis of the DRY motif in the alpha2A adrenergic receptor: evidence for alternate mechanisms in G protein-coupled receptor" Biochem Biophys Res Commun. 2002 293:1233-41.
Filizola et al., "BUNDLE: a program for building the transmembrane domains of G-protein-coupled receptors," J Comput Aided Mol Des. 1998 12:111-8.

(Continued)

*Primary Examiner*—John D Ulm
(74) *Attorney, Agent, or Firm*—James S. Keddie; Carol L. Francis; Bozicevic, Field & Francis LLP

(57) ABSTRACT

The present invention relates to methods of identifying whether a candidate compound is a modulator of a G protein-coupled receptor (GPCR). In certain embodiments, the GPCR is human. In certain embodiments, the GPCR is expressed endogenously by neuronal cells or muscle cells. In certain embodiments, the GPCR is neuroprotective or myoprotective. In certain embodiments, the GPCR is a Humanin receptor. The present invention also relates to methods of using a modulator of the GPCR. A preferred modulator is agonist. Agonists of the invention are useful as therapeutic agents for the prevention or treatment of neurodegenerative diseases in general, including Alzheimer's disease, Parkinson's disease, prion-associated disease, stroke and motor-neuron disease in particular, peripheral neuropathy, cerebral amyloid beta-protein angiopathy, and ischemic heart disease, including myocardial infarction and congestive heart failure.

15 Claims, 18 Drawing Sheets

OTHER PUBLICATIONS

Gimpl et al., "The oxytocin receptor system: structure, function, and regulation," Physiol Rev. 2001 81:629-83 (Review).

Gouldson et al., "Domain swapping in G-protein coupled receptor dimmers," Protein Eng. 1998 11:1181-93.

Gouldson et al., "Dimerization and domain swapping in G-protein-coupled receptors: a computational study," Neuropsychopharmacology. 2000 23:S60-77.

Hurley et al., "Structure-function studies of the eighth hydrophobic domain of a serotonin receptor" J Neurochem. 1999 72:413-21.

Krasnoperov et al., "Structural requirements for alpha-latrotoxin binding and alpha-latrotoxin-stimulated secretion. A study with calcium-independent receptor of alpha-latrotoxin (CIRL) deletion mutants" J Biol Chem. 1999 274:3590-6.

Missale et al., "Dopamine receptors: from structure to function," Physiol Rev. 1998 78:189-225 (Review).

Mouledous et al., "Functional inactivation of the nociceptin receptor by alanine substitution of glutamine 286 at the C terminus of transmembrane segment VI: evidence from a site-directed mutagenesis study of the ORL1 receptor transmembrane-binding domain" Mol Pharmacol. 2000 57:495-502.

Olah et al., "The role of receptor structure in determining adenosine receptor activity," Pharmacol Ther. 2000 85:55-75 (Review).

Orry et al., "Modeling and docking the endothelin G-protein-coupled receptor," Biophys J. 2000 79:3083-94.

Palczewski et al., "Crystal structure of rhodopsin: A G protein-coupled receptor", Science 2000 289:739-45.

Sealfon et al., Functional domains of the gonadotropin-releasing hormone receptor, Cell Mol Neurobiol. 1995 15:25-42 (Review).

Shin N et al., Molecular modeling and site-specific mutagenesis of the histamine-binding site of the histamine H4 receptor. Mol Pharmacol. 2002 62:38-47.

Ulloa-Aguirre et al., "Structure-activity relationships of G protein-coupled receptors" Arch Med Res. 1999 30:420-35 (Review).

Yang et al., "Molecular determinants of human melanocortin-4 receptor responsible for antagonist SHU9119 selective activity" J Biol Chem. 2002 277:20328-35.

* cited by examiner

A. FPRL2

Humanin

[Gly14]-Humanin

B. FPRL1

Humanin

[Gly14]-Humanin

C. FPR

[Gly14]-Humanin

Humanin

Humanin

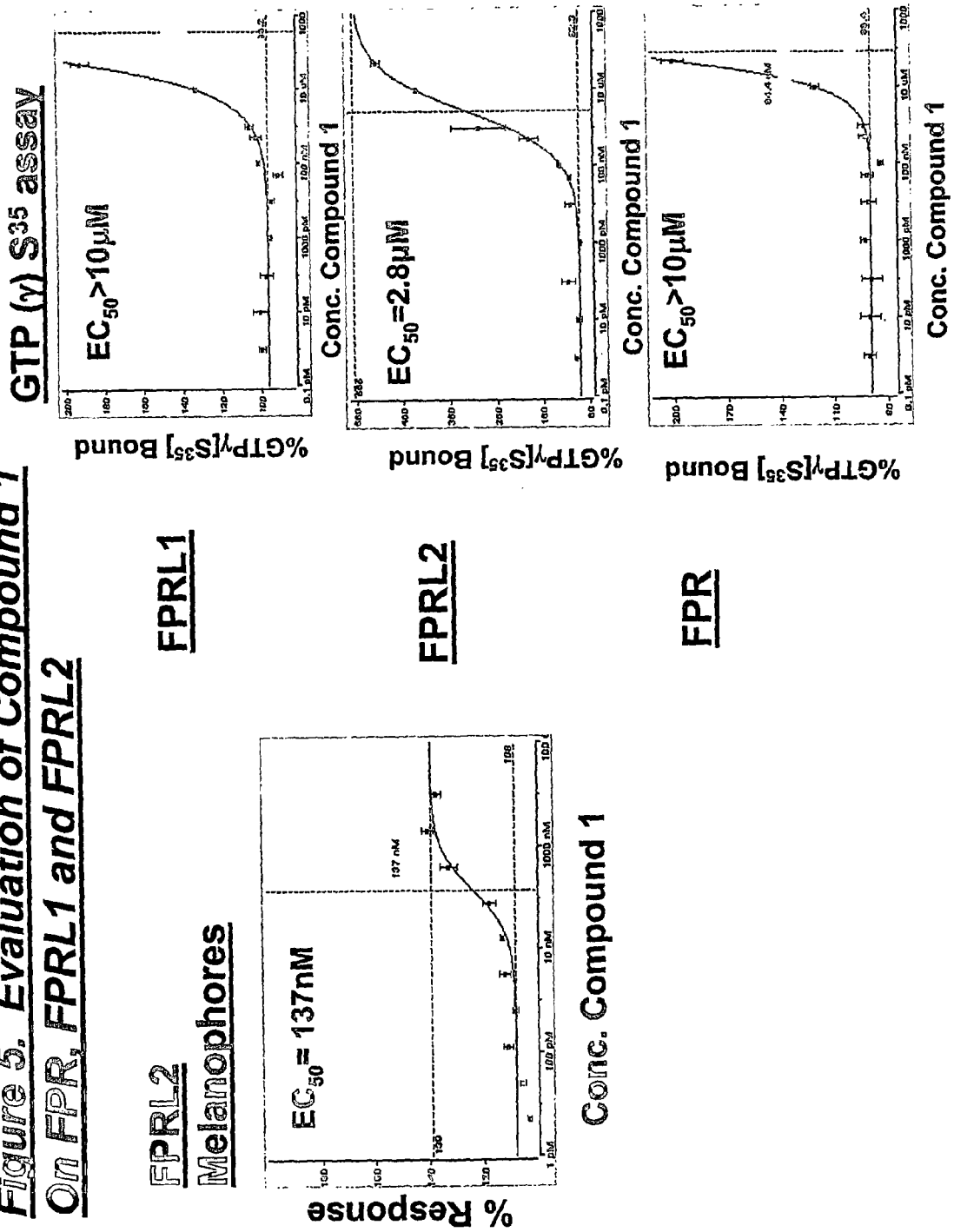
Figure 5. Evaluation of Compound 1 On FPR, FPRL1 and FPRL2

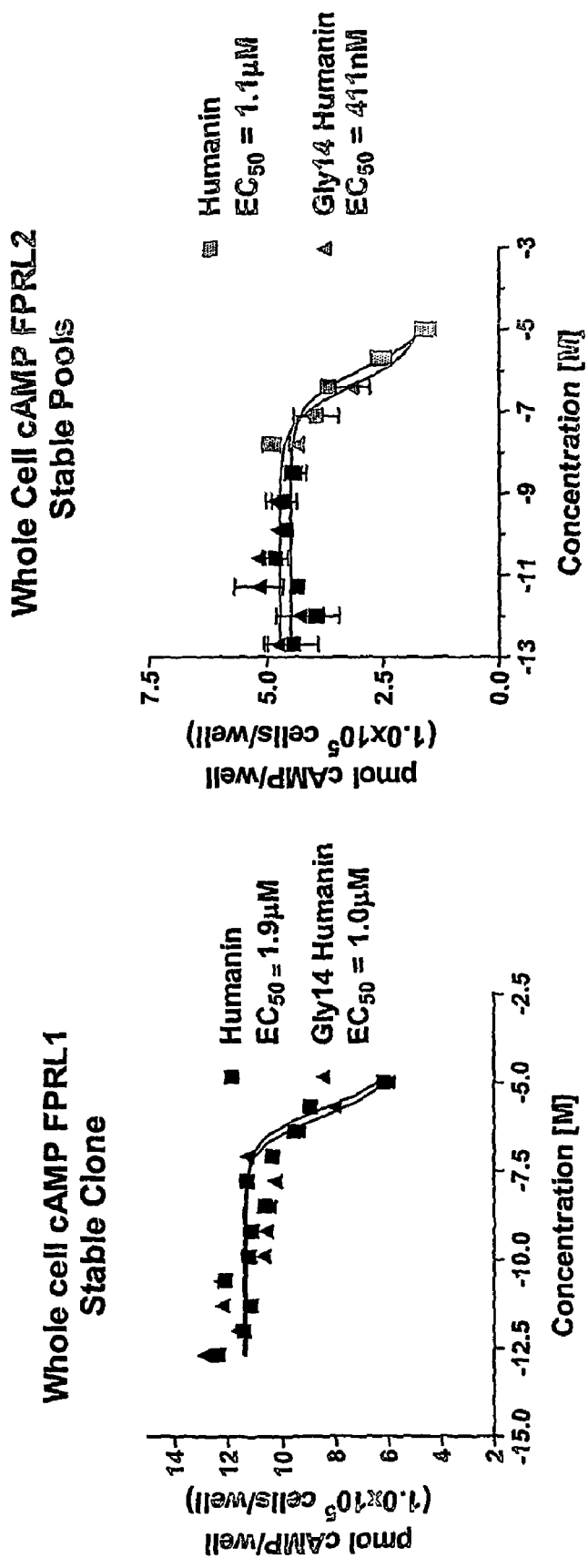
Figure 6A. Adenylate Cyclase Assays: FPRL1 & FPRL2 Humanin & [Gly14] Humanin Efficacy

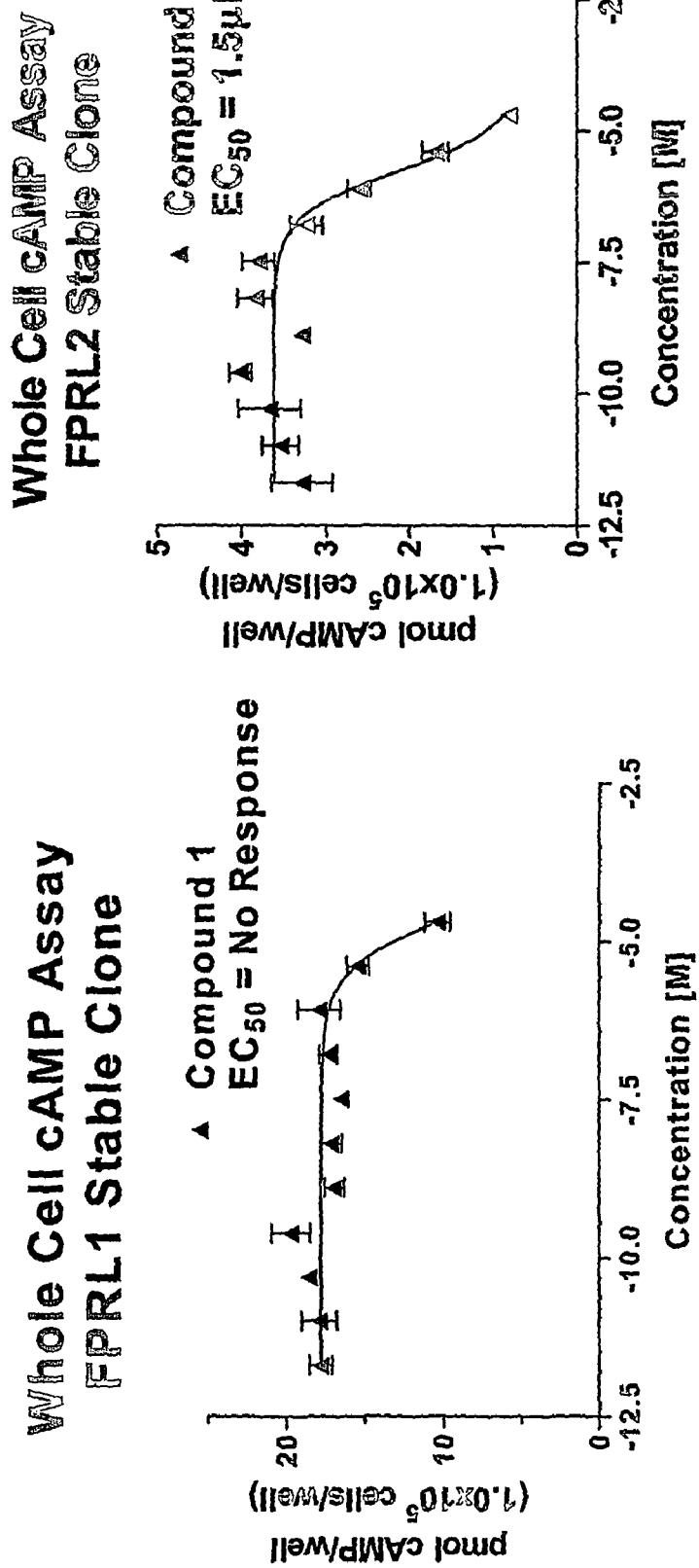
Figure 6B. Adenylate Cyclase Assays: Compound 1 Efficacy on FPRL1 & FPRL2

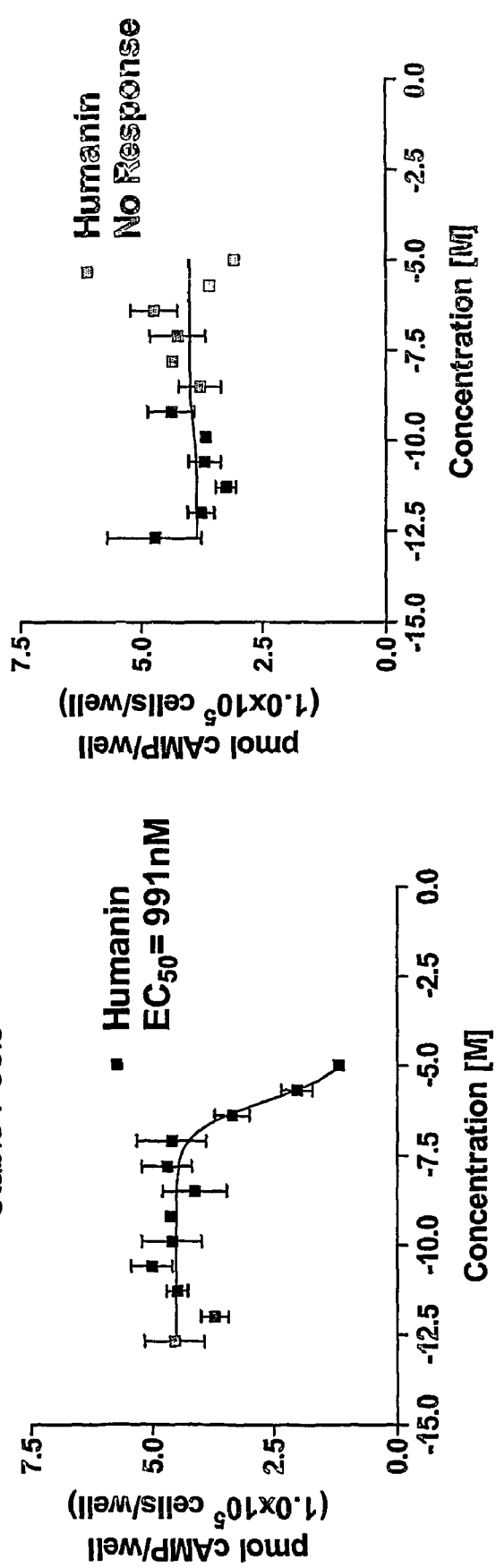
Figure 7A – Humanin signals via a Pertussis Toxin Sensitive mechanism on FPRL2

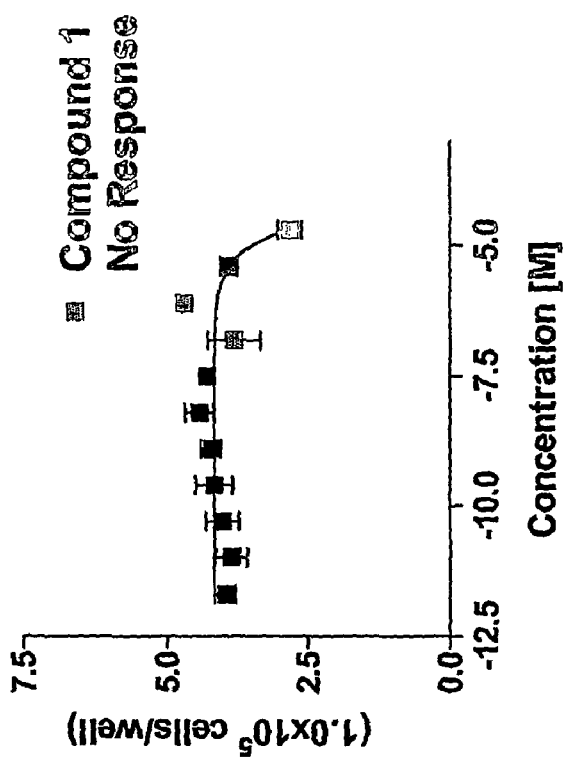
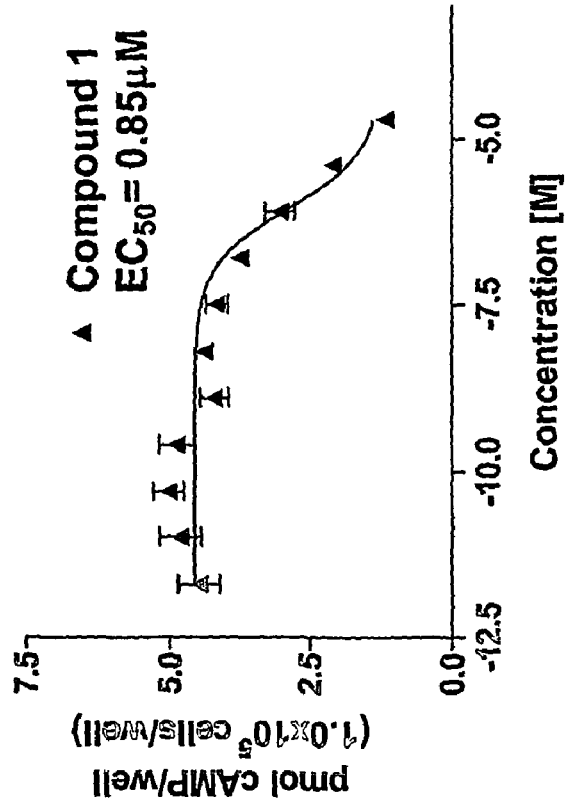
Fig. 7B – Compound 1 has similar effect as Humanin on FPRL2

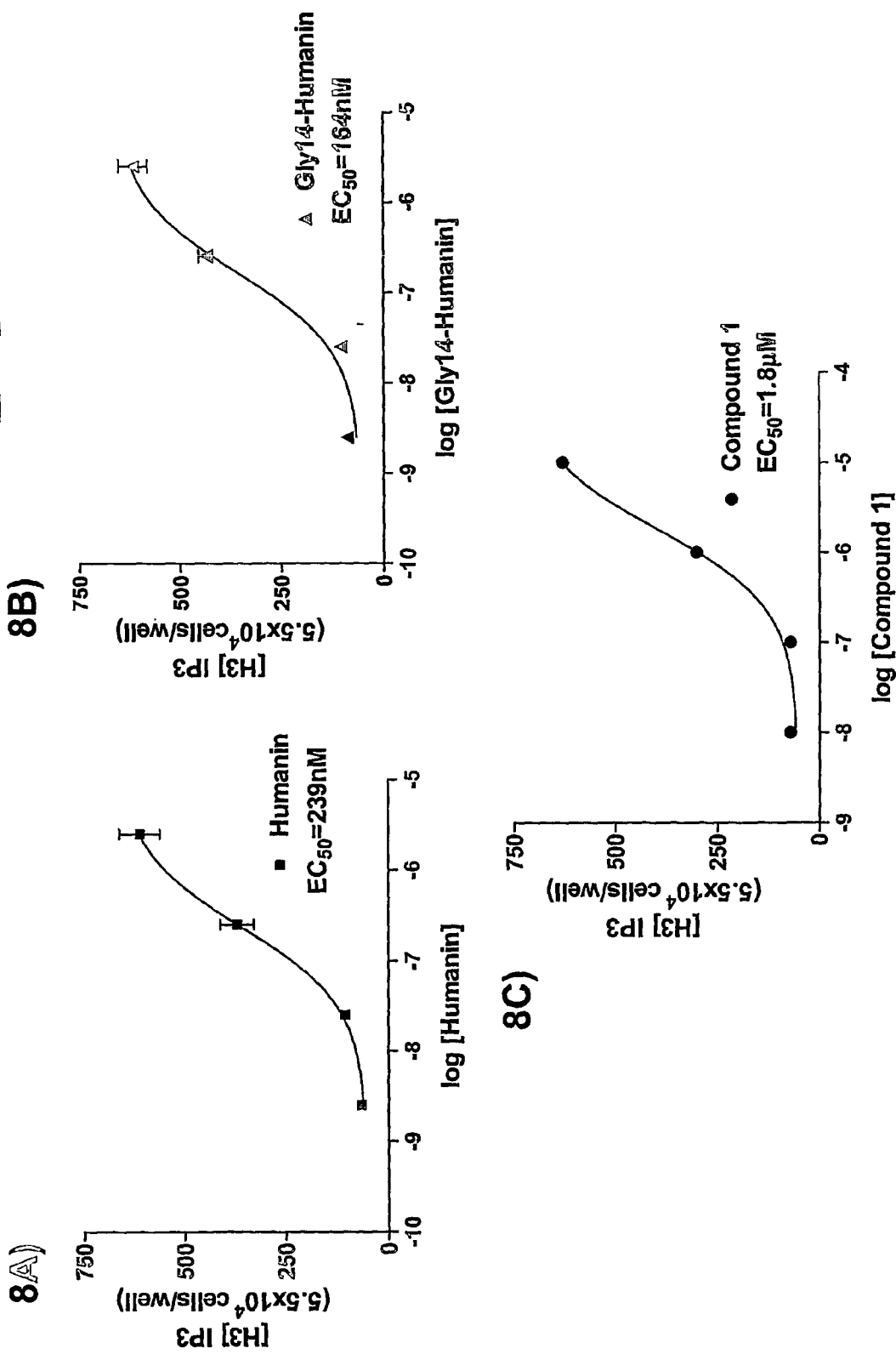
Fig. 8 A-C : FPRL2 signals through $G\alpha_{16}$ ($IP_3$)

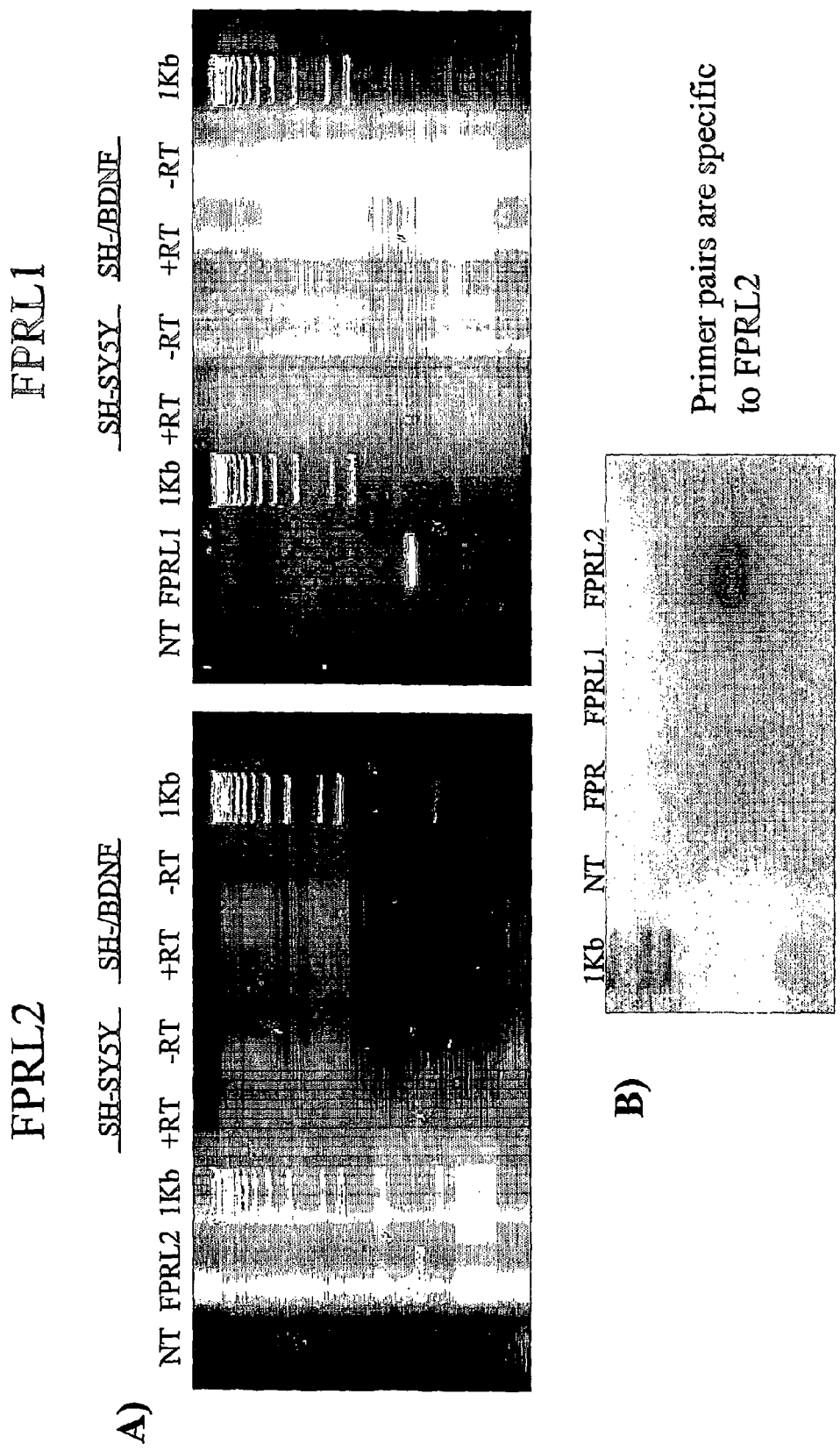
Figure 9. RT-PCR analysis of FPRL2 and FPRL1 expression in SH-SY5Y and SH-SY5Y/BDNF cDNA

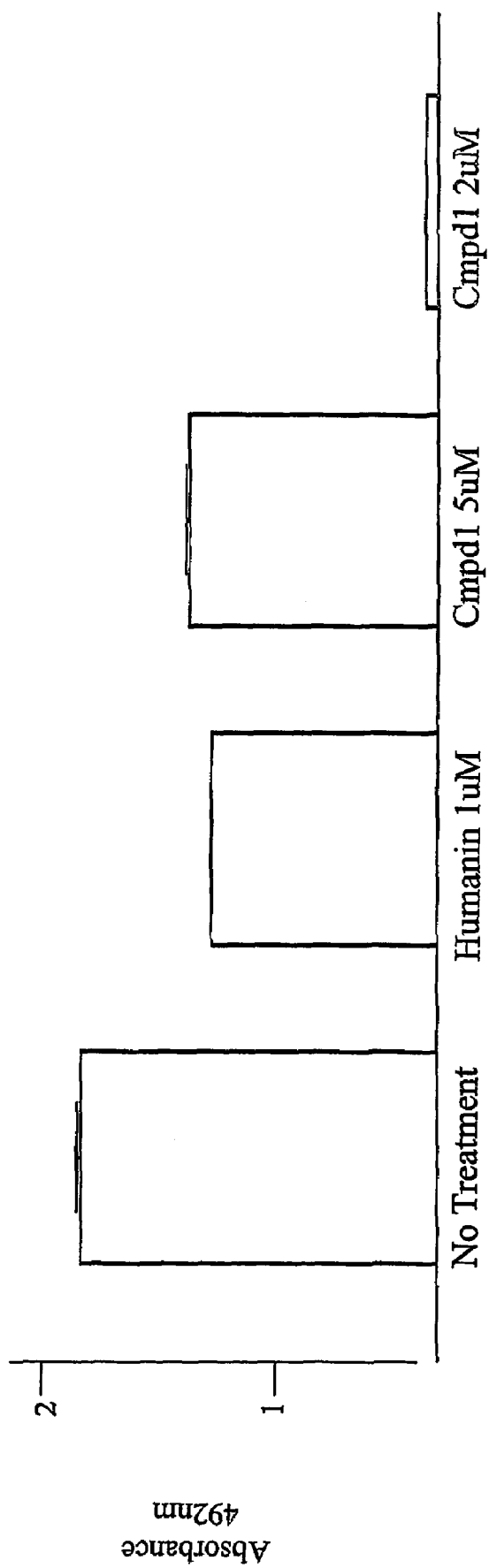
Figure 10A. LDH assay of 6 day serum deprived differentiated SH-SY5Y cells

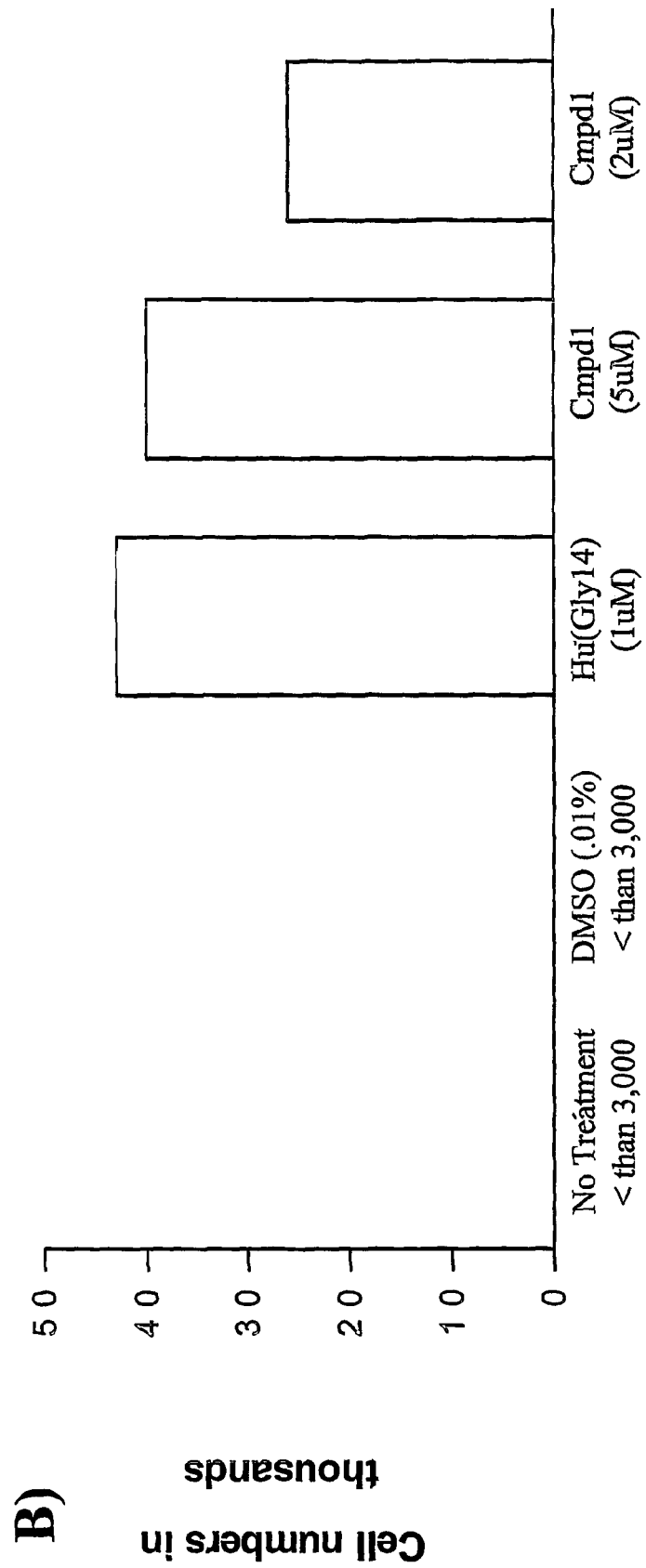
Figure 10B. Differentiated SH-SY5Y cell numbers after 6 days of serum withdrawal determined by Trypan Blue stain

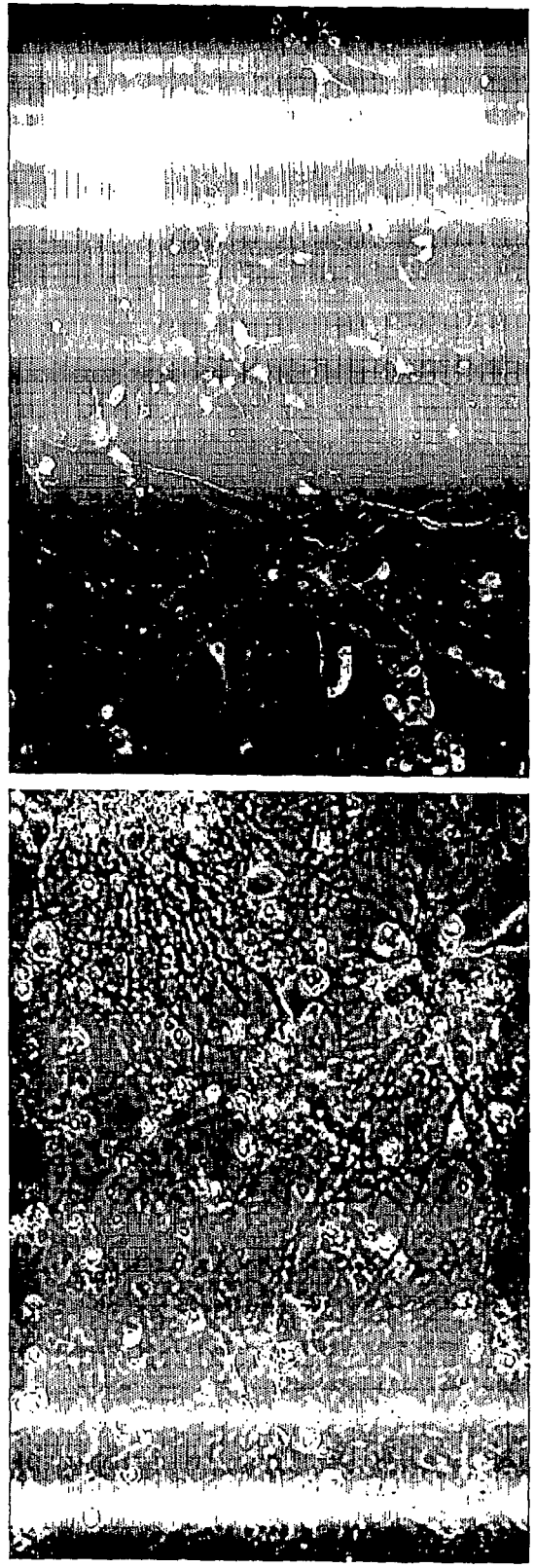
Figure 11A. Established primary culture of near pure mouse cortical neurons from E17 mouse embryos
A)

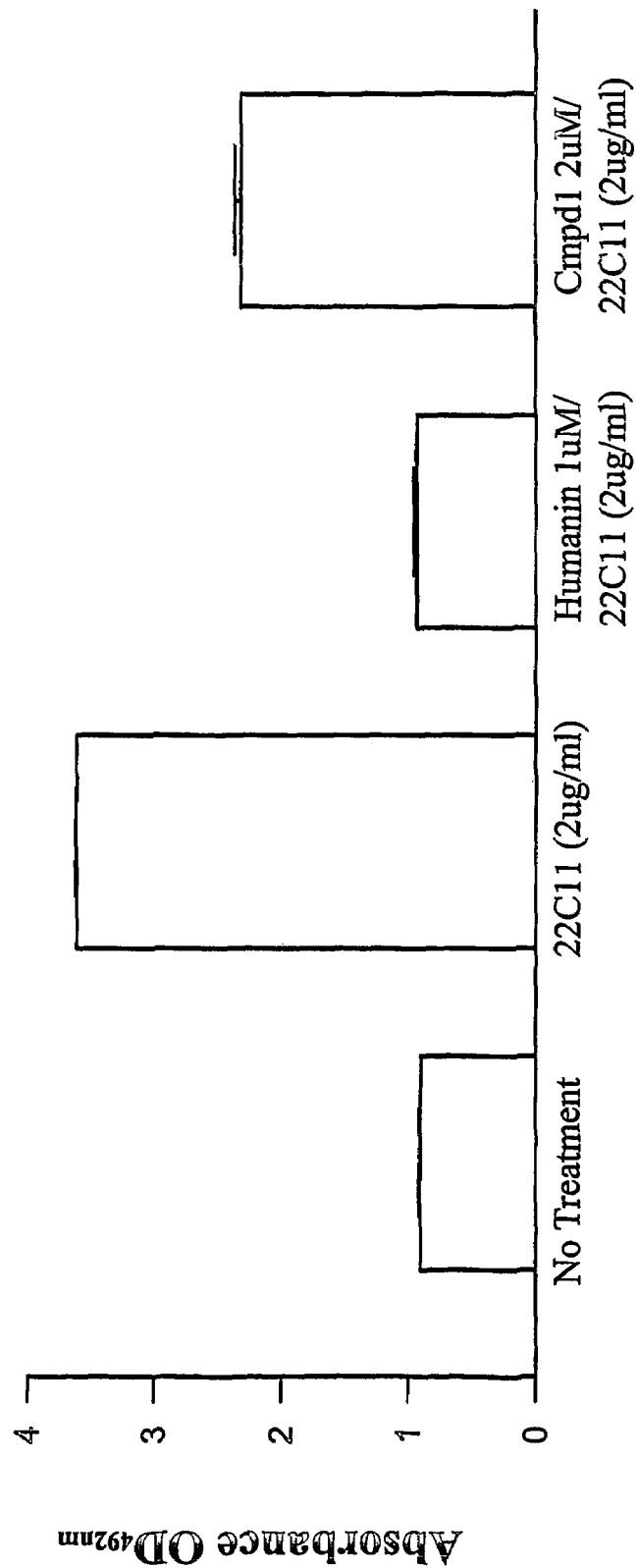
Figure 11B. Humanin and Compound 1 mediate protection of primary mouse cortical neurons against antibody 22C11 directed to β-amyloid precursor protein

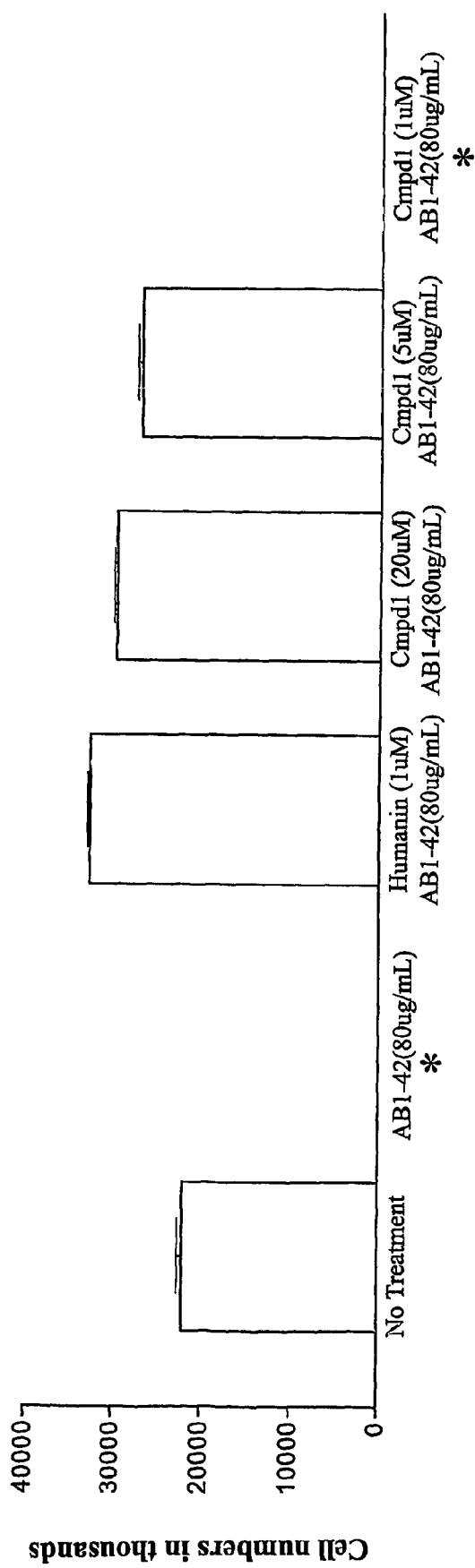
Figure 12. Humanin and Compound 1 mediate neuronal protection against A-beta in differentiated SH-SY5Y cells
* No cells were recovered from the AB1-42 chamber or the Cmpd1(1uM)/ AB1-42 chamber after treatment.

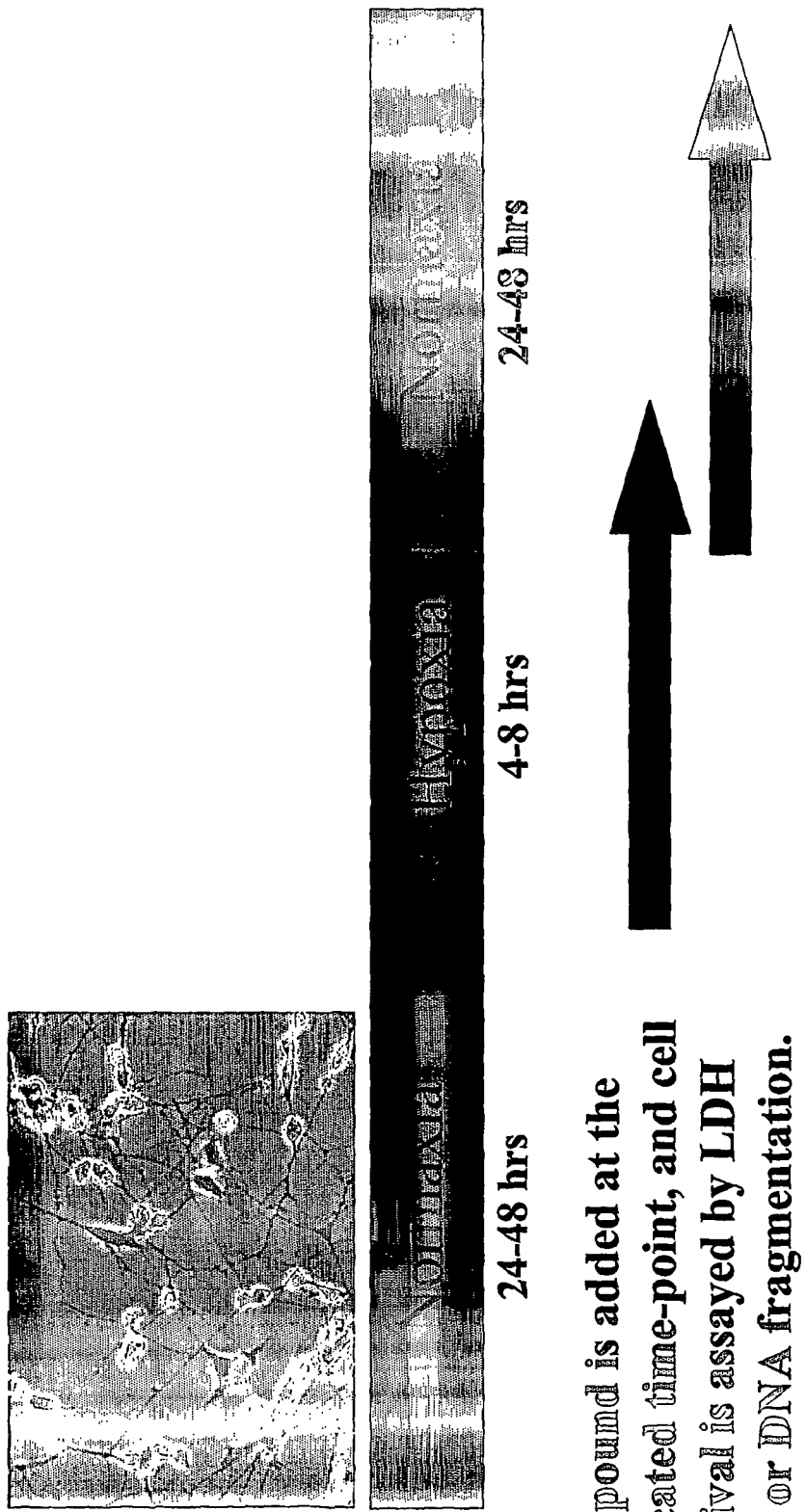
Figure 13. Neuroprotection by FPRL2 compounds of differentiated SH-SY5Y cells and mouse cortical neurons in an hypoxia/re-oxygenation *in-vitro* model
Compound is added at the indicated time-point, and cell survival is assayed by LDH level or DNA fragmentation.

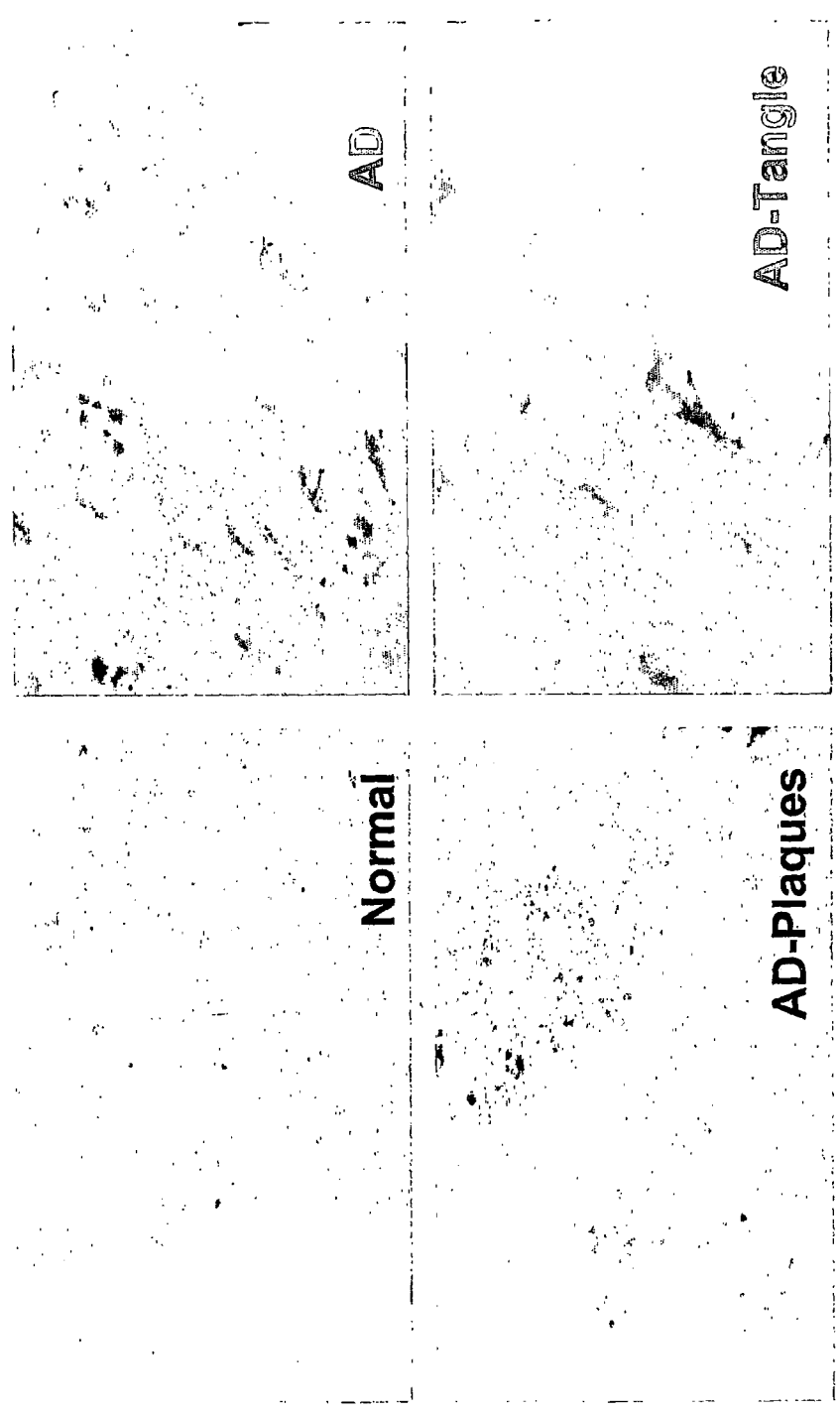
Figure 14. FPRL2 expression in human brain tissues

HUMAN G PROTEIN-COUPLED RECEPTOR AND MODULATORS THEREOF FOR THE TREATMENT OF CELL DEATH-RELATED DISORDERS

This application claims the benefit of priority from the following provisional applications, filed via U.S. Express mail with the United States Patent and Trademark Office on the indicated dates: U.S. Provisional No. 60/455,316, filed Mar. 17, 2003, and U.S. Provisional No. 60/532,001, filed Dec. 22, 2003. The disclosures of the foregoing applications are herein incorporated by reference in their entireties.

FIELD OF THE INVENTION

The present invention relates to methods of identifying whether a candidate compound is a modulator of a G protein-coupled receptor (GPCR). In certain embodiments, the GPCR is human. In certain embodiments, the GPCR is expressed endogenously by neuronal cells or muscle cells. In certain embodiments, the GPCR is neuroprotective or myoprotective. In certain embodiments, the GPCR is a Humanin receptor. The present invention also relates to methods of using a modulator of said GPCR. A preferred modulator is agonist. Agonists of the invention are useful as therapeutic agents for the prevention or treatment of neurodegenerative diseases in general, including Alzheimer's disease, Parkinson's disease, prion-associated disease, stroke and motor-neuron disease in particular, peripheral neuropathy, cerebral amyloid beta-protein angiopathy, and ischemic heart disease, including myocardial infarction and congestive heart failure.

BACKGROUND OF THE INVENTION

A. Cell Death-Related Disorders

The following discussion is intended to facilitate the understanding of the invention, but is not intended nor admitted to be prior art to the invention.

Anomalous cell death is a component of a number of pathologies, including neurodegenerative disease, cerebral amyloid beta-protein angiopathy (CAA), and some cardiomyopathies. Said anomalous cell death may comprise apoptotic cell death. Agents that are cell death-protective have utility for the prevention or treatment of said pathologies. In particular, agents that are neuroprotective or myoprotective have utility for the prevention or treatment of said neurodegenerative disease or said myopathy.

Alzheimer's disease is a progressive neurodegenerative disease characterized by significant loss of function in more than one cognitive domain and often accompanied by changes in behavior or personality (Alzheimer's Disease; Decision Resources, Inc.; November 2001). Mutations in three different genes can cause early-onset familial Alzheimer's disease (FAD): amyloid precursor protein (APP), presenilin 1 (PS1) and presenilin 2 (PS2). Early-onset familial Alzheimer's disease accounts for less than 5% of all Alzheimer's disease cases, however. More typically, Alzheimer's disease occurs in people aged 65 and older. Alzheimer's disease is the most common cause of dementia, affecting approximately 20 million people worldwide. Amyloid beta-peptide (Aβ) is believed to play a central role in the pathology of Alzheimer's disease.

Mild cognitive impairment (MCI) is a state of cognitive impairment, most often of memory only, that is not severe enough to significantly impact occupational or social functioning. However, many people with MCI progress to Alzheimer's disease, at a rate of 10-15% per year and up to 60% within five years. Growing evidence shows that Alzheimer's disease pathology begins much earlier than the development of symptoms severe enough to allow a diagnosis of Alzheimer's criteria. In 2001, the American Academy of Neurology (AAN) published clinical practice parameters for the detection of MCI that will increase awareness, diagnosis, and treatment of both MCI and mild forms of Alzheimer's disease.

Parkinson's disease is a chronic, progressive neurodegenerative disorder affecting more than 2.7 million people in the United States, Japan, and Western Europe. Parkinson's disease is characterized by motor symptoms such as tremor, bradykinesia, muscle rigidity, gait dysfunction, and postural instability. Although researchers have identified degeneration of dopaminergic neurons in the substantia nigra as the primary pathophysiological mechanism, they believe that other neurotransmitter systems—such as the serontonergic and glutamatergic systems—are also intricately involved in the disease process.

Prion-associated diseases include, but are not held to be limited to, bovine spongiform encephalopathy, Creutzfeldt-Jakob disease, kuru, Gerstmann-Straussler-Scheinker syndrome, and fatal familial insomnia [Collins et al., Lancet (2004) 3:51-61].

Stroke is an acute interruption of blood flow in the brain caused by blood vessel obstruction or hemorrhage. Almost 90% of all strokes are ischemic; that is, they are due to a reduction in cerebral circulation below a critical threshold. Stroke accounts for 10-12% of medically related deaths in industrialized countries and is the third leading cause of death worldwide. Overall estimates of the annual number of strokes in the United States range from 500,000 to 700,000.

Motor neuron disease is characterized by a selective degeneration of the motor neurons of the spinal cord, brainstem, or motor cortex. Clinical subtypes are distinguished by the major site of degeneration. In amyotrophic lateral sclerosis there is involvement of upper, lower, and brainstem motor neurons. In progressive spinal muscular atrophy and related syndromes the motor neurons in the spinal cord are primarily affected. With progressive bulbar palsy, the initial degeneration occurs in the brainstem. In primary lateral sclerosis, the cortical neurons are affected in isolation.

Peripheral neuropathy is a broad term used to describe a variety of disorders which manifest as painful or uncomfortable sensations usually in the extremities and are of neuropathic origin. Nerve degeneration is believed to play a role in peripheral neuropathy. This condition is found commonly amongst end stage renal disease and diabetic patients. Distal symmetrical polyneuropathy (DSP)—a neuropathy affecting both sides of the body and attacking the distal sensory nerves—is the most common clinical manifestation of diabetic neuropathy and accounts for approximately 80-85% of all neuropathy observed in diabetic patients. DSP affects 30-40% of patients with type 1 and type 2 diabetes. Diabetic neuropathy can typically damage many different nerves, including the sciatic nerve.

Cerebral amyloid beta-protein (Aβ) angiopathy (CAA) is a key feature of Alzheimer's disease and related disorders. CAA is a disease of small blood vessels in the brain in which deposits of amyloid protein in the vessel walls may lead to stroke, brain hemorrhage, or dementia. Vascular amyloid deposition leads to degeneration of the vessel wall and aneurysm formation, and may be responsible for 10 to 15% of hemorrhagic strokes in the elderly.

Myocardial infarction is the damage or death of an area of heart muscle because of an inadequate supply of oxygen to that area. Myocardial infarctions are often caused by a clot that blocks one of the coronary arteries (the blood vessels that bring blood and oxygen to heart muscle). The clot prevents blood and oxygen from reaching that area of the heart, leading to the death of cardiomyocytes in that area.

Congestive heart failure affects nearly 5 million Americans with over 500,000 new cases diagnosed annually. Ischemic heart disease is the most common cause of congestive heart failure, accounting for 60-70% of all cases. By definition, congestive heart failure is a clinical syndrome in which heart disease reduces cardiac output, increases venous pressures, and is accompanied by molecular abnormalities that cause progressive deterioration of the failing heart and premature cardiomyocyte (cardiac muscle cell) death. Any definition of heart failure that does not consider the molecular processes that accelerate myocardial death overlooks a major clinical feature of this syndrome. Evidence in mice and rats demonstrate that inhibitors of cardiomyocyte death pathways significantly improve cardiac function and animal survival [Laugwitz et al., Hum Gene Ther (2001) 12:2051-63].

B. Humanin

The following discussion is intended to facilitate the understanding of the invention, but is not intended nor admitted to be prior art to the invention.

Humanin polypeptide was originally identified through its capacity to protect neuronal cells from Alzheimer's disease-relevant toxicity [Hashimoto et al., Biochem Biophys Res Commun (2001) 283:460-8]. Humanin has the amino acid sequence: Met-Ala-Pro-Arg-Gly-Phe-Ser-Cys-Leu-Leu-Leu-Leu-Thr-Ser-Glu-Ile-Asp-Leu-Pro-Val-Lys-Arg-Arg-Ala (SEQ ID NO. 15) (GenBank® Accession No. AAK50430). An analog of Humanin having a substitution of glycine for serine at amino acid position 14, [Gly14]-Humanin, has been reported to be significantly more active than Humanin [Niikura et al., J Neurosci Res (2002) 70:380-91]. Humanin immunoreactivity has been detected in an Alzheimer's disease brain, but little in normal human brains [Tajima et al., Neurosci Lett (2002) 324:227-31].

Humanin has been found to protect neuronal cells from a number of toxic insults. This includes neurotoxicity mediated by three mutant genes that cause FAD as well as by Aβ [Hashimoto et al., Proc Natl Acad Sci USA (2001) 98:6336-41; Niikura et al., J Neurosci Res (2002) 70:380-91]. Aβ neurotoxicity involves a c-Jun N-terminal kinase (JNK) pathway, and Humanin acts at a point downstream of JNK [Hashimoto et al., J Neurochem (2003) 84:864-77]. Humanin has also been reported to have protective activity for neurons against serum deprivation [Takahashi et al., Neuroreport (2002) 13:903-7]. The rat ortholog of Humanin has been reported to have protective activity for neurons against excitotoxic death [Caricasole et al., FASEB J (2002) 16:1331-3].

Humanin has also been shown to rescue cortical neurons from prion-peptide-induced apoptosis [Sponne et al., Mol Cell Neurosci (2004) 25:95-102].

Humanin has further been shown to improve learning and memory impairment in mice, thereby evidencing utility as a beneficial agent for the prevention or treatment of said learning or memory impairment [Mamiya & Ukai, Br J Pharmacol (2001) 134:1597-9].

Recently, Humanin has been shown to be protective for muscle cells. Humanin rescues human cerebrovascular smooth muscle cells from Aβ-induced toxicity.

Collectively, the foregoing indicates that Humanin and compounds evidencing Humanin activity are cell death-protective. Said cell death may comprise apoptotic cell death. In particular, Humanin and compounds evidencing Humanin activity protect neuronal cells and muscle cells from cell death and have utility for the prevention or treatment of neurodegenerative disease, cerebral amyloid angiopathy, and some cardiomyopathies.

C. G Protein-Coupled Receptors

The following discussion is intended to facilitate the understanding of the invention, but is not intended nor admitted to be prior art to the invention.

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

| | | |
|---|---|---|
| Claritin ® (allergies) | Prozac ® (depression) | Vasotec ® (hypertension) |
| Paxil ® (depression) | Zoloft ® (depression) | Zyprexa ®(psychotic disorder) |
| Cozaar ® (hypertension) | Imitrex ® (migraine) | Zantac ® (reflux) |
| Propulsid ® (reflux disease) | Risperdal ® (schizophrenia) | Serevent ® (asthma) |
| Pepcid ® (reflux) | Gaster ® (ulcers) | Atrovent ® (bronchospasm) |
| Effexor ® (depression) | Depakote ® (epilepsy) | Cardura ®(prostatic ypertrophy) |
| Allegra ® (allergies) | Lupron ® (prostate cancer) | Zoladex ® (prostate cancer) |
| Diprivan ® (anesthesia) | BuSpar ® (anxiety) | Ventolin ® (bronchospasm) |
| Hytrin ® (hypertension) | Wellbutrin ® (depression) | Zyrtec ® (rhinitis) |
| Plavix ® (MI/stroke) | Toprol-XL ® (hypertension) | Tenormin ® (angina) |
| Xalatan ® (glaucoma) | Singulair ® (asthma) | Diovan ® (hypertension) |
| Harnal ® (prostatic hyperplasia) | | |
| (Med Ad News 1999 Data). | | |

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

There are also promiscuous G proteins, which appear to couple several classes of GPCRs to the phospholipase C pathway, such as Gα15 or Gα16 [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24].

Gi-coupled GPCRs lower intracellular cAMP levels. A Gi-like G protein is a G protein that similarly leads to lower intracellular cAMP level. By this criterion, Go and Gz are Gi-like G proteins. The melanophore technology (see infra) is useful for identifying Gi-coupled GPCRs and also for identifying modulators of said Gi-coupled GPCRs.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

D. FPRL2

The following discussion is intended to facilitate the understanding of the invention, but is not intended nor admitted to be prior art to the invention.

FPRL2 (GenBank® Accession No. L14061) is a GPCR for which no endogenous ligand has yet been demonstrated. The synthetic peptide WKYMVm (SEQ ID NO: 16) recently has been shown to bind to FPRL2 on mature human dendritic cells and elicit an increase in intracellular $Ca^{2+}$ [Yang et al., J Leukoc Biol (2002) 72:598-607].

FPRL2 is most similar to the GPCRs FPRL1 (GenBank® Accession No. AF054013) and FPR (GenBank® Accession No. M60627). Recently, it was reported that Humanin uses FPRL1 as a functional receptor [Ying et al., Journal of Interferon and Cytokine Research (2002) 22 (Supplement 1):S180]. No endogenous ligand for FPRL1 or FPR has been shown to also be a ligand for FPRL2 and, in fact, a number of endogenous ligands for FPRL1 or FPR (lipoxin A4, e.g.) have been shown not to be ligands for FPRL2.

SUMMARY OF THE INVENTION

Applicants have unexpectedly identified Humanin as a selective agonist of FPRL2 and thus provide Humanin as a first endogenous ligand of FPRL2. Applicants have further unexpectedly identified FPRL2 as a receptor selectively engaged by Humanin.

The present invention is directed in part to methods of identifying whether a test compound is a modulator of a Humanin GPCR, wherein said Humanin GPCR is FPRL2. The invention also encompasses modulators identified by said methods as well as methods of using said modulators for the prevention or treatment of cell death-related disorders, in particular disorders related to the death of neuronal cells or muscle cells.

In a first aspect, the invention features a method of identifying whether a candidate compound is a modulator of a Humanin GPCR, said receptor comprising an FPRL2 amino acid sequence, wherein the receptor couples to a G protein; comprising the steps of:

(a) contacting the candidate compound with the receptor;

(b) determining whether the receptor functionality is modulated;

wherein a change in receptor functionality is indicative of the candidate compound being a modulator of a Humanin GPCR.

In certain embodiments, said Humanin GPCR is recombinant. In certain embodiments, said contacting comprises contacting with a host cell or with membrane of a host cell that expresses the GPCR, wherein said host cell comprises an expression vector comprising a polynucleotide encoding the receptor.

In some embodiments, said contacting is carried out in the presence of a known ligand of the GPCR. In some embodiments, said known ligand is an agonist of the GPCR. In some embodiments, said agonist is Humanin or a peptide analog or derivative thereof. In some embodiments, said analog is [Gly14]-Humanin. In certain embodiments, said presence of said Humanin or said [Gly14]-Humanin is at about EC50 to about EC75 for the means of said determining. By way of example and not limitation, EC50 is about 0.32 µM and EC75 is about 1.5 µM for Humanin in [$^{35}$S]GTPγS binding assay. Humanin and [Gly14]-Humanin are commercially available (Peptides International, Louisville, Ky.). In some embodiments, said agonist is Compound 1 ("Cmpd 1" in Table 1). In certain embodiments, said presence of said Compound 1 is at about EC50 to about EC75 for the means of said determining. By way of example and not limitation, EC50 is about 2.8 µM and EC75 is about 15 µM for Compound 1 in [$^{35}$S]GTPγS binding assay.

The invention also relates to a method of identifying whether a candidate compound is a modulator of a cell death-protective GPCR, comprising the steps of:

(a) contacting the candidate compound with a GPCR comprising an FPRL2 amino acid sequence, wherein the receptor couples to a G protein; and (b) determining whether the receptor functionality is modulated;

wherein a change in receptor functionality is indicative of the candidate compound being a modulator of a cell death-protective GPCR.

In certain embodiments, said GPCR is recombinant. In certain embodiments, said contacting comprises contacting with a host cell or with membrane of a host cell that expresses the GPCR, wherein said host cell comprises an expression vector comprising a polynucleotide encoding the receptor.

In certain embodiments, said cell is neuronal and said GPCR is neuroprotective. In certain embodiments, said cell is muscle and said GPCR is myoprotective. In some embodiments, said cell is non-neuronal and non-muscle. In certain embodiments, said cell expresses human FPRL2.

In some embodiments, said cell death comprises apoptotic cell death. In some embodiments, said cell death comprises cell death that is Aβ-induced. In some embodiments, said cell death comprises cell death that is JNK activation-dependent. In some embodiments, said cell death comprises cell death induced by deprivation of a serum component. In some embodiments, said cell death comprises excitotoxic cell death.

In some embodiments, said contacting is carried out in the presence of a known ligand of the GPCR. In some embodiments, said known ligand is an agonist of the GPCR. In some embodiments, said agonist is Humanin or a peptide analog or derivative thereof. In some embodiments, said analog is [Gly14]-Humanin. In certain embodiments, said presence of said Humanin or said [Gly14]-Humanin is at about EC50 to about EC75 for the means of said determining. By way of example and not limitation, EC50 is about 0.32 µM and EC75 is about 1.5 µM for Humanin in [$^{35}$S]GTPγS binding assay. Humanin and [Gly14]-Humanin are commercially available (Peptides International, Louisville, Ky.). In some embodiments, said agonist is Compound 1. In certain embodiments, said presence of said Compound 1 is at about EC50 to about EC75 for the means of said determining. By way of example and not limitation, EC50 is about 2.8 µM and EC75 is about 15 µM for Compound 1 in [$^{35}$S]GTPγS binding assay.

The invention also relates to a method of identifying whether a candidate compound is a modulator of neuroprotection, comprising the steps of:
 (a) contacting the candidate compound with a GPCR comprising an FPRL2 amino acid sequence, wherein the receptor couples to a G protein; and
 (b) determining whether the receptor functionality is modulated;

wherein a change in receptor functionality is indicative of the candidate compound being a modulator of neuroprotection.

In certain embodiments, said GPCR is recombinant. In certain embodiments, said contacting comprises contacting with a host cell or with membrane of a host cell that expresses the GPCR, wherein said host cell comprises an expression vector comprising a polynucleotide encoding the receptor.

In certain embodiments, an increase in receptor functionality is indicative of the candidate compound being a neuroprotective compound.

In some embodiments, said contacting is carried out in the presence of a known ligand of the GPCR. In some embodiments, said known ligand is an agonist of the GPCR. In some embodiments, said agonist is Humanin or a peptide analog or derivative thereof. In some embodiments, said analog is [Gly14]-Humanin. In certain embodiments, said presence of said Humanin or said [Gly14]-Humanin is at about EC50 to about EC75 for the means of said determining. By way of example and not limitation, EC50 is about 0.32 µM and EC75 is about 1.5 µM for Humanin in [$^{35}$S]GTPγS binding assay. Humanin and [Gly14]-Humanin are commercially available (Peptides International, Louisville, Ky.). In some embodiments, said agonist is Compound 1. In certain embodiments, said presence of said Compound 1 is at about EC50 to about EC75 for the means of said determining. By way of example and not limitation, EC50 is about 2.8 µM and EC75 is about 15 µM for Compound 1 in [$^{35}$S]GTPγS binding assay.

The invention also relates to a method of identifying whether a candidate compound is a modulator of myoprotection, comprising the steps of:
 (a) contacting the candidate compound with a GPCR comprising an FPRL2 amino acid sequence, wherein the receptor couples to a G protein; and
 (b) determining whether the receptor functionality is modulated;

wherein a change in receptor functionality is indicative of the candidate compound being a modulator of myoprotection.

In certain embodiments, said GPCR is recombinant. In certain embodiments, said contacting comprises contacting with a host cell or with membrane of a host cell that expresses the GPCR, wherein said host cell comprises an expression vector comprising a polynucleotide encoding the receptor.

In certain embodiments, an increase in receptor functionality is indicative of the candidate compound being a myoprotective compound.

In some embodiments, said contacting is carried out in the presence of a known ligand of the GPCR. In some embodiments, said known ligand is an agonist of the GPCR. In some embodiments, said agonist is Humanin or a peptide analog or derivative thereof. In some embodiments, said analog is [Gly14]-Humanin. In certain embodiments, said presence of said Humanin or said [Gly14]-Humanin is at about EC50 to about EC75 for the means of said determining. By way of example and not limitation, EC50 is about 0.32 µM and EC75 is about 1.5 µM for Humanin in [$^{35}$S]GTPγS binding assay. Humanin and [Gly14]-Humanin are commercially available (Peptides International, Louisville, Ky.). In some embodiments, said agonist is Compound 1. In certain embodiments, said presence of said Compound 1 is at about EC50 to about EC75 for the means of said determining. By way of example and not limitation, EC50 is about 2.8 µM and EC75 is about 15 µM for Compound 1 in [$^{35}$S]GTPγS binding assay.

The invention also relates to a method of identifying whether a candidate compound is a modulator of a Humanin GPCR, comprising the steps of:
 (a) culturing Humanin GPCR-expressing host cells under conditions that would allow expression of a recombinant Humanin GPCR, said host cells being transfected with an expression vector comprising a polynucleotide encoding said recombinant Humanin GPCR comprising an FPRL2 amino acid sequence, wherein the receptor couples to a G protein;
 (b) contacting the Humanin GPCR-expressing host cells of step (a) or membrane of said host cells of step (a) with the candidate compound;
 (c) contacting control host cells or membrane of said control host cells with the candidate compound of step (b), wherein said control host cells do not express recombinant Humanin GPCR protein;
 (d) measuring the modulating effect of the candidate compound which interacts with the recombinant Humanin GPCR from the host cells of step (a) and control host cells of step (c); and
 (e) comparing the modulating effect of the test compound on the host cells and control host cells.

In certain embodiments, said transfected host cells are transiently transfected. In certain embodiments, said host cells are stably transfected.

The invention also relates to a method of identifying whether a candidate compound is a modulator of a Humanin GPCR, comprising the steps of:
(a) culturing Humanin GPCR-expressing host cells under conditions that would allow expression of a recombinant Humanin GPCR, said host cells being transfected with an expression vector comprising a polynucleotide encoding said recombinant Humanin GPCR comprising an FPRL2 amino acid sequence, wherein the receptor couples to a G protein;
(b) contacting a first population of Humanin GPCR-expressing cells of step (a) or membrane of said first population of Humanin GPCR-expressing cells of step (a) with a known ligand of said Humanin GPCR;
(c) contacting a second population of Humanin GPCR-expressing cells of step (a) or membrane of said second population of Humanin GPCR-expressing cells of step (a) with the candidate compound and with the known Humanin GPCR ligand;
(d) contacting control host cells or membrane of said control host cells with the candidate compound of step (c), wherein said control host cells do not express recombinant Humanin GPCR protein;
(e) measuring the modulating effect of the candidate compound, which interacts with recombinant Humanin GPCR, in the presence and absence of the known Humanin GPCR ligand, from the cells of step (b), step (c) and step (d); and
(f) comparing the modulating effect of the candidate compound as determined from step (b), step (c) and step (d).

In some embodiments, said ligand is an agonist of said Humanin GPCR. In some embodiments, said agonist is Humanin or a peptide analog or derivative thereof. In some embodiments, said analog is [Gly14]-Humanin. In certain embodiments, said presence of said Humanin or said [Gly14]-Humanin is at about 0.1 µM to 1.5 µM, more preferably at about 0.5 µM to 1 µM. In certain embodiments, said presence of said agonist is at EC50-EC75 for the means of said determining. By way of example and not limitation, EC50 is about 0.3 µM and EC75 is about 1.5 µM for Humanin in [$^{35}$S]GTPγS binding assay. In some embodiments, said agonist is Compound 1. In certain embodiments, said presence of said Compound 1 is at about EC50 to about EC75 for the means of said determining. By way of example and not limitation, EC50 is about 2.8 µM and EC75 is about 15 µM for Compound 1 in [$^{35}$S]GTPγS binding assay.

In certain embodiments, said transfected host cells are transiently transfected. In certain embodiments, said host cells are stably transfected.

The invention also relates to a method of identifying whether a candidate compound is a modulator of a Humanin GPCR, comprising the steps of:
(a) culturing Humanin GPCR-expressing host cells under conditions that would allow expression of a recombinant Humanin GPCR, said host cells being transfected with an expression vector comprising a polynucleotide encoding said recombinant Humanin GPCR comprising an FPRL2 amino acid sequence, wherein the receptor couples to a G protein;
(b) contacting a first population of the Humanin GPCR-expressing host cells of step (a) or membrane of said first population of the Humanin GPCR-expressing host cells of step (a) with the candidate compound;
(c) not contacting a second population of the Humanin GPCR-expressing cells of step (a) or membrane of said second population of the Humanin GPCR-expressing cells of step (a) with the candidate compound of step (b);
(d) contacting control host cells or membrane of said control host cells to the candidate compound of step (b), wherein said control host cells do not express recombinant Humanin GPCR protein;
(e) measuring the modulating effect of the candidate compound, which interacts with recombinant Humanin GPCR protein, from the cells of step (b) and step (c) and from the cells of step (d); and
(f) comparing the modulating effect of the candidate compound as determined from step (b) and step (c) and from step (d).

In certain embodiments, said transfected host cells are transiently transfected. In certain embodiments, said transfected host cells are stably transfected.

In some embodiments, the FPRL2 amino acid sequence is the amino acid sequence of SEQ ID NO:2. In some embodiments, the FPRL2 amino acid sequence is a variant of the amino acid sequence of SEQ ID NO:2. In some embodiments, said variant of the amino acid sequence of SEQ ID NO:2 is an allelic variant or mammalian ortholog of said amino acid sequence. In some embodiments, said variant of the amino acid sequence of SEQ ID NO:2 is a non-endogenous, constitutively activated mutant of said amino acid sequence or of an allelic variant or mammalian ortholog of said amino acid sequence. In certain embodiments, said non-endogenous, constitutively activated mutant is the amino acid sequence of SEQ ID NO:12. In certain embodiments, said variant of the amino acid sequence of SEQ ID NO:2 is a biologically active fragment of said amino acid sequence or of an allelic variant or mammalian ortholog of said amino acid sequence. In certain embodiments, said biologically active fragment is amino acids 2-353 of the amino acid sequence of SEQ ID NO:2 or of an allelic variant or mammalian ortholog of said amino acid sequence. In certain embodiments, said variant of the amino acid sequence of SEQ ID NO:2 is at least about 75%, at least about 80%, at least about 85%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2. In some embodiments, said variant of the amino acid sequence of SEQ ID NO:2 is at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2.

In certain embodiments, said GPCR comprising an FPRL2 amino acid sequence is a fusion protein comprising one or more epitope tags. In certain embodiments, said fusion protein comprising one or more epitope tags is the amino acid sequence of SEQ ID NO:6.

In certain embodiments, said G protein is pertussis toxin sensitive. In certain embodiments, said G protein is Gi or Go. In certain embodiments, said G protein is Gi. In certain embodiments, said G protein is Go.

In certain embodiments, said G protein is Gα15 or Gα16. In certain embodiments, said G protein is Gα15. In certain embodiments, said G protein is Gα16.

In certain embodiments, said G protein is Gq.

In other certain embodiments, said determining or said comparing is through the use of a Melanophore assay.

In certain embodiments, said determining or said comparing is through the measurement of the level of a second messenger selected from the group consisting of cyclic AMP (cAMP), cyclic GMP (cGMP), inositol triphosphate (IP$_3$), diacylglycerol (DAG), and Ca$^{2+}$. In further preferred embodiments, said second messenger is cAMP. In certain embodiments, the level of the cAMP is reduced. In some embodiments, said measurement of cAMP is carried out with membrane comprising said GPCR.

In certain embodiments, said determining or said comparing is through CRE-reporter assay. In certain embodiments, said reporter is luciferase. In some embodiments, said reporter is β-galactosidase.

In certain embodiments, said determining or said comparing is through measurement of intracellular $Ca^{2+}$. In certain embodiments, the level of intracellular $Ca^{2+}$ is increased. In certain embodiments, said $Ca^{2+}$ measurement is carried out by FLIPR.

In certain embodiments, said host cell comprises Gα15 or Gα16 or chimeric Gq(del)/Gi alpha subunit and said determining or said comparing is through measurement of intracellular $Ca^{2+}$. In certain embodiments, said host cell comprises Gα15 and said determining or said comparing is through measurement of intracellular $Ca^{2+}$. In certain embodiments, said host cell comprises Gα16 and said determining or said comparing is through measurement of intracellular $Ca^{2+}$. In certain embodiments, said host cell comprises chimeric Gq(del)/Gi alpha subunit and said determining or said comparing is through measurement of intracellular $Ca^{2+}$.

In certain embodiments, said determining or said comparing is through measurement of intracellular $IP_3$. In certain embodiments, the level of intracellular $IP_3$ is increased.

In certain embodiments, said host cell comprises Gα15 or Gα16 or chimeric Gq(del)/Gi alpha subunit and said determining or said comparing is through measurement of intracellular $IP_3$. In certain embodiments, said host cell comprises Gα15 and said determining or said comparing is through measurement of intracellular $IP_3$. In certain embodiments, said host cell comprises Gα16 and said determining or said comparing is through measurement of intracellular $IP_3$. In certain embodiments, said host cell comprises chimeric Gq(del)/Gi alpha subunit and said determining or said comparing is through measurement of intracellular $IP_3$.

In certain embodiments, said determining or said comparing is through the measurement of GTPγS binding to membrane comprising said GPCR. In certain embodiments, said GTPγS is labeled with [$^{35}$S].

In certain embodiments, said method further comprises the step of comparing the modulation of the receptor caused by the candidate compound to a second modulation of the receptor caused by contacting the receptor with a known modulator of the receptor. In certain embodiments, said known modulator is an agonist. In certain embodiments, said agonist is Humanin or a peptide analog or derivative thereof. In certain embodiments, said analog of Humanin is [Gly14]-Humanin. In certain embodiments, said agonist is Compound 1.

In a second aspect, the invention features a compound, wherein said compound is a Dimethyl octahydro-phenanthrene carboxylic acid amide derivative of Formula (I):

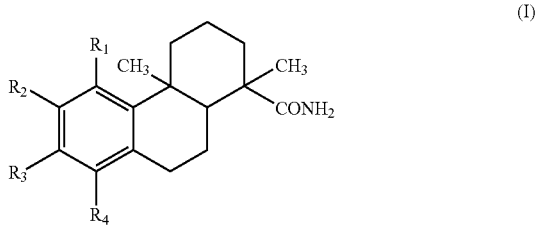

wherein:
$R_1$-$R_4$ are each independently selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{2-6}$ alkynyl, $C_{1-4}$ alkylamino, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and thiol; or a pharmaceutically acceptable salt, solvate or hydrate thereof.

In certain embodiments, at least one $R_1$-$R_4$ group is not H.

In certain embodiments, when $R_1$, $R_3$, and $R_4$ are each H, then $R_2$ is not —OAc or —OCH$_3$.

In certain embodiments, when $R_1$, and $R_4$ are both H, and $R_3$ is —CH$_3$, then $R_2$ is not —OH.

In certain embodiments, when $R_1$, and $R_4$ are both H, and $R_2$ is H or Br, then $R_3$ is not —CH(CH$_3$)$_2$.

In certain embodiments, when $R_1$, $R_2$, and $R_3$ are each H, then R is not —OAc.

In certain embodiments, $R_1$ is H or halogen. In certain embodiments, $R_1$ is H and can be represented by Formula (Ib) as shown below:

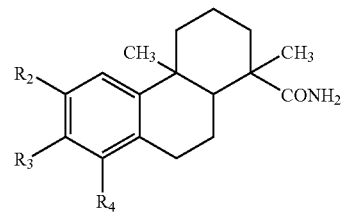

wherein each variable in Formula (Ib) has the same meaning as described herein, supra and infra.

In certain embodiments, $R_4$ is H or halogen. In certain embodiments, $R_4$ is H and can be represented by Formula (Id) as shown below:

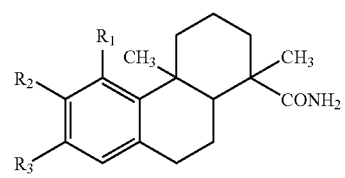

wherein each variable in Formula (Id) has the same meaning as described herein, supra and infra. In certain embodiment, compound of the present invention are of Formula (Id) wherein $R_1$ is H; these compound can be represented by Formula (If) as shown below:

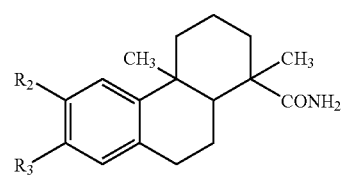

wherein each variable in Formula (Id) has the same meaning as described herein, supra and infra.

In certain embodiment, $R_2$ is selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{2-6}$ dialkylamino, halogen, hydroxyl, nitro, and thiol.

In certain embodiment, $R_2$ is selected form the group consisting of H, $C_{2-6}$ alkynyl, $C_{1-4}$ alkylamino, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, $C_{1-4}$ haloalkoxy, $C_{1-4}$ haloalkyl, $C_{1-4}$ haloalkylsulfinyl, $C_{1-4}$ haloalkylsulfonyl, and $C_{1-4}$ haloalkylthio.

In certain embodiment, $R_2$ is H or halogen. In some embodiments, $R_2$ is H.

In certain embodiment, $R_3$ is selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{2-6}$ dialkylamino, halogen, hydroxyl, nitro, and thiol. In certain embodiment, $R_3$ is $C_{1-6}$ alkyl. In certain embodiment, $R_3$ is selected form the group consisting of H, $C_{2-6}$ alkynyl, $C_{1-4}$ alkylamino, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, $C_{1-4}$ haloalkoxy, $C_{1-4}$ haloalkyl, $C_{1-4}$ haloalkylsulfinyl, $C_{1-4}$ haloalkylsulfonyl, and $C_{1-4}$ haloalkylthio.

In a third aspect, the invention features a compound of Formula (I):

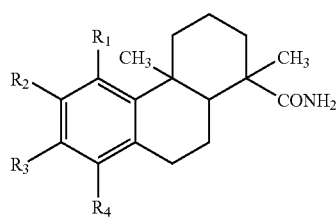

wherein:

$R_1$-$R_4$ are each independently selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{2-6}$ alynyl, $C_{1-4}$ alkylamino, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{1-6}$ dialkylamino, C dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and thiol; or a pharmaceutically acceptable salt, solvate or hydrate thereof.

In a fourth aspect, the invention features a modulator of a GPCR identified according to a method of the first aspect, provided that the modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. The invention also features a modulator of a GPCR identified according to a method of the first aspect, provided that the modulator is not a peptide.

The invention also features a modulator of a GPCR identifiable according to a method of the first aspect, provided that the modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. The invention also features a modulator of a GPCR identifiable according to a method of the first aspect, provided that the modulator is not a peptide.

In certain embodiments, said modulator is selected from the group consisting of agonist, partial agonist, inverse agonist and antagonist. In certain embodiments, said modulator is an agonist. In certain embodiments, said modulator is a partial agonist. In certain embodiments, said modulator is an inverse agonist. In certain embodiments, said modulator is an antagonist.

In certain embodiments, said modulator is preferably an agonist. In certain embodiments, said agonist is a compound according to the second aspect. In certain embodiments, said agonist is a compound according to the third aspect.

In some embodiments, said modulator is an agonist with an $EC_{50}$ of less than 100 μM, of less than 10 μM, or of less than 1 μM. In some embodiments, said modulator is an agonist with an $EC_{50}$ of less than a value selected from the interval of 1 μM to 100 μM. In some embodiments, said modulator is an agonist with an $EC_{50}$ of less than a value selected from the interval of 1 μM to 10 μM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 μM, of less than 10 μM, or of less than 1 μM in said assay. In some embodiments, said modulator is an agonist with an $EC_{50}$ of less than 100 μM in said assay. In some embodiments, said modulator is an agonist with an $EC_{50}$ of less than 90 μM in said assay. In some embodiments, said modulator is an inverse agonist or antagonist with an EC50 of less than 80 μM in said assay. In some embodiments, said modulator is an agonist with an $EC_{50}$ of less than 70 μM in said assay. In some embodiments, said modulator is an agonist with an $EC_{50}$ of less than 60 μM in said assay. In some embodiments, said modulator is an agonist with an $EC_{50}$ of less than 50 μM in said assay. In some embodiments, said modulator is an agonist with an $EC_{50}$ of less than 40 μM in said assay. In some embodiments, said modulator is an agonist with an $EC_{50}$ of less than 30 μM in said assay. In some embodiments, said modulator is an agonist with an $EC_{50}$ of less than 20 μM in said assay. In some embodiments, said modulator is an agonist with an $EC_{50}$ of less than 10 μM in said assay. In some embodiments, said modulator is an agonist with an $EC_{50}$ of less than 9 μM in said assay. In some embodiments, said modulator is an agonist with an $EC_{50}$ of less than 8 μM in said assay. In some embodiments, said modulator is an agonist with an $EC_{50}$ of less than 7 μM in said assay. In some embodiments, said modulator is an agonist with an $EC_{50}$ of less than 6 μM in said assay. In some embodiments, said modulator is an agonist with an $EC_{50}$ of less than 5 μM in said assay. In some embodiments, said modulator is an agonist with an $EC_{50}$ of less than 4 μM in said assay. In some embodiments, said modulator is an agonist with an $EC_{50}$ of less than 3 μM in said assay. In some embodiments, said modulator is an agonist with an $EC_{50}$ of less than 2 μM in said assay. In some embodiments, said modulator is an agonist with an $EC_{50}$ of less than 1 μM in said assay. In some embodiments, said modulator is an agonist with an $EC_{50}$ in said assay of less than a value selected from the interval of 1 μM to 100 μM. In some embodiments, said modulator is an agonist with an $EC_{50}$ in said assay of less than a value selected from the interval of 1 μM to 10 μM.

In some embodiments, said modulator is an inverse agonist or an antagonist with an $IC_{50}$ of less than a value selected from the interval of 1 μM to 100 μM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 μM, less than 90 μM, less than 80 μM, less than 70 μM, less than 60 μM, less than 50 μM, less than 40 μM, less than 30 μM, less than 20 μM, or less than 10 μM. In some embodiments, said modulator is an inverse agonist or an antagonist with an $IC_{50}$ in said assay of less than a value selected from the interval of 1 μM to 10 μM. In certain embodiments, said modulator is an inverse agonist or an antagonist with an $IC_{50}$ in said assay of less than 10 μM, less than 9 mM, less than 8 μM, less than 7 μM, less than 6 μM, less than 5 μM, less than 4 μM, less than 3 μM, less than 2 μM, or less than 1 μM.

In some embodiments, said modulator is selective for the GPCR.

In some embodiments, said modulator modulates a Humanin GPCR.

In some embodiments, said modulator is cell death-protective.

In some embodiments, said modulator is neuroprotective.

In some embodiments, said modulator is myoprotective.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In some embodiments, said orally bioavailable modulator is further able to cross the blood-brain barrier.

In a fifth aspect, the invention features a method of preparing a pharmaceutical or physiologically acceptable composition comprising admixing a carrier and a modulator of a Humanin GPCR, said receptor comprising an FPRL2 amino acid sequence. In certain embodiments, the modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, the modulator is not a peptide. In certain embodiments, the modulator is selected from the group consisting of agonist, partial agonist, inverse agonist, and antagonist. In certain embodiments, the modulator is an agonist. In certain embodiments, the modulator is a partial agonist. In certain embodiments, the modulator is an inverse agonist. In certain embodiments, the modulator is an antagonist. In certain embodiments, the modulator is preferably an agonist. In certain embodiments, said agonist is a compound according to the second aspect. In certain embodiments, said agonist is a compound according to the third aspect.

The invention also features a method of preparing a pharmaceutical or physiologically acceptable composition which comprises identifying a modulator of a Humanin GPCR, wherein said receptor comprises an FPRL2 amino acid sequence, and then admixing a carrier and the modulator, wherein the modulator is identifiable by a method according to a method of the first aspect. In certain embodiments, the modulator is identified according to a method of the first aspect. In certain embodiments, the modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, the modulator is not a peptide. In certain embodiments, the modulator is selected from the group consisting of agonist, partial agonist, inverse agonist, and antagonist. In certain embodiments, the modulator is an agonist. In certain embodiments, the modulator is a partial agonist. In certain embodiments, the modulator is an inverse agonist. In certain embodiments, the modulator is an antagonist. In certain embodiments, the modulator is preferably an agonist. In certain embodiments, said agonist is a compound according to the second aspect. In certain embodiments, said agonist is a compound according to the third aspect.

In certain embodiments, said composition is pharmaceutical. In certain embodiments, said composition is physiologically acceptable.

In some embodiments, said modulator is an agonist with an $EC_{50}$ of less than 100 μM, of less than 10 μM, or of less than 1 μM. In some embodiments, said modulator is an agonist with an $EC_{50}$ of less than a value selected from the interval of 1 μM to 100 μM. In some embodiments, said modulator is an agonist with an $EC_{50}$ of less than a value selected from the interval of 1 μM to 10 μM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 μM, of less than 10 μM, or of less than 1 μM in said assay. In some embodiments, said modulator is an agonist with an $EC_{50}$ of less than 100 μM in said assay. In some embodiments, said modulator is an agonist with an $EC_{50}$ of less than 90 μM in said assay. In some embodiments, said modulator is an inverse agonist or antagonist with an $EC_{50}$ of less than 80 μM in said assay. In some embodiments, said modulator is an agonist with an $EC_{50}$ of less than 70 μM in said assay. In some embodiments, said modulator is an agonist with an $EC_{50}$ of less than 60 μM in said assay. In some embodiments, said modulator is an agonist with an $EC_{50}$ of less than 50 μM in said assay. In some embodiments, said modulator is an agonist with an $EC_{50}$ of less than 40 μM in said assay. In some embodiments, said modulator is an agonist with an $EC_{50}$ of less than 30 μM in said assay. In some embodiments, said modulator is an agonist with an $EC_{50}$ of less than 20 μM in said assay. In some embodiments, said modulator is an agonist with an $EC_{50}$ of less than 10 μM in said assay. In some embodiments, said modulator is an agonist with an $EC_{50}$ of less than 9 μM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In some embodiments, said modulator is selective for the GPCR.

In some embodiments, said modulator modulates a Humanin GPCR.

In some embodiments, said modulator is cell death-protective.

In some embodiments, said modulator is neuroprotective.

In some embodiments, said modulator is myoprotective.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In some embodiments, said orally bioavailable modulator is finder able to cross the blood-brain barrier.

In a sixth aspect, the invention features a method of modulating the activity of a Humanin GPCR, said receptor comprising an FPRL2 amino acid sequence, comprising the step of contacting the receptor with a modulator of the receptor. In certain embodiments, the modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, the modulator is not a peptide. In certain embodiments, the modulator is selected from the group consisting of agonist, partial agonist, inverse agonist, and antagonist. In certain embodiments, the modulator is an agonist. In certain embodiments, the modulator is a partial agonist. In certain embodiments, the modulator is an inverse agonist. In certain embodiments, the modulator is an antagonist. In certain embodiments, the modulator is preferably an agonist. In certain embodiments, said agonist is a compound according to the second aspect. In certain embodiments, said agonist is a compound according to the third aspect.

The invention also features a method of modulating the activity of a Humanin GPCR, said receptor comprising an FPRL2 amino acid sequence, comprising the step of contacting the receptor with a modulator of the receptor, wherein the modulator is identifiable by a method of the first aspect. In certain embodiments, the modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, the modulator is not a peptide. In certain embodiments, the modulator is selected from the group consisting of agonist, partial agonist, inverse agonist, and antagonist. In certain embodiments, the modulator is an agonist. In certain embodiments, the modulator is a partial agonist. In certain embodiments, the modulator is an inverse agonist. In certain embodiments, the modulator is an antagonist. In certain embodiments, the modulator is preferably an agonist. In certain embodiments, said agonist is a compound according to the second aspect. In certain embodiments, said agonist is a compound according to the third aspect.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In some embodiments, said modulator is selective for the GPCR.

In some embodiments, said modulator modulates a Humanin GPCR.

In some embodiments, said modulator is cell death-protective.

In some embodiments, said modulator is neuroprotective.

In some embodiments, said modulator is myoprotective.

In some embodiments, said modulator opposes protection from cell death.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In some embodiments, said orally bioavailable modulator is further able to cross the blood-brain barrier.

In certain embodiments, said contacting comprises administration of the modulator to a membrane comprising the receptor.

In certain embodiments, said contacting comprises administration of the modulator to a cell comprising the receptor.

In certain embodiments, said contacting comprises administration of the modulator to a tissue comprising the receptor.

In certain embodiments, said contacting comprises administration of the modulator to an individual comprising the receptor. In certain embodiments, said individual is a mammal. In certain embodiments, said individual is a non-human mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In certain embodiments, said administration to an individual is oral.

In some embodiments, said modulator is an agonist and said individual is in need of prevention of or treatment for cell death, wherein said cell is non-neuronal and non-muscle.

In some embodiments, said modulator is an agonist and said individual is in need of prevention of or treatment for a cell death-related disorder, wherein said cell is non-neuronal and non-muscle.

In some embodiments, said modulator is an inverse agonist or an antagonist and said individual is in need of opposition to protection from cell death, wherein said cell is non-neuronal and non-muscle.

In some embodiments, said modulator is an inverse agonist or an antagonist and said individual is in need of prevention of or treatment for a cell proliferative disorder, wherein said cell is non-neuronal and non-muscle.

In certain embodiments, said modulator is an agonist and said individual is in need of reduction of neuronal cell death.

In certain embodiments, said modulator is an agonist and said individual is in need of prevention of or treatment for a neuronal cell death-related disorder. In certain embodiments, said neuronal cell death-related disorder is selected from the group consisting of:
  (a) Alzheimer's disease;
  (b) Parkinson's disease;
  (c) stroke;
  (d) motor-neuron disease;
  (e) learning or memory impairment;
  (f) traumatic brain injury;
  (g) spinal cord injury;
  (h) peripheral neuropathy; and
  (i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is an inverse agonist or an antagonist and said individual is in need of opposition to protection from neuronal cell death.

In certain embodiments, said modulator is an inverse agonist or an antagonist and said individual is in need of prevention of or treatment for a neuronal cell proliferative disorder. In certain embodiments, said neuronal cell proliferative disorder is neuroblastoma. In other embodiments, said neuronal cell proliferative disorder is medulloblastoma.

In certain embodiments, said modulator is an agonist and said individual is in need of reducing muscle cell death.

In certain embodiments, said modulator is an agonist and said individual is in need of prevention of or treatment for a muscle cell death-related disorder. In certain embodiments, said muscle cell death-related disorder is selected from the group consisting of:
 (a) cerebral amyloid beta-protein angiopathy;
 (b) myocardial infarction; and
 (c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is an inverse agonist or an antagonist and said individual is in need of opposition to protection from muscle cell death.

In certain embodiments, said modulator is an inverse agonist or an antagonist and said individual is in need of prevention of or treatment for a muscle cell proliferative disorder. In certain embodiments, said muscle cell proliferative disorder is selected from the group consisting of atherosclerosis, restenosis, and tumor-supportive angiogenesis.

In a seventh aspect, the invention features the method of the sixth aspect, wherein an in vitro cell culture comprises one or more cells comprising said Humanin GPCR, and wherein said cell culture is in need of prevention of or treatment for cell death.

In certain embodiments, said method comprises administration of an effective amount of the modulator to a cell comprising the receptor.

In certain embodiments, said modulator is an agonist.

In certain embodiments, said one or more cells comprises one or more neuronal cells.

In certain embodiments, said one or more cells comprises one or more muscle cells.

In some embodiments, said one or more cells comprises one or more cells that are non-neuronal and non-muscle.

In certain embodiments, culture medium used in said cell culture comprises said modulator.

In certain embodiments, said modulator is provided as a supplement to cell culture medium.

In certain embodiments, said modulator is identified according to a method of the first aspect.

In certain embodiments, said modulator is a compound according to the second aspect.

In certain embodiments, said modulator is a compound according to the third aspect.

In certain embodiments, said modulator is Compound 1.

In certain embodiments, said modulator is Compound 1 and said effective amount of Compound 1 is about 0.5 µM, about 1.0 µM, about 2.0 µM, about 3.0 µM, about 4.0 µM, about 5.0 µM, about 6.0 µM, about 7.0 µM, about 8.0 µM, about 9.0 µM, about 10.0 µM, about 20.0 µM, about 30.0 µM, about 40.0 µM or about 50 µM.

In an eighth aspect, the invention features a method of modulating the activity of a Humanin GPCR, said receptor comprising an FPRL2 amino acid sequence, wherein said modulation is for reducing neuronal cell death in an individual in need of said modulation, comprising contacting said receptor with a therapeutically effective amount of a modulator of the receptor.

The invention also features a method of modulating the activity of a Humanin GPCR, said receptor comprising an FPRL2 amino acid sequence, wherein said modulation is for preventing or treating a neuronal cell death-related disorder in an individual in need of said modulation, comprising contacting said receptor with a therapeutically effective amount of a modulator of the receptor. In certain embodiments, said neuronal cell death-related disorder is selected from the group consisting of:
 (a) Alzheimer's disease;
 (b) Parkinson's disease;
 (c) stroke;
 (d) motor-neuron disease;
 (e) learning or memory impairment;
 (d) traumatic brain injury;
 (e) spinal cord injury;
 (f) peripheral neuropathy; and
 (g) prion-associated disease.

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said $EC_{50}$ is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy (DSP).

The invention also relates to a method of modulating a Humanin GPCR, said receptor comprising an FPRL2 amino acid sequence, wherein said modulation is for preventing or treating a neuronal cell proliferative disorder in an individual in need of said modulation, comprising contacting a therapeutically effective amount of a modulator of said receptor with said receptor. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an ninth aspect, the invention features a method of modulating the activity of a Humanin GPCR, said receptor comprising an FPRL2 amino acid sequence, wherein said modulation is for reducing muscle cell death in an individual in need of said modulation, comprising contacting said receptor with a therapeutically effective amount of a modulator of the receptor.

The invention also features a method of modulating the activity of a Humanin GPCR, said receptor comprising an FPRL2 amino acid sequence, wherein said modulation is for preventing or treating a muscle cell death-related disorder in an individual in need of said modulation, comprising contacting said receptor with a therapeutically effective amount of a modulator of the receptor. In certain embodiments, said muscle cell death-related disorder is selected from the group consisting of:
(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of modulating a Humanin GPCR, said receptor comprising an FPRL2 amino acid sequence, wherein said modulation is for preventing or treating a muscle cell proliferative disorder in an individual in need of said modulation, comprising contacting a therapeutically effective amount of a modulator of said receptor with said receptor. In certain embodiments, said modulator is an inverse agonist. In certain embodiments, said modulator is an antagonist. In certain embodiments, said muscle cell proliferative disorder is selected from the group consisting of:

(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said individual is a mammal. In certain embodiments, said individual is a non-human mammal. certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a tenth aspect, the invention features a method of modulating the activity of a Humanin GPCR, said receptor comprising an FPRL2 amino acid sequence, wherein said modulation is for reducing cell death in an individual in need of said modulation, wherein said cell in not neuronal and not muscle, comprising contacting said receptor with a therapeutically effective amount of a modulator of the receptor.

The invention also features a method of modulating the activity of a Humanin GPCR, said receptor comprising an FPRL2 amino acid sequence, wherein said modulation is for preventing or treating a cell death-related disorder in an individual in need of said modulation, comprising contacting said receptor with a therapeutically effective amount of a modulator of the receptor. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said $EC_{50}$ is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40

µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of modulating a Humanin GPCR, said receptor comprising an FPRL2 amino acid sequence, wherein said modulation is for preventing or treating a cell proliferative disorder in an individual in need of said modulation, comprising contacting a therapeutically effective amount of a modulator of said receptor with said receptor. In certain embodiments, said modulator is an inverse agonist. In certain embodiments, said modulator is an antagonist.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an eleventh aspect, the invention features a method of reducing neuronal cell death in an individual in need of said reducing, comprising contacting a therapeutically effective amount of a modulator of a Humanin GPCR with said receptor, said GPCR comprising an FPRL2 amino acid sequence.

The invention also features a method of preventing or treating a neuronal cell death-related disorder in an individual in need of said prevention or treatment, comprising contacting a therapeutically effective amount of a modulator of a Human GPCR with said receptor, said receptor comprising an FPRL2 amino acid sequence. In certain embodiments, said neuronal cell death-related disorder is selected from the group consisting of:

(a) Alzheimer's disease;
(b) Parkinson's disease;
(c) stroke;
(d) motor-neuron disease;
(e) learning or memory impairment;
(d) traumatic brain injury;
(e) spinal cord injury;
(f) peripheral neuropathy; and
(g) prion-associated disease.

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

The invention also features a method of preventing or treating a neuronal cell proliferative disorder in an individual in need of said prevention or treatment, comprising contacting a therapeutically effective amount of a modulator of a Humanin GPCR with said receptor, said receptor comprising an FPRL2 amino acid sequence. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an twelfth aspect, the invention features a method of reducing muscle cell death in an individual in need of said reducing, comprising contacting a therapeutically effective amount of a modulator of a Humanin GPCR with said receptor, said GPCR comprising an FPRL2 amino acid sequence.

The invention also features a method of preventing or treating a muscle cell death-related disorder in an individual in need of said prevention or treatment, comprising contacting a therapeutically effective amount of a modulator of a Humanin GPCR with said receptor, said receptor comprising an FPRL2 amino acid sequence. In certain embodiments, said muscle cell death-related disorder is selected from the group consisting of:
(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of preventing or treating a muscle cell proliferative disorder in an individual in need of said prevention or treatment, comprising contacting a therapeutically effective amount of a modulator of a Humanin GPCR, said receptor comprising an FPRL2 amino acid sequence, with the receptor. In certain embodiments, said modulator is an inverse agonist. In certain embodiments, said modulator is an antagonist. In certain embodiments, said muscle cell proliferative disorder is selected from the group consisting of:

(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said individual is a mammal. In certain embodiments, said individual is a non-human mammal. certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a thirteenth aspect, the invention features a method of reducing cell death in an individual in need of said reducing, comprising contacting a therapeutically effective amount of a modulator of a Humanin GPCR with said receptor, said GPCR comprising an FPRL2 amino acid sequence.

The invention also features a method of preventing or treating a cell death-related disorder in an individual in need of said prevention or treatment, comprising contacting a therapeutically effective amount of a modulator of a Humanin GPCR with said receptor, said receptor comprising an FPRL2 amino acid sequence. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of preventing or treating cell proliferative disorder in an individual in need of said prevention or treatment, comprising contacting a therapeutically effective amount of a modulator of a Humanin GPCR, said receptor comprising an FPRL2 amino acid sequence, with the receptor. In certain embodiments, said modulator is an inverse agonist. In certain embodiments, said modulator is an antagonist.

In certain embodiments, said individual is a mammal. In certain embodiments, said individual is a non-human mammal. certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fourteenth aspect, the invention features a pharmaceutical or physiologically acceptable composition comprising, consisting essentially of, or consisting of a modulator a Humanin GPCR, said receptor comprising an FPRL2 amino acid sequence.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said composition is pharmaceutical. In certain embodiments, said composition is physiologically acceptable.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In certain embodiments, said modulator is neuroprotective.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In a fifteenth aspect, the invention features a method of reducing neuronal cell death comprising providing or administering to an individual in need of said reduction said pharmaceutical or physiologically acceptable composition of the fourteenth aspect.

The invention also features a method of preventing or treating a neuronal cell death-related disorder comprising providing or administering to an individual in need of said prevention or treatment said pharmaceutical or physiologically acceptable composition of the fourteenth aspect. In certain embodiments, said neuronal cell death-related disorder is selected from the group consisting of:
  (a) Alzheimer's disease;
  (b) Parkinson's disease;
  (c) stroke;
  (d) motor-neuron disease;
  (e) learning or memory impairment;
  (f) traumatic brain injury;
  (g) spinal cord injury;
  (h) peripheral neuropathy; and
  (i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is an agonist.

In certain embodiments, a therapeutically effective amount of said pharmaceutical or physiologically acceptable composition is provided or administered to said individual.

In certain embodiments, said providing or administering of said pharmaceutical or physiologically acceptable composition is oral.

The invention also relates to a method of preventing or treating a neuronal cell proliferative disorder comprising providing or administering to an individual in need of said prevention or treatment said pharmaceutical or physiologically acceptable composition of the fourteenth aspect. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a sixteenth aspect, the invention features a method of reducing muscle cell death comprising providing or administering to an individual in need of said reduction said pharmaceutical or physiologically acceptable composition of the fourteenth aspect.

The invention also features a method of preventing or treating a muscle cell death-related disorder comprising providing or administering to an individual in need of said prevention or treatment said pharmaceutical or physiologically acceptable composition of the fourteenth aspect. In certain embodiments, said cell death-related disorder is selected from the group consisting of:
(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is an agonist.

In certain embodiments, a therapeutically effective amount of said pharmaceutical or physiologically acceptable composition is provided or administered to said individual.

In certain embodiments, said providing or administering of said pharmaceutical or physiologically acceptable composition is oral.

The invention also relates to a method of preventing or treating a muscle cell proliferative disorder comprising providing or administering to an individual in need of said prevention or treatment said pharmaceutical or physiologically acceptable composition of the fourteenth aspect. In certain embodiments, said modulator is an inverse agonist. In certain embodiments, said modulator is an antagonist. In certain embodiments, said muscle cell proliferative disorder selected from the group consisting of:
(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a seventeenth aspect, the invention features a method of reducing cell death comprising providing or administering to an individual in need of said reduction said pharmaceutical or physiologically acceptable composition of the fourteenth aspect.

The invention also features a method of preventing or treating a cell death-related disorder comprising providing or administering to an individual in need of said prevention or treatment said pharmaceutical or physiologically acceptable composition of the fourteenth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, a therapeutically effective amount of said pharmaceutical or physiologically acceptable composition is provided or administered to said individual.

In certain embodiments, said providing or administering of said pharmaceutical or physiologically acceptable composition is oral.

The invention also relates to a method of preventing or treating a cell proliferative disorder comprising providing or administering to an individual in need of said prevention or treatment said pharmaceutical or physiologically acceptable composition of the fourteenth aspect. In certain embodiments, said modulator is an inverse agonist. In certain embodiments, said modulator is an antagonist.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an eighteenth aspect, the invention features a modulator of a Humanin GPCR, said receptor comprising an FPRL2 amino acid sequence, for use in a method of treatment of the human animal body by therapy.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said $EC_{50}$ is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an $EC50$ of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said animal is a mammal. In certain embodiments, said mammal is a horse, cow, sheep, pig, cat, dog, rabbit, mouse, rat, or non-human primate. More preferred of human or animal is human.

In an nineteenth aspect, the invention features a modulator of a Humanin GPCR, said receptor comprising an FPRL2 amino acid sequence, for use in a method of reducing neuronal cell death in the human animal body by therapy.

The invention also features a modulator of a Humanin GPCR, said receptor comprising an FPRL2 amino acid sequence, for use in a method of prevention of or treatment for a neuronal cell death-related disorder in a human or animal body by therapy. In certain embodiments, said neuronal cell death-related disorder is selected from the group consisting of:
  (a) Alzheimer's disease;
  (b) Parkinson's disease;
  (c) stroke;
  (d) motor-neuron disease;
  (e) learning or memory impairment;
  (f) traumatic brain injury;
  (g) spinal cord injury;
  (h) peripheral neuropathy; and
  (i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ HD NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a modulator of a Humanin GPCR, said receptor comprising an FPRL2 amino acid sequence, for use in a method of prevention of or treatment for a neuronal cell proliferative disorder in a human or animal body by therapy. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said animal is a mammal. In certain embodiments, said mammal is a horse, cow, sheep, pig, cat, dog, rabbit, mouse, rat, or non-human primate. More preferred of human or animal is human.

In an twentieth aspect, the invention features a modulator of a Humanin GPCR, said receptor comprising an FPRL2 amino acid sequence, for use in a method of reducing muscle cell death in the human animal body by therapy.

The invention also features a modulator of a Humanin GPCR, said receptor comprising an FPRL2 amino acid sequence, for use in a method of prevention of or treatment for a muscle cell death-related disorder in a human or animal body by therapy. In certain embodiments, said muscle cell death-related disorder is selected from the group consisting of:
(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a modulator of a Humanin GPCR, said receptor comprising an FPRL2 amino acid sequence, for use in a method of prevention of or treatment for a muscle cell proliferative disorder in a human or animal body by therapy. In certain embodiments, said modulator is an inverse agonist. In certain embodiments, said modulator is an antagonist. In certain embodiments, said muscle cell proliferative disorder selected from the group consisting of:
  (a) atherosclerosis;
  (b) restenosis; and
  (c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said animal is a mammal. In certain embodiments, said mammal is a horse, cow, sheep, pig, cat, dog, rabbit, mouse, rat, or non-human primate. More preferred of human or animal is human.

In a twenty-first aspect, the invention features a modulator of a Humanin GPCR, said receptor comprising an FPRL2 amino acid sequence, for use in a method of reducing cell death in the human animal body by therapy.

The invention also features a modulator of a Humanin GPCR, said receptor comprising an FPRL2 amino acid sequence, for use in a method of prevention of or treatment for a cell death-related disorder in a human or animal body by therapy. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a modulator of a Humanin GPCR, said receptor comprising an FPRL2 amino acid sequence, for use in a method of prevention of or treatment for a cell proliferative disorder in a human or animal body by therapy. In certain embodiments, said modulator is an inverse agonist. In certain embodiments, said modulator is an antagonist.

In certain embodiments, said animal is a mammal. In certain embodiments, said mammal is a horse, cow, sheep, pig, cat, dog, rabbit, mouse, rat, or non-human primate. More preferred of human or animal is human.

In a twenty-second aspect, the invention features a method of using a modulator of a Humanin GPCR, said receptor comprising an FPRL2 amino acid sequence, for the preparation of a medicament for the reduction of neuronal cell death.

The invention also features a method of using a modulator of a Humanin GPCR, said receptor comprising an FPRL2 amino acid sequence, for the preparation of a medicament for the prevention or treatment of a neuronal cell death-related disorder. In certain embodiments, said neuronal cell death-related disorder is selected from the group consisting of:
  (a) Alzheimer's disease;
  (b) Parkinson's disease;
  (c) stroke;
  (d) motor-neuron disease;
  (e) learning or memory impairment;
  (d) traumatic brain injury;
  (e) spinal cord injury;
  (f) peripheral neuropathy; and
  (g) prion-associated disease.

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40

µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

The invention also features a method of using a modulator of a Humanin GPCR, said receptor comprising an FPRL2 amino acid sequence, for the preparation of a medicament for preventing or treating a neuronal cell proliferative disorder. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In a twenty-third aspect, the invention features a method of using a modulator of a Humanin GPCR, said receptor comprising an FPRL2 amino acid sequence, for the preparation of a medicament for the reduction of muscle cell death.

The invention also features a method of using a modulator of a Humanin GPCR, said receptor comprising an FPRL2 amino acid sequence, for the preparation of a medicament for the prevention or treatment of a muscle cell death-related disorder. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a method of using a modulator of a Humanin GPCR, said receptor comprising an FPRL2 amino acid sequence, for the preparation of a medicament for the prevention or treatment of a muscle cell proliferative disorder. In certain embodiments, said modulator is an inverse agonist. In certain embodiments, said modulator is an antagonist. In certain embodiments, said muscle cell proliferative disorder is selected from the group consisting of:

(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In a twenty-fourth aspect, the invention features a method of using a modulator of a Humanin GPCR, said receptor comprising an FPRL2 amino acid sequence, for the preparation of a medicament for the reduction of cell death.

The invention also features a method of using a modulator of a Humanin GPCR, said receptor comprising an FPRL2 amino acid sequence, for the preparation of a medicament for the prevention or treatment of a cell death-related disorder. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is selected from the group consisting of agonist, partial agonist, inverse agonist, and antagonist. In certain preferred embodiments, said modulator is an agonist. In certain embodiments, said agonist is a compound according to the second aspect. In certain embodiments, said agonist is a compound according to the third aspect.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a method of using a modulator of a Humanin GPCR, said receptor comprising an FPRL2 amino acid sequence, for the preparation of a medicament for the prevention or treatment of a cell proliferative disorder. In certain embodiments, said modulator is an inverse agonist. In certain embodiments, said modulator is an antagonist.

In a twenty-fifth aspect, the invention features a method of modulating the activity of a Humanin GPCR, said receptor comprising an FPRL2 amino acid sequence, wherein said modulation is for reducing neuronal cell death in an individual in need of said modulation, comprising contacting said receptor with a therapeutically effective amount of a modulator of the receptor. In certain embodiments, said method comprises performing a method according to the first aspect to thereby identify a modulator.

The invention also features a method of modulating the activity of a Humanin GPCR, said receptor comprising an FPRL2 amino acid sequence, wherein said modulation is for preventing or treating a neuronal cell death-related disorder in an individual in need of said modulation, comprising contacting said receptor with a therapeutically effective amount of a modulator of the receptor. In certain embodiments, said method comprises performing a method according to the first aspect to thereby identify a modulator. In certain embodiments, said neuronal cell death-related disorder is selected from the group consisting of:
 (a) Alzheimer's disease;
 (b) Parkinson's disease;
 (c) stroke;
 (d) motor-neuron disease;
 (e) learning or memory impairment;
 (d) traumatic brain injury;
 (e) spinal cord injury;
 (f) peripheral neuropathy; and
 (g) prion-associated disease.

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM less than 3 µM, less than 2 µM, or less than 1 µM.

In certain embodiments, said contacting comprises oral administration of said modulator to said individual.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

The invention also relates to a method of modulating a Humanin GPCR, said receptor comprising an FPRL2 amino acid sequence, wherein said modulation is for preventing or treating a neuronal cell proliferative disorder in an individual in need of said modulation, comprising contacting a therapeutically effective amount of a modulator of said receptor with said receptor. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a twenty-sixth aspect, the invention features a method of modulating the activity of a Humanin GPCR, said receptor comprising an FPRL2 amino acid sequence, wherein said modulation is for reducing muscle cell death in an individual in need of said modulation, comprising contacting said receptor with a therapeutically effective amount of a modulator of the receptor. In certain embodiments, said method comprises performing a method according to the first aspect to thereby identify a modulator.

The invention also features a method of modulating the activity of a Humanin GPCR, said receptor comprising an FPRL2 amino acid sequence, wherein said modulation is for preventing or treating a muscle cell death-related disorder in an individual in need of said modulation, comprising contacting said receptor with a therapeutically effective amount of a modulator of the receptor. In certain embodiments, said method comprises performing a method according to the first aspect to thereby identify a modulator. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of modulating a Humanin GPCR, said receptor comprising an FPRL2 amino acid sequence, wherein said modulation is for preventing or treating a muscle cell proliferative disorder in an individual in need of said modulation, comprising contacting a therapeutically effective amount of a modulator of said receptor with said receptor. In certain embodiments, said modulator is an inverse agonist. In certain embodiments, said modulator is an antagonist. In certain embodiments, said muscle cell proliferative disorder is selected from the group consisting of:

(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said individual is a mammal. In certain embodiments, said individual is a non-human mammal. certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a twenty-seventh aspect, the invention features a method of modulating the activity of a Humanin GPCR, said receptor comprising an FPRL2 amino acid sequence, wherein said modulation is for reducing cell death in an individual in need of said modulation, wherein said cell in not neuronal and not muscle, comprising contacting said receptor with a therapeutically effective amount of a modulator of the receptor. In certain embodiments, said method comprises performing a method according to the first aspect to thereby identify a modulator.

The invention also features a method of modulating the activity of a Humanin GPCR, said receptor comprising an FPRL2 amino acid sequence, wherein said modulation is for preventing or treating a cell death-related disorder in an individual in need of said modulation, comprising contacting said receptor with a therapeutically effective amount of a modulator of the receptor. In certain embodiments, said method comprises performing a method according to the first aspect to thereby identify a modulator. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of Less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of modulating a Humanin GPCR, said receptor comprising an FPRL2 amino acid sequence, wherein said modulation is for preventing or treating a cell proliferative disorder in an individual in need of said modulation, comprising contacting a therapeutically effective amount of a modulator of said receptor with said receptor. In certain embodiments, said modulator is an inverse agonist. In certain embodiments, said modulator is an antagonist.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an twenty-eighth aspect, the invention features a method of reducing neuronal cell death in an individual in need of said reducing, comprising contacting a therapeutically effective amount of a modulator of a Humanin GPCR with said receptor, said GPCR comprising an FPRL2 amino acid sequence. In certain embodiments, said method comprises performing a method according to the first aspect to thereby identify a modulator.

The invention also features a method of preventing or treating a neuronal cell death-related disorder in an individual in need of said prevention or treatment, comprising contacting a therapeutically effective amount of a modulator of a Human GPCR with said receptor, said receptor comprising an FPRL2 amino acid sequence. In certain embodiments, said method comprises performing a method according to the first aspect to thereby identify a modulator. In certain embodiments, said neuronal cell death-related disorder is selected from the group consisting of:
(a) Alzheimer's disease;
(b) Parkinson's disease;
(c) stroke;
(d) motor-neuron disease;
(e) learning or memory impairment;
(d) traumatic brain injury;
(e) spinal cord injury;
(i) peripheral neuropathy; and
(g) prion-associated disease.

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy (DSP).

The invention also features a method of preventing or treating a neuronal cell proliferative disorder in an individual in need of said prevention or treatment, comprising contacting a therapeutically effective amount of a modulator of a Humanin GPCR with said receptor, said receptor comprising an FPRL2 amino acid sequence. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an twenty-ninth aspect, the invention features a method of reducing muscle cell death in an individual in need of said reducing, comprising contacting a therapeutically effective amount of a modulator of a Humanin GPCR with said receptor, said GPCR comprising an FPRL2 amino acid sequence. In certain embodiments, said method comprises performing a method according to the first aspect to thereby identify a modulator.

The invention also features a method of preventing or treating a muscle cell death-related disorder in an individual in need of said prevention or treatment, comprising contacting a therapeutically effective amount of a modulator of a Humanin GPCR with said receptor, said receptor comprising an FPRL2 amino acid sequence. In certain embodiments, said method comprises performing a method according to the first aspect to thereby identify a modulator. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said contacting comprises oral administration of said modulator to said individual.

The invention also relates to a method of preventing or treating a muscle cell proliferative disorder in an individual in need of said prevention or treatment, comprising contacting a therapeutically effective amount of a modulator of a Humanin GPCR, said receptor comprising an FPRL2 amino acid sequence, with the receptor. In certain embodiments, said modulator is an inverse agonist. In certain embodiments, said modulator is an antagonist. In certain embodiments, said muscle cell proliferative disorder is selected from the group consisting of:

(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said individual is a mammal. In certain embodiments, said individual is a non-human mammal. certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a thirtieth aspect, the invention features a method of reducing cell death in an individual in need of said reducing, comprising contacting a therapeutically effective amount of a modulator of a Humanin GPCR with said receptor, said GPCR comprising an FPRL2 amino acid sequence. In certain embodiments, said method comprises performing a method according to the first aspect to thereby identify a modulator.

The invention also features a method of preventing or treating a cell death-related disorder in an individual in need of said prevention or treatment, comprising contacting a therapeutically effective amount of a modulator of a Humanin GPCR with said receptor, said receptor comprising an FPRL2 amino acid sequence. In certain embodiments, said method comprises performing a method according to the first aspect to thereby identify a modulator. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 μM in said assay. In some embodiments, said modulator is an agonist with an $EC_{50}$ of less than 70 μM in said assay. In some embodiments, said modulator is an agonist with an $EC_{50}$ of less than 60 μM in said assay. In some embodiments, said modulator is an agonist with an $EC_{50}$ of less than 50 μM in said assay. In some embodiments, said modulator is an agonist with an $EC_{50}$ of less than 40 μM in said assay. In some embodiments, said modulator is an agonist with an $EC_{50}$ of less than 30 μM in said assay. In some embodiments, said modulator is an agonist with an $EC_{50}$ of less Man 20 μM in said assay. In some embodiments, said modulator is an agonist with an $EC_{50}$ of less than 10 μM in said assay. In some embodiments, said modulator is an agonist with an $EC_{50}$ of less than 9 μM in said assay. In some embodiments, said modulator is an agonist with an $EC_{50}$ of less than 8 μM in said assay. In some embodiments, said modulator is an agonist with an $EC_{50}$ of less than 7 μM in said assay. In some embodiments, said modulator is an agonist with an $EC_{50}$ of less than 6 μM in said assay. In some embodiments, said modulator is an agonist with an $EC_{50}$ of less than 5 μM in said assay. In some embodiments, said modulator is an agonist with an $EC_{50}$ of less than 4 μM in said assay. In some embodiments, said modulator is an agonist with an $EC_{50}$ of less than 3 μM in said assay. In some embodiments, said modulator is an agonist with an $EC_{50}$ of less than 2 μM in said assay. In some embodiments, said modulator is an agonist with an $EC_{50}$ of less than 1 μM in said assay. In some embodiments, said modulator is an agonist with an $EC_{50}$ in said assay of less than a value selected from the interval of 1 μM to 100 μM. In some embodiments, said modulator is an agonist with an $EC_{50}$ in said assay of less than a value selected from the interval of 1 μM to 10 μm.

In some embodiments, said modulator is an inverse agonist or an antagonist with an $IC_{50}$ of less than a value selected from the interval of 1 μM to 100 μM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 μM, less than 90 μM, less than 80 μM, less than 70 μM, less than 60 μM, less than 50 μM, less than 40 μM, less than 30 μM, less than 20 μM, or less than 10 μM. In some embodiments, said modulator is an inverse agonist or an antagonist with an $IC_{50}$ in said assay of less than a value selected from the interval of 1 μM to 10 μM. In certain embodiments, said modulator is an inverse agonist or an antagonist with an $IC_{50}$ in said assay of less than 10 μM, less than 9 μM, less than 8 μM, less than 7 μM, less than 6 μM, less than 5 μM, less than 4 μM, less than 3 μM, less than 2 μM, or less than 1 μM.

In certain embodiments, said contacting comprises oral administration of said modulator to said individual.

The invention also relates to a method of preventing or treating cell proliferative disorder in an individual in need of said prevention or treatment, comprising contacting a therapeutically effective amount of a modulator of a Humanin GPCR, said receptor comprising an FPRL2 amino acid sequence, with the receptor. In certain embodiments, said modulator is an inverse agonist. In certain embodiments, said modulator is an antagonist.

In certain embodiments, said individual is a mammal. In certain embodiments, said individual is a non-human mammal. certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a thirty-first aspect, the invention features a pharmaceutical or physiologically acceptable composition comprising, consisting essentially of, or consisting of a modulator a Humanin GPCR, said receptor comprising an FPRL2 amino acid sequence. In certain embodiments, said modulator is identifiable by performing a method according to the first aspect. In certain embodiments, said modulator is identified by performing a method according to the first aspect.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said composition is pharmaceutical. In certain embodiments, said composition is physiologically acceptable.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In certain embodiments, said modulator is neuroprotective.
In certain embodiments, said modulator is myoprotective.
In some embodiments, said modulator is an agonist with an $EC_{50}$ of less than 100 μM, of less than 10 μM, or of less than 1 μM. In some embodiments, said modulator is an agonist with an $EC_{50}$ of less than a value selected from the interval of 1 μM to 100 μM. In some embodiments, said modulator is an agonist with an $EC_{50}$ of less than a value selected from the interval of 1 μM to 10 μM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 μM, of less than 10 μM, or of less than 1 μM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In a thirty-second aspect, the invention features a method of reducing neuronal cell death comprising providing or administering to an individual in need of said reduction said pharmaceutical or physiologically acceptable composition of the thirty-first aspect.

The invention also features a method of preventing or treating a neuronal cell death-related disorder comprising providing or administering to an individual in need of said prevention or treatment said pharmaceutical or physiologically acceptable composition of the thirty-first aspect. In certain embodiments, said neuronal cell death-related disorder is selected from the group consisting of:
(a) Alzheimer's disease;
(b) Parkinson's disease;
(c) stroke;
(d) motor-neuron disease;
(e) learning or memory impairment;
(f) traumatic brain injury;
(g) spinal cord injury;
(h) peripheral neuropathy; and
(i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is an agonist.

In certain embodiments, a therapeutically effective amount of said pharmaceutical or physiologically acceptable composition is provided or administered to said individual.

In certain embodiments, said providing or administering of said pharmaceutical or physiologically acceptable composition is oral.

The invention also relates to a method of preventing or treating a neuronal cell proliferative disorder comprising providing or administering to an individual in need of said prevention or treatment said pharmaceutical or physiologically acceptable composition of the thirty-first aspect. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a thirty-third aspect, the invention features a method of reducing muscle cell death comprising providing or administering to an individual in need of said reduction said pharmaceutical or physiologically acceptable composition of the thirty-first aspect.

The invention also features a method of preventing or treating a muscle cell death-related disorder comprising providing or administering to an individual in need of said prevention or treatment said pharmaceutical or physiologically acceptable composition of the thirty-first aspect. In certain embodiments, said cell death-related disorder is selected from the group consisting of:
(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is an agonist.

In certain embodiments, a therapeutically effective amount of said pharmaceutical or physiologically acceptable composition is provided or administered to said individual.

In certain embodiments, said providing or administering of said pharmaceutical or physiologically acceptable composition is oral.

The invention also relates to a method of preventing or treating a muscle cell proliferative disorder comprising providing or administering to an individual in need of said prevention or treatment said pharmaceutical or physiologically acceptable composition of the thirty first aspect. In certain embodiments, said modulator is an inverse agonist. In certain embodiments, said modulator is an antagonist. In certain embodiments, said muscle cell proliferative disorder selected from the group consisting of:
(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis. In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a thirty-fourth aspect, the invention features a method of reducing cell death comprising providing or administering to an individual in need of said reduction said pharmaceutical or physiologically acceptable composition of the thirty-first aspect.

The invention also features a method of preventing or treating a cell death-related disorder comprising providing or administering to an individual in need of said prevention or treatment said pharmaceutical or physiologically acceptable composition of the thirty-first aspect. In certain, embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, a therapeutically effective amount of said pharmaceutical or physiologically acceptable composition is provided or administered to said individual.

In certain embodiments, said providing or administering of said pharmaceutical or physiologically acceptable composition is oral.

The invention also relates to a method of preventing or treating a cell proliferative disorder comprising providing or administering to an individual in need of said prevention or treatment said pharmaceutical or physiologically acceptable composition of the thirty-first aspect. In certain embodiments, said modulator is an inverse agonist. In certain embodiments, said modulator is an antagonist.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In an thirty-fifth aspect, the invention features a modulator of a Humanin GPCR, said receptor comprising an FPRL2 amino acid sequence, for use in a method of treatment of the human or animal body by therapy. In certain embodiments, said modulator is identifiable by performing a method according to the first aspect. In certain embodiments, said modulator is identified by performing a method according to the first aspect.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an EC50 of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

In certain embodiments, said animal is a mammal. In certain embodiments, said mammal is a horse, cow, sheep, pig, cat, dog, rabbit, mouse, rat, or non-human primate. More preferred of human or animal is human.

In an thirty-sixty aspect, the invention features a modulator of a Humanin GPCR, said receptor comprising an FPRL2 amino acid sequence, for use in a method of reducing neuronal cell death in the human or animal body by therapy. In certain embodiments, said modulator is identifiable by performing a method according to the first aspect. In certain embodiments, said modulator is identified by performing a method according to the first aspect.

The invention also features a modulator of a Humanin GPCR, said receptor comprising an FPRL2 amino acid sequence, for use in a method of prevention of or treatment for a neuronal cell death-related disorder in a human or animal body by therapy. In certain embodiments, said modulator is identifiable by performing a method according to the first aspect. In certain embodiments, said modulator is identified by performing a method according to the first aspect. In certain embodiments, said neuronal cell death-related disorder is selected from the group consisting of:

(a) Alzheimer's disease;
(b) Parkinson's disease;
(c) stroke;
(d) motor-neuron disease;
(e) learning or memory impairment;
(f) traumatic brain injury;
(g) spinal cord injury;
(h) peripheral neuropathy; and
(i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ HD NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an $EC_{50}$ of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a modulator of a Humanin GPCR, said receptor comprising an FPRL2 amino acid sequence, for use in a method of prevention of or treatment for a neuronal cell proliferative disorder in a human or animal body by therapy. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In certain embodiments, said animal is a mammal. In certain embodiments, said mammal is a horse, cow, sheep, pig, cat, dog, rabbit, mouse, rat, or non-human primate. More preferred of human or animal is human.

In an thirty-seventh aspect, the invention features a modulator of a Humanin GPCR, said receptor comprising an FPRL2 amino acid sequence, for use in a method of reducing muscle cell death in the human or animal body by therapy. In certain embodiments, said modulator is identifiable by performing a method according to the first aspect. In certain embodiments, said modulator is identified by performing a method according to the first aspect.

The invention also features a modulator of a Humanin GPCR, said receptor comprising an FPRL2 amino acid sequence, for use in a method of prevention of or treatment for a muscle cell death-related disorder in a human or animal body by therapy. In certain embodiments, said modulator is identifiable by performing a method according to the first aspect. In certain embodiments, said modulator is identified by performing a method according to the first aspect. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a modulator of a Humanin GPCR, said receptor comprising an FPRL2 amino acid sequence, for use in a method of prevention of or treatment for a muscle cell proliferative disorder in a human or animal body by therapy. In certain embodiments, said modulator is an inverse agonist. In certain embodiments, said modulator is an antagonist. In certain embodiments, said muscle cell proliferative disorder selected from the group consisting of:

(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In certain embodiments, said animal is a mammal. In certain embodiments, said mammal is a horse, cow, sheep, pig, cat, dog, rabbit, mouse, rat, or non-human primate. More preferred of human or animal is human.

In a thirty-eighth aspect, the invention features a modulator of a Humanin GPCR, said receptor comprising an FPRL2 amino acid sequence, for use in a method of reducing cell death in the human or animal body by therapy. In certain embodiments, said modulator is identifiable by performing a method according to the first aspect. In certain embodiments, said modulator is identified by performing a method according to the first aspect.

The invention also features a modulator of a Humanin GPCR, said receptor comprising an FPRL2 amino acid sequence, for use in a method of prevention of or treatment for a cell death-related disorder in a human or animal body by therapy. In certain embodiments, said modulator is identifiable by performing a method according to the first aspect. In certain embodiments, said modulator is identified by performing a method according to the first aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 50%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 M in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a modulator of a Humanin GPCR, said receptor comprising an FPRL2 amino acid sequence, for use in a method of prevention of or treatment for a cell proliferative disorder in a human or animal body by therapy. In certain embodiments, said modulator is an inverse agonist. In certain embodiments, said modulator is an antagonist.

In certain embodiments, said animal is a mammal. In certain embodiments, said mammal is a horse, cow, sheep, pig, cat, dog, rabbit, mouse, rat, or non-human primate. More preferred of human or animal is human.

In a thirty-ninth aspect, the invention features a method of using a modulator of a Humanin GPCR, said receptor comprising an FPRL2 amino acid sequence, for the preparation of a medicament for the reduction of neuronal cell death. In certain embodiments, said method comprises performing a method according to the first aspect to thereby identify a modulator.

The invention also features a method of using a modulator of a Humanin GPCR, said receptor comprising an FPRL2 amino acid sequence, for the preparation of a medicament for the prevention or treatment of a neuronal cell death-related disorder. In certain embodiments, said method comprises performing a method according to the first aspect to thereby identify a modulator. In certain embodiments, said neuronal cell death-related disorder is selected from the group consisting of:
(a) Alzheimer's disease;
(b) Parkinson's disease;
(c) stroke;
(d) motor-neuron disease;
(e) learning or memory impairment;
(d) traumatic brain injury;
(e) spinal cord injury;
(f) peripheral neuropathy; and
(g) prion-associated disease.

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is neuroprotective.

In some embodiments, said modulator is an agonist with an $EC_{50}$ of less than 100 μM, of less than 10 μM, or of less than 1 μM. In some embodiments, said modulator is an agonist with an $EC_{50}$ of less than a value selected from the interval of 1 μM to 100 μM. In some embodiments, said modulator is an agonist with an $EC_{50}$ of less than a value selected from the interval of 1 μM to 10 μM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 μM, of less than 10 μM, or of less than 1 μM in said assay. In some embodiments, said modulator is an agonist with an $EC_{50}$ of less than 100 μM in said assay. In some embodiments, said modulator is an agonist with an $EC_{50}$ of less than 90 μM in said assay. In some embodiments, said modulator is an inverse agonist or antagonist with an EC50 of less than 80 μM in said assay. In some embodiments, said modulator is an agonist with an $EC_{50}$ of less than 70 μM in said assay. In some embodiments, said modulator is an agonist with an $EC_{50}$ of less than 60 μM in said assay. In some embodiments, said modulator is an agonist with an $EC_{50}$ of less than 50 μM in said assay. In some embodiments, said modulator is an agonist with an $EC_{50}$ of less than 40 μM in said assay. In some embodiments, said modulator is an agonist with an $EC_{50}$ of less than 30 μM in said assay. In some embodiments, said modulator is an agonist with an $EC_{50}$ of less than 20 μM in said assay. In some embodiments, said modulator is an agonist with an $EC_{50}$ of less than 10 μM in said assay. In some embodiments, said modulator is an agonist with an $EC_{50}$ of less than 9 μM in said assay. In some embodiments, said modulator is an agonist with an $EC_{50}$ of less than 8 μM in said assay. In some embodiments, said modulator is an agonist with an $EC_{50}$ of less than 7 μM in said assay. In some embodiments, said modulator is an agonist with an $EC_{50}$ of less than 6 μM in said assay. In some embodiments, said modulator is an agonist with an $EC_{50}$ of less than 5 μM in said assay. In some embodiments, said modulator is an agonist with an $EC_{50}$ of less than 4 μM in said assay. In some embodiments, said modulator is an agonist with an $EC_{50}$ of less than 3 μM in said assay. In some embodiments, said modulator is an agonist with an $EC_{50}$ of less than 2 μM in said assay. In some embodiments, said modulator is an agonist with an $EC_{50}$ of less than 2 μM in said assay. In some embodiments, said modulator is an agonist with an $EC_{50}$ in said assay of less than a value selected from the interval of 1 μM to 100 μM. In some embodiments, said modulator is an agonist with an $EC_{50}$ in said assay of less than a value selected from the interval of 1 μM to 10 μM.

In some embodiments, said modulator is an inverse agonist or an antagonist with an $IC_{50}$ of less than a value selected from the interval of 1 μM to 100 μM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 μM, less than 90 μM, less than 80 μM, less than 70 μM, less than 60 μM, less than 50 μM, less than 40 μM, less than 30 μM, less than 20 μM, or less than 10 μM. In some embodiments, said modulator is an inverse agonist or an antagonist with an $IC_{50}$ in said assay of less than a value selected from the interval of 1 μM to 10 μM. In certain embodiments, said modulator is an inverse agonist or an antagonist with an $IC_{50}$ in said assay of less than 10 μM, less than 9 µM, less than 8 µM, less than 7 µM, less than 6 µM, less than 5 µM, less than 4 µM, less than 3 µM, less than 2 µM, or less than 1 µM.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy (DSP).

The invention also features a method of using a modulator of a Humanin GPCR, said receptor comprising an FPRL2 amino acid sequence, for the preparation of a medicament for preventing or treating a neuronal cell proliferative disorder. In certain embodiments, said modulator is an inverse agonist. In certain embodiments, said modulator is an antagonist. In certain embodiments, said neuronal cell proliferative disorder is neuroblastoma. In other embodiments, said neuronal cell proliferative disorder is medulloblastoma.

In a fortieth aspect, the invention features a method of using a modulator of a Humanin GPCR, said receptor comprising an FPRL2 amino acid sequence, for the preparation of a medicament for the reduction of muscle cell death. In certain embodiments, said method comprises performing a method according to the first aspect to thereby identify a modulator.

The invention also features a method of using a modulator of a Humanin GPCR, said receptor comprising an FPRL2 amino acid sequence, for the preparation of a medicament for the prevention or treatment of a muscle cell death-related disorder. In certain embodiments, said method comprises performing a method according to the first aspect to thereby identify a modulator. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is myoprotective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried out using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a method of using a modulator of a Humanin GPCR, said receptor comprising an FPRL2 amino acid sequence, for the preparation of a medicament for the prevention or treatment of a muscle cell proliferative disorder. In certain embodiments, said modulator is an inverse agonist. In certain embodiments, said modulator is an antagonist. In certain embodiments, said muscle cell proliferative disorder is selected from the group consisting of:
(a) atherosclerosis;
(b) restenosis; and
(c) tumor-supportive angiogenesis.

In some embodiments, the muscle cell proliferative disorder is atherosclerosis. In some embodiments, the muscle cell proliferative disorder is restenosis. In some embodiments, the muscle cell proliferative disorder is tumor-supportive angiogenesis.

In a forty-first aspect, the invention features a method of using a modulator of a Humanin GPCR, said receptor comprising an FPRL2 amino acid sequence, for the preparation of a medicament for the reduction of cell death. In certain embodiments, said method comprises performing a method according to the first aspect to thereby identify a modulator.

The invention also features a method of using a modulator of a Humanin GPCR, said receptor comprising an FPRL2 amino acid sequence, for the preparation of a medicament for the prevention or treatment of a cell death-related disorder. In certain embodiments, said method comprises performing a method according to the first aspect to thereby identify a modulator. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said modulator is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof. In certain embodiments, said modulator is not a peptide. In certain embodiments, said modulator is according to the fourth aspect. In certain embodiments, said modulator is selected from the group consisting of agonist, partial agonist, inverse agonist, and antagonist. In certain preferred embodiments, said modulator is an agonist.

In certain embodiments, said modulator is selective for the GPCR.

In certain embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable modulator is further able to cross the blood-brain barrier.

In certain embodiments, said modulator is cell death-protective.

In some embodiments, said modulator is an agonist with an $EC_{50}$ of less than 100 µM, of less than 10 µM, or of less than 1 µM. In some embodiments, said modulator is an agonist with an $EC_{50}$ of less than a value selected from the interval of 1 µM to 100 µM. In some embodiments, said modulator is an agonist with an $EC_{50}$ of less than a value selected from the interval of 1 µM to 10 µM. In certain embodiments, said EC50 is in an assay selected from the group consisting of: GTPγS binding assay carried out with membrane from transfected CHO cells expressing recombinant Humanin GPCR polypeptide having the amino acid sequence of SEQ ID NO:2 or 6; melanophore assay carried out using transfected melanophores expressing recombinant Humanin GPCR polypeptide having the amino acid sequence of SEQ ID NO:2 or 6; and whole cell cAMP assay carried using transfected HEK293 cells expressing recombinant Humanin GPCR polypeptide having the amino acid sequence of SEQ ID NO:2 or 6. In some embodiments, said modulator is an agonist with an $EC_{50}$ of less than 100 µM, of less than 10 µM, or of less than 1 µM in said assay. In some embodiments, said modulator is an agonist with an $EC_{50}$ of less than 100 µM in said assay. In some embodiments, said modulator is an agonist with an $EC_{50}$ of less than 90 µM in said assay. In some embodiments, said modulator is an inverse agonist or antagonist with an EC50 of less than 80 µM in said assay. In some embodiments, said modulator is an agonist with an $EC_{50}$ of less than 70 µM in said assay. In some embodiments, said modulator is an agonist with an $EC_{50}$ of less than 60 µM in said assay. In some embodiments, said modulator is an agonist with an $EC_{50}$ of less than 50 µM in said assay. In some embodiments, said modulator is an agonist with an $EC_{50}$ of less than 40 µM in said assay. In some embodiments, said modulator is an agonist with an $EC_{50}$ of less than 30 µM in said assay. In some embodiments, said modulator is an agonist with an $EC_{50}$ of less than 20 µM in said assay. In some embodiments, said modulator is an agonist with an $EC_{50}$ of less than 10 µM in said assay. In some embodiments, said modulator is an agonist with an $EC_{50}$ of less than 9 µM in said assay. In some embodiments, said modulator is an agonist with an $EC_{50}$ of less than 8 µM in said assay. In some embodiments, said modulator is an agonist with an $EC_{50}$ of less than 7 µM in said assay. In some embodiments, said modulator is an agonist with an $EC_{50}$ of less than 6 µM in said assay. In some embodiments, said modulator is an agonist with an $EC_{50}$ of less than 5 µM in said assay. In some embodiments, said modulator is an agonist with an $EC_{50}$ of less than 4 µM in said assay. In some embodiments, said modulator is an agonist with an $EC_{50}$ of less than 3 µM in said assay. In some embodiments, said modulator is an agonist with an $EC_{50}$ of less than 2 µM in said assay. In some embodiments, said modulator is an agonist with an $EC_{50}$ of less than 1 µM in said assay. In some embodiments, said modulator is an agonist with an $EC_{50}$ in said assay of less than a value selected from the interval of 1 µM to 100 µM. In some embodiments, said modulator is an agonist with an $EC_{50}$ in said assay of less than a value selected from the interval of 1 µM to 10 µM.

In some embodiments, said modulator is an inverse agonist or an antagonist with an $IC_{50}$ of less than a value selected from the interval of 1 µM to 100 µM in an assay selected from the group consisting of GTPγS binding assay, melanophore assay, and whole cell cAMP assay, wherein said assay is carried out using transfected cells expressing recombinant Humanin GPCR polypeptide having the amino acid sequence of SEQ ID NO:12. In certain embodiments, said modulator is an inverse agonist or an antagonist with an $IC_{50}$ in said assay of less than 100 µM, less than 90 µM, less than 80 µM, less than 70 µM, less than 60 µM, less than 50 µM, less than 40 µM, less than 30 µM, less than 20 µM, or less than 10 µM. In some embodiments, said modulator is an inverse agonist or an antagonist with an $IC_{50}$ in said assay of less than a value selected from the interval of 1 µM to 10 µM. In certain embodiments, said modulator is an inverse agonist or an antagonist with an $IC_{50}$ in said assay of less than 10 µM, less than 9 µM, less than 8 µM, less than 7 µM, less than 6 µM, less than 5 µM, less than 4 µM, less than 3 µM, less than 2 µM, or less than 1 µM.

The invention also relates to a method of using a modulator of a Humanin GPCR, said receptor comprising an FPRL2 amino acid sequence, for the preparation of a medicament for the prevention or treatment of a cell proliferative disorder. In certain embodiments, said modulator is an inverse agonist. In certain embodiments, said modulator is an antagonist.

In a forty-second aspect, the invention features a method of preparing a pharmaceutical or physiologically acceptable composition comprising admixing a compound according to the second aspect and a carrier.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a forty-third aspect, the invention features a method of preparing a pharmaceutical or physiologically acceptable composition comprising admixing a compound according the third aspect and a carrier.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a forty-fourths aspect, the invention features a pharmaceutical or physiologically acceptable composition comprising, consisting essentially of, or consisting of a compound according to the second aspect.

In certain embodiments, said composition is pharmaceutical. In certain embodiments, said composition is physiologically acceptable.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a forty-fifth aspect, the invention features a pharmaceutical or physiologically acceptable composition comprising, consisting essentially of, or consisting of a compound according to the third aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a forty-sixth aspect, the invention features a method of modulating the activity of a Humanin GPCR, said receptor comprising an FPRL2 amino acid sequence, wherein said modulation is for reducing neuronal cell death in an individual in need of said modulation, comprising contacting said receptor with a therapeutically effective amount of a compound according to the second or third aspect or with a therapeutically effect amount of a pharmaceutical or physiologically acceptable composition according to the forty-fourth or forty-fifth aspect. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a forty-seventh aspect, the invention features a method of modulating the activity of a Humanin GPCR, said receptor comprising an FPRL2 amino acid sequence, wherein said modulation is for preventing or treating a neuronal cell death-related disorder in an individual in need of said modulation, comprising contacting said receptor with a therapeutically effective amount of a compound according to the second or third aspect or with a therapeutically effect amount of a pharmaceutical or physiologically acceptable composition according to the forty-fourth or forty-fifth aspect. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said neuronal cell death-related disorder is selected from the group consisting of:
  (a) Alzheimer's disease;
  (b) Parkinson's disease;
  (c) stroke;
  (d) motor-neuron disease;
  (e) learning or memory impairment;
  (f) traumatic brain injury;
  (g) spinal cord injury;
  (h) peripheral neuropathy; and
  (i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a forty-eighth aspect, the invention features a method of modulating the activity of a Humanin GPCR, said receptor comprising an FPRL2 amino acid sequence, wherein said modulation is for reducing muscle cell death in an individual in need of said modulation, comprising contacting said receptor with a therapeutically effective amount of a compound according to the second or third aspect or with a therapeutically effect amount of a pharmaceutical or physiologically acceptable composition according to the forty-fourth or forty-fifth aspect. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a forty-ninth aspect, the invention features a method of modulating the activity of a Humanin GPCR, said receptor comprising an FPRL2 amino acid sequence, wherein said modulation is for preventing or treating a muscle cell death-related disorder in an individual in need of said modulation, comprising contacting said receptor with a therapeutically effective amount of a compound according to the second or third aspect or with a therapeutically effect amount of a pharmaceutical or physiologically acceptable composition according to the forty-fourth or forty-fifth aspect. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fiftieth aspect, the invention features a method of modulating the activity of a Humanin GPCR, said receptor comprising an FPRL2 amino acid sequence, wherein said modulation is for reducing cell death in an individual in need of said modulation, comprising contacting said receptor with a therapeutically effective amount of a compound according to the second or third aspect or with a therapeutically effect amount of a pharmaceutical or physiologically acceptable composition according to the forty-fourth or forty-fifth aspect. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-first aspect, the invention features a method of modulating the activity of a Humanin GPCR, said receptor comprising an FPRL2 amino acid sequence, wherein said modulation is for preventing or treating a cell death-related disorder in an individual in need of said modulation, comprising contacting said receptor with a therapeutically effective amount of a compound according to the second or third aspect or with a therapeutically effective amount of a pharmaceutical or physiologically acceptable composition according to the forty-fourth or forty-fifth aspect. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 10%, at least 5%, at least 10%, at least 15%, at least 20%, at least 25%, at least 30%, at least 35%, at least 40%, or at least 45% relative to intraperitoneal administration. In some embodiments, said oral bioavailability is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-second aspect, the invention features a method of reducing neuronal cell death in an individual in need of said reducing, comprising contacting said receptor with a therapeutically effective amount of a compound according to the second or third aspect or with a therapeutically effective amount of a pharmaceutical or physiologically acceptable composition according to the forty-fourth or forty-fifth aspect with a Humanin GPCR, said receptor comprising an FPRL2 amino acid sequence. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifth-third aspect, the invention features a method of preventing or treating a neuronal cell death-related disorder in an individual in need of said reducing, comprising contacting said receptor with a therapeutically effective amount of a compound according to the second or third aspect or with a therapeutically effect amount of a pharmaceutical or physiologically acceptable composition according to the forty-fourth or forty-fifth aspect with a Humanin GPCR, said receptor comprising an FPRL2 amino acid sequence. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said neuronal cell death-related disorder is selected from the group consisting of:

(a) Alzheimer's disease;
(b) Parkinson's disease;
(c) stroke;
(d) motor-neuron disease;
(e) learning or memory impairment;
(f) traumatic brain injury;
(g) spinal cord injury;
(h) peripheral neuropathy; and
(i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-fourth aspect, the invention features a method of reducing muscle cell death in an individual in need of said reducing, comprising contacting said receptor with a therapeutically effective amount of a compound according to the second or third aspect or with a therapeutically effect amount of a pharmaceutical or physiologically acceptable composition according to the forty-fourth or forty-fifth aspect with a Humanin GPCR, said receptor comprising an FPRL2 amino acid sequence. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-fifth aspect, the invention features a method of preventing or treating a muscle cell death-related disorder in an individual in need of said reducing, comprising contacting said receptor with a therapeutically effective amount of a compound according to the second or third aspect or with a therapeutically effect amount of a pharmaceutical or physiologically acceptable composition according to the forty-fourth or forty-fifth aspect with a Humanin GPCR, said receptor comprising an FPRL2 amino acid sequence. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-sixth aspect, the invention features a method of reducing cell death in an individual in need of said reducing, comprising contacting said receptor with a therapeutically effective amount of a compound according to the second or third aspect or with a therapeutically effect amount of a pharmaceutical or physiologically acceptable composition according to the forty-fourth or forty-fifth aspect with a Humanin GPCR, said receptor comprising an FPRL2 amino acid sequence. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human-mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-seventh aspect, the invention features a method of preventing or treating a cell death-related disorder in an individual in need of said reducing, comprising contacting said receptor with a therapeutically effective amount of a compound according to the second or third aspect or with a therapeutically effect amount of a pharmaceutical or physiologically acceptable composition according to the forty-fourth or forty-fifth aspect with a Humanin GPCR, said receptor comprising an FPRL2 amino acid sequence. In certain embodiments, said contacting is with a therapeutically effective amount of a compound according to the second aspect. In certain embodiments, said contacting is with a therapeutically effective amount of a compound according to the third aspect. In certain embodiments, said contacting is with a therapeutically effective amount of a pharmaceutical or physiologically acceptable composition according to the forty-fourth aspect. In certain embodiments, said contacting is with a therapeutically effective amount of a pharmaceutical or physiologically acceptable composition according to the forty-fifth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-eighth aspect, the invention features a method of reducing neuronal cell death comprising providing or administering to an individual in need of said reducing a compound according to the second or third aspect or with a therapeutically effective amount of a pharmaceutical or physiologically acceptable composition according to the forty-fourth or forty-fifth aspect. In certain embodiments, said providing or administering a compound is providing or administering a compound according to the second aspect. In certain embodiments, said providing or administering a compound is providing or administering a compound according to the third aspect. In certain embodiments, said providing or administering a pharmaceutical or physiologically acceptable composition is providing or administering a pharmaceutical or physiologically acceptable composition according to the forty-fourth aspect. In certain embodiments, said providing or administering a pharmaceutical or physiologically acceptable composition is providing or administering a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a fifty-ninth aspect, the invention features a method of treating a neuronal cell death-related disorder comprising providing or administering to an individual in need of said treating or preventing a compound according to the second or third aspect or with a therapeutically effective amount of a pharmaceutical or physiologically acceptable composition according to the forty-fourth or forty-fifth aspect. In certain embodiments, said providing or administering a compound is providing or administering a compound according to the second aspect. In certain embodiments, said providing or administering a compound is providing or administering a compound according to the third aspect. In certain embodiments, said providing or administering a pharmaceutical or physiologically acceptable composition is providing or administering a pharmaceutical or physiologically acceptable composition according to the forty-fourth aspect. In certain embodiments, said providing or administering a pharmaceutical or physiologically acceptable composition is providing or administering a pharmaceutical or physiologically acceptable composition according to the forty-fifth aspect. In certain embodiments, said neuronal cell death-related disorder is selected from the group consisting of:
(a) Alzheimer's disease;
(b) Parkinson's disease;
(c) stroke;
(d) motor-neuron disease;
(e) learning or memory impairment;
(f) traumatic brain injury;
(g) spinal cord injury;
(h) peripheral neuropathy; and
(i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a sixtieth aspect, the invention features a method of reducing muscle cell death comprising providing or administering to an individual in need of said reducing a compound according to the second or third aspect or with a therapeutically effective amount of a pharmaceutical or physiologically acceptable composition according to the forty-fourth or forty-fifth aspect. In certain embodiments, said providing or administering a compound is providing or administering a compound according to the second aspect. In certain embodiments, said providing or administering a compound is providing or administering a compound according to the third aspect. In certain embodiments, said providing or administering a pharmaceutical or physiologically acceptable composition is providing or administering a pharmaceutical or physiologically acceptable composition according to the forty-fourth aspect. In certain embodiments, said providing or administering a pharmaceutical or physiologically acceptable composition is providing or administering a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a sixty-first aspect, the invention features a method of treating a muscle cell death-related disorder comprising providing or administering to an individual in need of said treating or preventing a compound according to the second or third aspect or with a therapeutically effective amount of a pharmaceutical or physiologically acceptable composition according to the forty-fourth or forty-fifth aspect. In certain embodiments, said providing or administering a compound is providing or administering a compound according to the second aspect. In certain embodiments, said providing or administering a compound is providing or administering a compound according to the third aspect. In certain embodiments, said providing or administering a pharmaceutical or physiologically acceptable composition is providing or administering a pharmaceutical or physiologically acceptable composition according to the forty-fourth aspect. In certain embodiments, said providing or administering a pharmaceutical or physiologically acceptable composition is providing or administering a pharmaceutical or physiologically acceptable composition according to the forty-fifth aspect. In certain embodiments, said muscle cell death-related disorder is selected from the group consisting of:
(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a sixty-second aspect, the invention features a method of reducing cell death comprising providing or administering to an individual in need of said reducing a compound according to the second or third aspect or with a therapeutically effective amount of a pharmaceutical or physiologically acceptable composition according to the forty-fourth or forty-fifth aspect. In certain embodiments, said providing or administering a compound is providing or administering a compound according to the second aspect. In certain embodiments, said providing or administering a compound is providing or administering a compound according to the third aspect. In certain embodiments, said providing or administering a pharmaceutical or physiologically acceptable composition is providing or administering a pharmaceutical or physiologically acceptable composition according to the forty-fourth aspect. In certain embodiments, said providing or administering a pharmaceutical or physiologically acceptable composition is providing or administering a pharmaceutical or physiologically acceptable composition according to the forty-fifth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a sixty-third aspect, the invention features a method of treating a cell death-related disorder comprising providing or administering to an individual in need of said treating or preventing a compound according to the second or third aspect or with a therapeutically effective amount of a pharmaceutical or physiologically acceptable composition according to the forty-fourth or forty-fifth aspect. In certain embodiments, said providing or administering a compound is providing or administering a compound according to the second aspect. In certain embodiments, said providing or administering a compound is providing or administering a compound according to the third aspect. In certain embodiments, said providing or administering a pharmaceutical or physiologically acceptable composition is providing or administering a pharmaceutical or physiologically acceptable composition according to the forty-fourth aspect. In certain embodiments, said providing or administering a pharmaceutical or physiologically acceptable composition is providing or administering a pharmaceutical or physiologically acceptable composition according to the forty-fifth aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said individual is a mammal. In certain embodiments, said individual is a non-human mammal. In certain embodiments, said mammal is a horse, cow, sheep, pig, cat, dog, rabbit, mouse, rat, non-human primate or human. In certain embodiments, said mammal is a mouse, rat, non-human primate, or human. Most preferred is human.

In a sixty-fourth aspect, the invention features a compound according to the second or third aspect for use in a method of treatment of the human or animal body by therapy. In certain embodiments, said compound is according to the second aspect. In certain embodiments, said compound is according to the third aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a sixty-fifth aspect, the invention features a compound according to the second or third aspect for use in a method of reducing neuronal cell death in the human or animal body by therapy. In certain embodiments, said compound is according to the second aspect. In certain embodiments, said compound is according to the third aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a sixty-sixth aspect, the invention features a compound according to the second or third aspect for use in a method of prevention or treatment for a neuronal cell death-related disorder in the human or animal body by therapy. In certain embodiments, said compound is according to the second aspect. In certain embodiments, said compound is according to the third aspect. In certain embodiments, said neuronal cell death-related disorder is selected from the group consisting of:

(a) Alzheimer's disease;
(b) Parkinson's disease;
(c) stroke;
(d) motor-neuron disease;
(e) learning or memory impairment;
(f) traumatic brain injury;
(g) spinal cord injury;
(h) peripheral neuropathy; and
(i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited, to diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a sixty-seventh aspect, the invention features a compound according to the second or third aspect for use in a method of prevention or treatment of muscle cell death in the human or animal body by therapy. In certain embodiments, said compound is according to the second aspect. In certain embodiments, said compound is according to the third aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a sixty-eighth aspect, the invention features a compound according to the second or third aspect for use in a method of prevention or treatment for a muscle cell death-related disorder in the human or animal body by therapy. In certain embodiments, said compound is according to the second aspect. In certain embodiments, said compound is according to the third aspect. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a sixty-ninth aspect, the invention features a compound according to the second or third aspect for use in a method of prevention or treatment of cell death in the human or animal body by therapy. In certain embodiments, said compound is according to the second aspect. In certain embodiments, said compound is according to the third aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a seventieth aspect, the invention features a compound according to the second or third aspect for use in a method of prevention or treatment for a cell death-related disorder in the human or animal body by therapy. In certain embodiments, said compound is according to the second aspect. In certain embodiments, said compound is according to the third aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In certain embodiments, said animal is a mammal. In certain embodiments, said mammal is a horse, cow, sheep, pig, cat, dog, rabbit, mouse, rat, or non-human primate. More preferred of human or animal is human.

In a seventy-first aspect, the invention features a method of using a compound according to the second or third aspect for the preparation of a medicament for the reduction of neuronal cell death. In certain embodiments, said compound is according to the second aspect. In certain embodiments, said compound is according to the third aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-second aspect, the invention features a method of using a compound according to the second or third aspect for the preparation of a medicament for the prevention of or treatment of a neuronal cell death-related disorder. In certain embodiments, said compound is according to the second aspect. In certain embodiments, said compound is according to the third aspect. In certain embodiments, said neuronal cell death-related disorder is selected from the group consisting of:

(a) Alzheimer's disease;
(b) Parkinson's disease;

(c) stroke;
(d) motor-neuron disease;
(e) learning or memory impairment;
(f) traumatic brain injury;
(g) spinal cord injury;
(h) peripheral neuropathy; and
(i) prion-associated disease.

In some embodiments, Alzheimer's disease encompasses mild cognitive impairment (MCI).

Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy (DSP).

In some embodiments, the neuronal cell death-related disorder is Alzheimer's disease. In some embodiments, the neuronal cell death-related disorder is Parkinson's disease. In some embodiments, the neuronal cell death-related disorder is stroke. In some embodiments, the neuronal cell death-related disorder is motor-neuron disease. In some embodiments, the neuronal cell death-related disorder is learning or memory impairment. In some embodiments, the neuronal cell death-related disorder is traumatic brain injury. In some embodiments, the neuronal cell death-related disorder is spinal cord injury. In some embodiments, the neuronal cell death-related disorder is peripheral neuropathy. In some embodiments, the neuronal cell death-related disorder is prion-associated disease.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-third aspect, the invention features a method of using a compound according to the second or third aspect for the preparation of a medicament for the reduction of muscle cell death. In certain embodiments, said compound is according to the second aspect. In certain embodiments, said compound is according to the third aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-fourth aspect, the invention features a method of using a compound according to the second or third aspect for the preparation of a medicament for the prevention of or treatment of a muscle cell death-related disorder. In certain embodiments, said compound is according to the second aspect. In certain embodiments, said compound is according to the third aspect. In certain embodiments, said muscle cell death-related disorder is selected from the group consisting of:

(a) cerebral amyloid beta-protein angiopathy;
(b) myocardial infarction; and
(c) congestive heart failure.

In some embodiments, the muscle cell death-related disorder is cerebral amyloid beta-protein angiopathy. In some embodiments, the muscle cell death-related disorder is myocardial infarction. In some embodiments, the muscle cell death-related disorder is congestive heart failure.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-fifth aspect, the invention features a method of using a compound according to the second or third aspect for the preparation of a medicament for the reduction of cell death. In certain embodiments, said compound is according to the second aspect. In certain embodiments, said compound is according to the third aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-sixth aspect, the invention features a method of using a compound according to the second or third aspect for the preparation of a medicament for the prevention of or treatment of a cell death-related disorder. In certain embodiments, said compound is according to the second aspect. In certain embodiments, said compound is according to the third aspect. In certain embodiments, said cell resides in or derives from a tissue that expresses human FPRL2. In certain embodiments, said tissue expressing human FPRL2 is selected from the group consisting of sciatic nerve, anterior hippocampus, whole brain, hippocampus, substantia nigra, spleen, heart, lung, pancreas, bone, and ovary.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-seventh aspect, the invention features a method of modulating a Humanin GPCR, said receptor comprising an FPRL2 amino acid sequence, comprising contacting said receptor with a compound according to the second or third aspect or with a pharmaceutical or physiologically acceptable composition according to the forty-fourth or forty-fifth aspect. In certain embodiments, said contacting is with a compound according to the second aspect. In certain embodiments, said contacting is with a compound according to the third aspect. In certain embodiments, said contacting is with a pharmaceutical or physiologically acceptable composition according to the forty-fourth aspect. In certain embodiments, said contacting is with a pharmaceutical or physiologically acceptable composition according to the forty-fifth aspect.

In certain embodiments, said compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 20%, at least 25%, at least 30%, at least 35%, at least 40%, or at least 45% relative to intravenous administration.

In certain embodiments, said orally bioavailable compound is further able to cross the blood-brain barrier.

In a seventy-eighth aspect, the invention features a method of identifying whether a candidate compound binds to a Humanin GPCR, said receptor comprising an FPRL2 amino acid sequence, comprising the steps of:
(a) contacting the receptor with a detectably labeled known ligand of the GPCR in the presence or absence of the candidate compound; and
(b) determining whether the binding of said labeled ligand is inhibited in the presence of the candidate compound;

wherein said inhibition is indicative of the candidate compound binding to a Humanin GPCR.

In certain embodiments, the Humanin GPCR is recombinant. In certain embodiments, said contacting comprises contacting with a host cell or with membrane of a host cell that expresses the GPCR, wherein said host cell comprises an expression vector comprising a polynucleotide encoding the receptor.

The invention also relates to a method of determining whether a candidate compound binds to a Humanin GPCR, comprising the steps of:
(a) culturing Humanin GPCR-expressing host cells under conditions that would allow expression of a recombinant Humanin GPCR, said host cells being transfected with an expression vector comprising a polynucleotide encoding said recombinant Humanin GPCR comprising an FPRL2 amino acid sequence;
(b) exposing a first population of Humanin GPCR-expressing cells of step (a) to a detectably labeled known ligand of said Humanin GPCR;
(c) exposing a second population of Humanin GPCR-expressing cells of step (a) to the compound and the labeled known ligand of said Humanin GPCR of step (b);
(d) determining the binding of the labeled known ligand of said Humanin GPCR-expressing cells of step (b) and step (c); and
(e) comparing the binding of the labeled known ligand to said Humanin GPCR to the Humanin GPCR-expressing cells of step (b) and step (c);

wherein inhibition of binding of the labeled known ligand of said Humanin GPCR in the presence of the compound is indicative of the compound binding to a Humanin GPCR.

The invention also relates to a method of determining whether a candidate compound binds to a Humanin GPCR, comprising the steps of:
(a) culturing Humanin GPCR-expressing host cells under conditions that would allow expression of a recombinant Humanin GPCR, said host cells being transfected with an expression vector comprising a polynucleotide encoding said recombinant Humanin GPCR comprising an FPRL2 amino acid sequence;
(b) preparing membrane from the Humanin GPCR-expressing cells of step (a);
(c) exposing a first population of the membrane preparation of step (b) to a detectably labeled known ligand of said Humanin GPCR of step (b);
(d) exposing a second population of the membrane preparation of step (b) to the candidate compound and the labeled known ligand of said Humanin GPCR;
(e) determining the binding of the labeled known ligand of said Humanin GPCR to the membrane preparations of step (c) and step (d); and
(f) comparing the binding of the labeled known ligand of said Humanin GPCR to the membrane preparations of step (c) and step (d);

wherein inhibition of binding of the labeled known ligand of said Humanin GPCR in the presence of the compound is indicative of the compound binding to a Humanin GPCR.

In some embodiments, the FPRL2 amino acid sequence is the amino acid sequence of SEQ ID NO:2. In some embodiments, the FPRL2 amino acid sequence is a variant of the amino acid sequence of SEQ ID NO:2. In some embodiments, said variant of the amino acid sequence of SEQ ID NO:2 is an allelic variant or mammalian ortholog of said amino acid sequence. In some embodiments, said variant of the amino acid sequence of SEQ ID NO:2 is a non-endogenous, constitutively activated mutant of said amino acid sequence or of an allelic variant or mammalian ortholog of said amino acid sequence. In certain embodiments, said non-endogenous, constitutively activated mutant is the amino acid sequence of SEQ ID NO:12. In certain embodiments, said variant of the amino acid sequence of SEQ ID NO:2 is a biologically active fragment of said amino acid sequence or of an allelic variant or mammalian ortholog of said amino acid sequence. In certain embodiments, said biologically active fragment is amino acids 2-353 of the amino acid sequence of SEQ HD NO:2 or of an allelic variant or mammalian ortholog of said amino acid sequence. In certain embodiments, said variant of the amino acid sequence of SEQ ID NO:2 is at least about 75%, at least about 80%, at least about 85%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2. In certain embodiments, said variant of the amino acid sequence of SEQ ID NO:2 is at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2.

In certain embodiments, said membrane preparation is made by homogenization of the cells with a Brinkman Polytron™. In certain embodiments, said membrane preparation is made by homogenization with 3 bursts of 10-20 sec duration each of said polytron.

In certain embodiments, said candidate compound is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof.

In certain embodiments, said candidate compound is not a peptide.

In certain embodiments, said known ligand is Humanin.

In certain embodiments, said known ligand is a peptide analog or derivative of Humanin.

In certain embodiments, said known ligand is [Gly14]-Humanin.

In certain embodiments, said known ligand is Compound 1.

In certain embodiments, said known ligand is a compound according to the second aspect.

In certain embodiments, said known ligand is a compound according to the third aspect.

In certain embodiments, said known ligand is a modulator according to the fourth aspect.

In certain embodiments, said known ligand is an antibody specific for the GPCR, or a derivative of the antibody. In some embodiments, said derivative of the antibody is an antigen-binding fragment of the antibody.

In certain embodiments, said label is selected from the group consisting of:
  (a) radioisotope;
  (b) enzyme; and
  (c) fluorophore.

In certain embodiments, said label is a radioisotope. In certain embodiments, said label is selected from the group consisting of $^3$H, $^{14}$C, $^{35}$S, and $^{125}$I.

Radiolabeled Humanin or [Gly14]-Humanin can be chemically synthesized using techniques known in the art [See, e.g., Creighton, 1983 Proteins. New York, N.Y.: W.H. Freeman and Company; and Hunkapiller et al., Nature (1984) 310:105-11]. Radioisotope is introduced through radiolabled amino acid. In certain embodiments, said radiolabled amino acid is $^3$H-arginine or $^{14}$C-arginine.

In certain embodiments, said presence of said radiolabeled Humanin or [Gly14]-Humanin is at a concentration of about 0.1 ΣM to about 1.5 µM.

Compound 1 can be radiolabelled using techniques known in the art, infra. In certain embodiments, Compound 1 is radiolabelled with $^3$H or $^{14}$C.

In certain embodiments, said presence of said radiolabelled Compound 1 is at a concentration of about 1 µM to about 15 µM.

In other embodiments, said method further comprises the step of comparing the level of inhibition of binding of a labeled first known ligand by the candidate compound to a second level of inhibition of binding of said labeled first known ligand by a second ligand known to bind to the GPCR.

In a seventy-ninth aspect, the invention features a method for detecting ligands that bind to a Humanin GPCR, said receptor comprising an FPRL2 amino acid sequence, comprising the steps of:
  contacting a test ligand with a host cell or with membrane of a host cell that expresses said receptor, under conditions which permit interaction between said receptor and said test ligand; and detecting a ligand bound to said receptor.

In some embodiments, the FPRL2 amino acid sequence is the amino acid sequence of SEQ ID NO:2. In some embodiments, the FPRL2 amino acid sequence is a variant of the amino acid sequence of SEQ ID NO:2. In some embodiments, said variant of the amino acid sequence of SEQ ID NO:2 is an allelic variant or mammalian ortholog of said amino acid sequence. In some embodiments, said variant of the amino acid sequence of SEQ ID NO:2 is a non-endogenous, constitutively activated mutant of said amino acid sequence or of an allelic variant or mammalian ortholog of said amino acid sequence. In certain embodiments, said non-endogenous, constitutively activated mutant is the amino acid sequence of SEQ ID NO:12. In certain embodiments, said variant of the amino acid sequence of SEQ ID NO:2 is a biologically active fragment of said amino acid sequence or of an allelic variant or mammalian ortholog of said amino acid sequence. In certain embodiments, said biologically active fragment is amino acids 2-353 of the amino acid sequence of SEQ ID NO:2 or of an allelic variant or mammalian ortholog of said amino acid sequence. In certain embodiments, said variant of the amino acid sequence of SEQ ID NO:2 is at least about 75%, at least about 80%, at least about 85%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2. In certain embodiments, said variant of the amino acid sequence of SEQ ID NO:2 is at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2.

In certain embodiments, the Humanin GPCR is recombinant. In certain embodiments, said contacting comprises contacting with a host cell or with membrane of a host cell that expresses the GPCR, wherein said host cell comprises an expression vector comprising a polynucleotide encoding the receptor.

In certain embodiments, said candidate compound is not Humanin or an allelic variant, homologue, ortholog, or peptide analog or derivative thereof, or the peptide WKYMVm (SEQ ID NO: 16) or a peptide analog or derivative thereof. In certain embodiments, the modulator is not an antibody or derivative thereof.

In certain embodiments, said test ligand is not a peptide.

In certain embodiments, said membrane preparation is made by homogenization of the cells with a Brinkman Polytron™. In certain embodiments, said membrane preparation is made by homogenization with 3 bursts of 10-20 sec duration each of said polytron.

In certain embodiments, said test ligand is labeled. In certain embodiments, said label is a radioisotope. In certain embodiments, said label is selected from the group consisting of $^3$H, $^{14}$C, $^{35}$S and $^{125}$I.

Applicant reserves the right to exclude any one or more candidate compounds from any of the embodiments of the invention. Applicant also reserves the right to exclude any one or more modulators from any of the embodiments of the invention, including but not limited to Humanin or any peptide analog or derivative thereof. Applicant further reserves the right to exclude any polynucleotide or polypeptide from any of the embodiments of the invention. Applicant additionally reserves the right to exclude any cell death-related disorder or any disorder of neuronal cell death or muscle cell death from any of the embodiments of the invention.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

Modifications and extension of the disclosed inventions that are within the purview of the skilled artisan are encompassed within the above disclosure and the claims that follow.

BRIEF DESCRIPTION OF THE DRAWINGS

FIG. 1 depicts results from a primary screen of candidate compounds against a "target receptor" which is a Gsα Fusion Protein construct of an endogenous, constitutively active Gs-coupled GPCR. Results for "Compound A" are provided in well A2. Results for "Compound "B" are provided in well G9. (See, Example 7.)

Inspection of the plot indicates that the expression of human FPRL2 encompasses brain, peripheral nerve, and heart. Expression within brain encompasses anterior hippocampus, hippocampus, and substantia nigra. Expression within peripheral nerve encompasses sciatic nerve. Significant FPRL2 expression is also observed, e.g., for spleen, lung, pancreas, bone, and ovary. (See, Example 9.)

Figure 3:
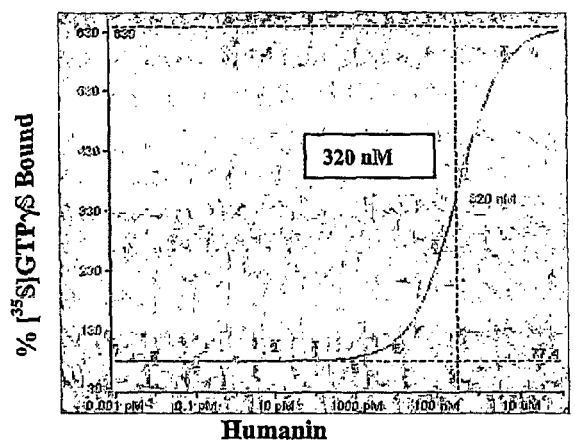
Figure 3:
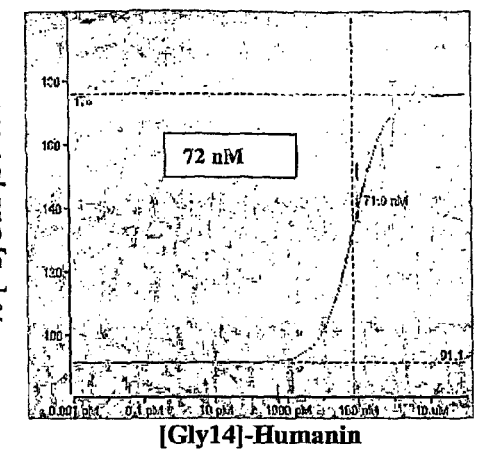
Figure 3:
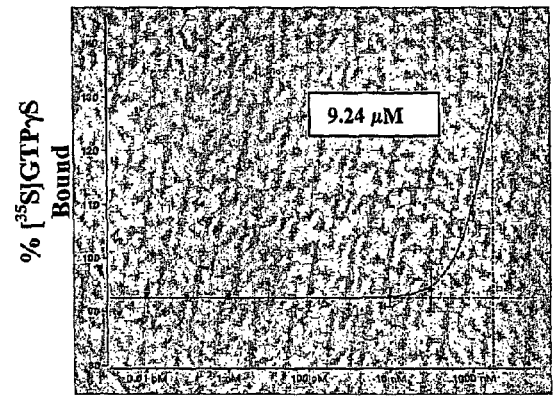
Figure 3:
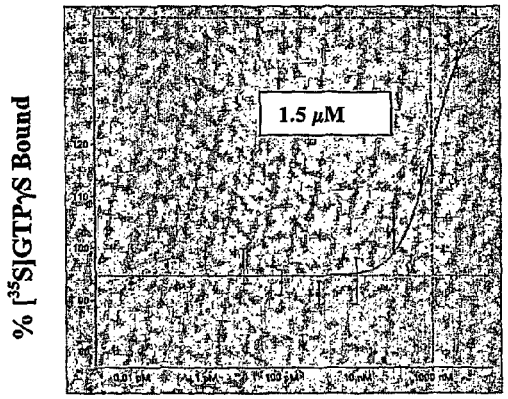
Figure 3:
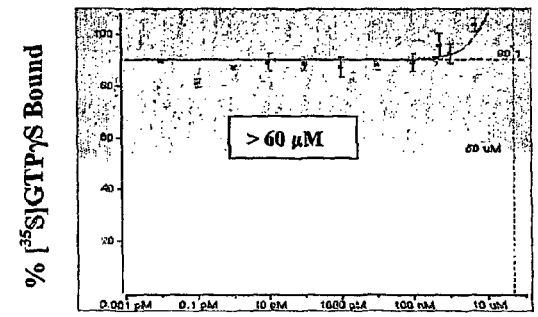
Figure 3:
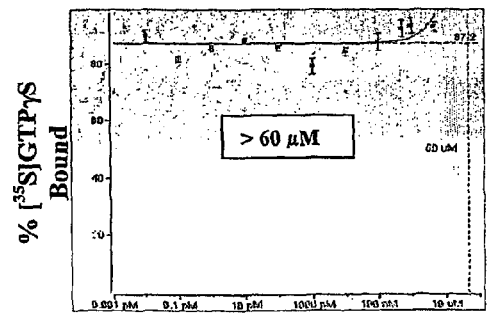

FIG. 3. Analysis of Humanin and [Gly14]-Humanin promoted [$^{35}$S]GTPγS binding was carried out for human FPRL2 (panel A), FPRL1 (panel B), and FPR (panel C). The EC50 of Humanin at FPRL2 is about 320 nm and that of [Gly14]-Humanin is about 72 nm. These values are more than an order of magnitude lower than the corresponding values at FPRL1, which are about 9.24 μM for Humanin and about 1.5 μM for [Gly14]-Humanin. Neither Humanin nor [Gly14]-Humanin evidence significant activity at FPR up to a dose of 10 μM. Humanin and [Gly14]-Humanin therefore are robust and selective agonists for FPRL2. (See, Example 10.)

Figure 4:
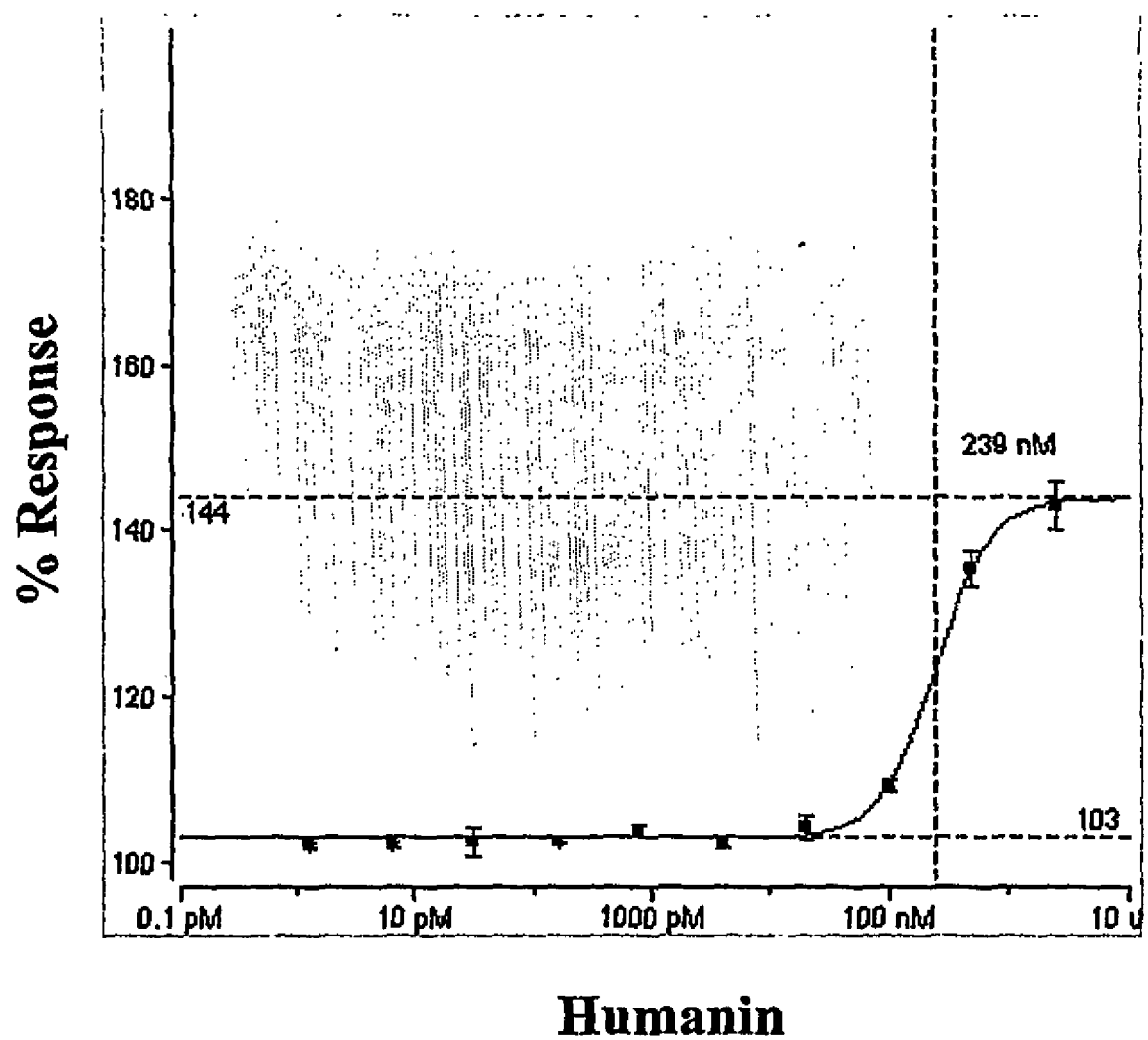

FIG. 4. In melanophores, human FPRL2 couples to Gi in a dose-dependent manner in response to Humanin. The EC50 of Humanin promoted pigment aggregation in melanophore (Gi coupling) is about 239 nM. (See, Example 11.)

FIG. 5. The activity of Compound 1 ("Cmpd 1" in Table 1) at human FPRL2, FPRL1 and FPR was determined by [$^{35}$S] GTPγS binding assay and by melanophore assay. Compound 1 was found to be a robust and selective agonist of FPRL2. (See, Example 21.)

FIG. 6. The activity of Humanin, [Gly14]-Humanin, and Compound 1 at human FPRL2 and FPRL1 was determined by whole cell adenylate cyclase assay. Whereas Human and [Gly14]-Humanin are agonists of both FPRL2 and FPRL1 (panel A), Compound 1 is selectively an agonist of FPRL2 (panel B). (See, Example 21.)

FIG. 7. The pertussis sensitivity of Humanin signaling through human FPRL2 was determined by adenylate cyclase assay. The pertussis toxin sensitivity of Compound 1 signaling through human FPRL2 was determined similarly. The inhibition of cAMP mediated either by Humanin (panel A) or by Compound 1 (panel B) is pertussis sensitive, indicating that FPRL2 couples to a pertussis-sensitive G protein in response to Humanin or Compound 1. (See, Example 22.)

FIG. 8. The capacity of FPRL2 to couple to Gαl 6 in response to Humanin, [Gly14]-Humanin, or Compound 1 was determined by IP$_3$ assay. A dose-dependent elevation of the level of intracellular IP$_3$ by Humanin (panel A), [Gly14]-Humanin (panel B), and Compound 1 (panel C) was observed, indicating that FPRL2 can signal through Gα16 in response to either Humanin or Compound 1. (See, Example 23.)

FIG. 9. The expression of FPRL2 and FPRL1 by the human neuroblastoma cell line SH-SY5Y, before or after differentiation by brain-derived nerve growth factor (BDNF), was determined. FPRL2 mRNA is detectable both in undifferentiated and differentiated SH-SY5Y cells, whereas FPRL1 mRNA is detectable in neither. (See, Example 24.)

FIG. 10. The capacity of Humanin or Compound 1 to inhibit the cell death of serum-deprived differentiated SH-SY5Y cells was determined by LDH assay (panel A) or Trypan Blue staining (panel B). Both Humanin and Compound 1 inhibit cell death of serum-deprived SH-SY5Y cells. (See, Example 25.)

FIG. 11. The capacity of Humanin or Compound 1 to inhibit the cell death of primary mouse cortical neurons induced by anti-APP mAb 22C11 was determined. In panel A is a photograph of a 5 day culture of primary mouse cortical neurons. Humanin and Compound 1 protect primary mouse cortical neurons from cell death induced by anti-APP mAb 22C11 (panel B). (See, Example 26.)

FIG. 12. The capacity of Humanin or Compound 1 to inhibit the Aβ-induced cell death of differentiated SH-SY5Y cells was determined. Humanin and Compound 1 protect differentiated SH-SY5Y cells from Aβ-induced cell death. (See, Example 27.)

FIG. 13. An outline of an hypoxia/reoxygenation in vitro model is presented.

FIG. 14. The expression of FPRL2 in Alzheimer's disease brain relative to that in non-Alzheimer's disease brain was determined by immunohistochemistry. Expression of FPRL2 by the Alzheimer's disease brain sample is up-regulated relative to that in the non-Alzheimer's disease brain sample.

DETAILED DESCRIPTION

Definitions

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate an intracelluar response when they bind to the receptor. In some embodiments, AGONISTS are those materials not previously known to activate the intracellular response when they bind to the receptor (e.g. to enhance GTPγS binding to membranes or to lower intracellular cAMP level). In some embodiments, AGONISTS are those materials not previously known to be neuroprotective or myoprotective when they bind to the receptor.

ALLOSTERIC MODULATORS shall mean materials (e.g., ligands, candidate compounds) that affect the functional activity of the receptor but which do not inhibit the endogenous ligand from binding to the receptor. Allosteric modulators include inverse agonists, partial agonists and agonists.

ALZHEIMER'S DISEASE is a progressive neurodegenerative disease characterized by significant loss of function in more than one cognitive domain and often accompanied by changes in behavior or personality. Alzheimer's disease is the most common cause of dementia. The beta-amyloid peptide (Aβ) is believed to play a central role in the pathology of Alzheimer's disease.

AMINO ACID ABBREVIATIONS used herein are set out in Table A:

TABLE A

| ALANINE | ALA | A |
|---|---|---|
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONISTS shall mean materials (e.g., ligands, candidate compounds) that competitively bind to the receptor at the same site as the agonists but which do not activate an intracellular response, and can thereby inhibit the intracellular responses elicited by agonists. ANTAGONISTS do not diminish the baseline intracellular response in the absence of an agonist. In some embodiments, ANTAGONISTS are those materials not previously known to compete with an agonist to inhibit the cellular response when they bind to the receptor, e.g. wherein the cellular response is GTPγS binding to membranes or to the lowering of intracellular cAMP level.

ANTIBODIES are intended herein to encompass monoclonal antibodies and polyclonal antibodies. Antibodies are further intended to encompass IgG, IgA, IgD, IgE, and IgM. Antibodies include whole antibodies, including single-chain whole antibodies, and antigen binding fragments thereof, including Fab, Fab', F(ab)2 and F(ab')2. Antibodies may be from any animal origin. Preferably, antibodies are human, murine, rabbit, goat, guinea pig, hamster, camel, donkey, sheep, horse or chicken. Preferably antibodies have binding affinities with a dissociation constant or Kd value less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M and $10^{-15}$M. Antibodies of the present invention may be prepared by any suitable method known in the art. Derivatives of antibodies are intended to encompass, but not be limited to, antigen-binding fragments.

BIOLOGICALLY ACTIVE FRAGMENT of a GPCR polypeptide or amino acid sequence shall mean a fragment of the polypeptide or amino acid sequence having structural and biochemical functions of a naturally occurring GPCR. In certain embodiments, the biologically active fragment couples to a G protein. In certain embodiments, the biologically active fragment binds to Humanin.

CANDIDATE COMPOUND shall mean a molecule (for example, and not limitation, a chemical compound) that is amenable to a screening technique.

CEREBRAL AMYLOID BETA-PROTEIN ANGIOPATHY or CEREBRAL AMYLOID ANGIOPATHY (CAA) is a key feature of Alzheimer's disease and related disorders. CAA is a disease of small blood vessels in the brain in which deposits of amyloid protein in the vessel walls may lead to stroke, brain hemorrhage, or dementia. Vascular amyloid deposition leads to degeneration of the vessel wall and aneurysm formation, and may be responsible for 10 to 15% of hemorrhagic strokes in the elderly.

Chemical Group, Moiety or Radical:

The term "$C_{1-5}$ acyl" denotes a $C_{1-4}$ alkyl radical attached to a carbonyl wherein the definition of alkyl has the same definition as described herein; some examples include but not limited to, acetyl, propionyl, n-butyryl, iso-butyryl, 2-methyl-butyryl, 2,2-dimethyl-propionyl (i.e., pivaloyl), 3-methyl-butyryl and the like.

The term "$C_{1-5}$ acyloxy" denotes an $C_{1-5}$ acyl radical attached to an oxygen atom wherein $C_{1-5}$ acyl has the same definition has described herein; some examples include but not limited to acetyloxy, propionyloxy, n-butyryloxy, iso-butyryloxy, 2-methylbutyryloxy, 2,2-dimethylpropionyloxy (i.e., pivaloyloxy), 3-methylbutyryloxy, and the like.

The term "$C_{2-6}$ alkenyl" denotes a radical containing 2 to 6 carbons wherein at least one carbon-carbon double bond is present, some embodiments are 2 to 3 carbons, and some embodiments have 2 carbons. Both E and Z isomers are embraced by the term "alkenyl." Furthermore, the term "alkenyl" includes di-enes. Accordingly, if more than one double bond is present, then the bonds may be all E or Z or a mixtures of E and Z. Examples of an alkenyl include vinyl, propenyl, allyl, isopropenyl, 2-methyl-propenyl1-methyl-propenyl, but-1-enyl, but-2-enyl, but-3-enyl, buta-1,3-dienyl, and the like.

The term "$C_{1-4}$ alkoxy" denotes an alkyl radical, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-6}$ alkyl" denotes a straight or branched carbon radical containing the number of carbons as indicated, for examples, in some embodiments, alkyl is a "$C_{1-4}$ alkyl" and the group contains 1 to 4 carbons, in still other embodiments, alkyl is a "$C_{2-6}$ alkyl" and the group contains 2 to 6 carbons. In some embodiments alkyl contains 1 to 3 carbons, some embodiments contain 1 to 2 carbons, and some embodiments contain 1 carbon. Examples of an alkyl include, but not limited to, methyl, ethyl, n-propyl, iso-propyl, n-butyl, iso-butyl, t-butyl, sec-butyl, n-pentyl, iso-pentyl, sec-pentyl, neo-pentyl, hexyl, iso-hexyl, sec-hexyl, neo-hexyl, and the like.

The term "$C_{1-4}$ alkylcarboxamido" or "$C_{1-4}$ alkylcarboxamide" denotes a single $C_{1-4}$ alkyl group attached to the nitrogen of an amide group, wherein alkyl has the same definition as found herein. The $C_{1-5}$ alkylcarboxamido may be represented by the following:

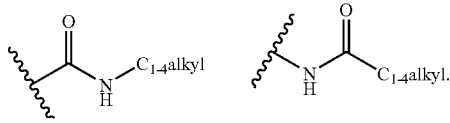

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{2-6}$ alkynyl" denotes a radical containing 2 to 6 carbons and at least one carbon-carbon triple bond, some embodiments are 2 to 4 carbons, and some embodiments have 2 carbons. Examples of an alkynyl include, but not limited to, ethynyl, prop-1-ynyl, 3-prop-2-ynyl, but-1-ynyl, 1-methyl-prop-2-ynyl, buta-1,3-diynyl, and the like. The term "alkynyl" includes di-ynes.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like.

The term "$C_{1-4}$ alkylsulfonamide" denotes

The term "$C_{1-4}$ alkylsulfinyl" denotes a $C_{1-6}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsulfonyl" denotes a $C_{1-6}$ alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-4}$ alkylthio" denotes a $C_{1-6}$ alkyl radical attached to a sulfide group of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-4}$alkylureyl" denotes

The term "amino" denotes the group —NH$_2$.

The term "carbo-$C_{1-6}$-alkoxy" denotes a $C_{1-6}$ alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "$C_{3-6}$ cycloalkyl" denotes a saturated ring radical containing 3 to 6 carbons; some embodiments, contain 3 to 5 carbons, some embodiments contain 3 to 4 carbons. Examples include, cyclopropyl, cyclobutyl, cyclopentyl, cyclohexyl.

The term "$C_{2-6}$ dialkylamino" denotes an amino substituted with two of the same or different alkyl radicals wherein alkyl radical has the same definition as described herein. A $C_{2-6}$ dialkylamino may be represented by the following groups:

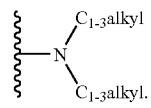

Examples of $C_{2-6}$ dialkylamino include, but not limited to, dimethylamino, methylethylamino, diethylamino, methylpropylamino, methylisopropylamino, and the like.

The term "$C_{1-4}$ dialkylcarboxamido" or "$C_{1-4}$ dialkylcarboxamide" denotes two alkyl radicals, that are the same or different, attached to an amide group, wherein alkyl has the same definition as described herein. A $C_{1-4}$ dialkylcarboxamido may be represented by the following groups:

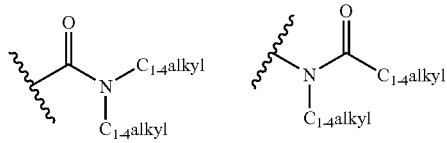

wherein $C_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "halogen" or "halo" denotes to a fluoro, chloro, bromo or iodo group.

The term "$C_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "$C_{1-4}$ haloalkyl" denotes an alkyl group wherein the alkyl is substituted with halogen ranging from one to fully substituted, wherein a fully substituted haloalkyl can be represented by the formula $C_nL_{2h+1}$ wherein L is a halogen and "h" represents the number of carbon atoms; when more than one halogen is present then the halogens may be the same or different and selected from the group consisting of F, Cl, Br and I; it is understood that the terms "alkyl" and "halogen" have the same definition as found herein. In some embodiments, haloalkyl is a "$C_{1-4}$ haloalkyl" and the group contains 1 to 4 carbons, some embodiments contain 1 to 3 carbons, some embodiments contain 1 to 2 carbons, some embodiments contain 1 carbon. When the haloalkyl is fully substituted with halogen atoms, this group is referred herein as a perhaloalkyl, one example, is an alkyl fully substituted with fluorine atoms and is referred to herein as a "perfluoroalkyl." In some embodiments, examples of a haloalkyl include, but not limited to, difluoromethyl, fluoromethyl, 2,2,2-trifluoroethyl, 2,2-difluoro-ethyl, 2-fluoro-ethyl, 1,2,2-trifluoroethyl, 1,2-difluoro-ethyl, 1,1-difluoro-ethyl, 1,1,2-trifluoroethyl, 3,3,3-trifluoro-propyl, 2,2-difluoro-propyl, 3,3-difluoro-propyl, 3-fluoro-propyl, 2,3,3-trifluoro-propyl, 2,3-Difluoro-propyl, 2,2,3,3,3-pentafluoro-propyl, 2,2,3,3-tetrafluoro-propyl, 2,2,3-trifluoro-propyl, 1,2,3,3-tetrafluoro-propyl, 1,2,3-trifluoro-propyl, 3,3-difluoro-propyl, 1,2,2,3-tetrafluoro-propyl, 4,4-difluoro-butyl, 3,3-difluoro-butyl, 4,4,4-trifluoro-butyl, 3,3-difluoro-butyl, and the like. In some embodiments, examples of a perfluoroalkyl include, but not limited to, trifluoromethyl, pentafluoroethyl, heptafluoropropyl, 1,2,2,2-tetrafluoro-1-trifluoromethyl-ethyl, and the like.

The term "$C_{1-4}$ haloalkylsulfinyl" denotes a haloalkyl radical attached to a sulfoxide group of the formula: —S(O)— wherein the haloalkyl radical has the same definition as described herein.

The term "$C_{1-4}$ haloalkylsulfonyl" denotes a haloalkyl radical attached to a sulfone group of the formula: —S(O)$_2$— wherein haloalkyl has the same definition as described herein.

The term "$C_{1-4}$ haloalkylthio" denotes a haloalkyl radical directly attached to a sulfur atom wherein the haloalkyl has the same meaning as described herein.

The term "hydroxyl" denotes the group —OH.

The term "nitro" denotes the group —NO$_2$.

CODON shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

COMPOSITION means a material comprising at least one component. A "pharmaceutical composition" is an example of a composition.

COMPOUND EFFICACY shall mean a measurement of the ability of a compound to inhibit or stimulate receptor functionality; i.e. the ability to activate/inhibit a signal transduction pathway, in contrast to receptor binding affinity. Exemplary means of detecting compound efficacy are disclosed in the Example section of this patent document.

COMPRISING, CONSISTING ESSENTIALLY OF, and CONSISTING OF are defined herein according to their standard meaning. A defined meaning set forth in the M.P.E.P. controls over a defined meaning in the art and a defined meaning set forth in controlling Federal Circuit case law controls over a meaning set forth in the M.P.E.P.

CONGESTIVE HEART FAILURE shall refer to a disorder in which the heart loses its ability to pump blood efficiently. Congestive heart failure becomes more prevalent with advancing age. Ischemic heart disease is the most common cause of congestive heart failure, accounting for 60-70% of all cases. An increased venous pressure greater than 12 mmHg is one of the major Framingham criteria for congestive heart failure, as is a reduction in cardiac output equivalent to a circulation time greater than 25 seconds.

CONSTITUTIVELY ACTIVE RECEPTOR shall mean a receptor stabilized in an active state by means other than through binding of the receptor to its ligand or a chemical equivalent thereof A CONSTITUTIVELY ACTIVE RECEPTOR may be endogenous or non-endogenous.

CONSTITUTIVELY ACTIVATED RECEPTOR shall mean an endogenous receptor that has been modified so as to be constitutively active.

CONSTITUTIVE RECEPTOR ACTIVATION shall mean activation of a receptor in the absence of binding to its ligand or a chemical equivalent thereof.

CONTACT or CONTACTING shall mean bringing at least two moieties together, whether in an in vitro system or an in vivo system.

DECREASE is used to refer to a reduction in a measurable quantity and is used synonymously with the terms "reduce", "diminish", "lower", and "lessen".

ENDOGENOUS shall mean a material that a mammal naturally produces. ENDOGENOUS in reference to, for example and not limitation, the term "receptor," shall mean that which is naturally produced by a mammal (for example, and not limitation, a human). ENDOGENOUS shall be understood to encompass allelic variants of a gene as well as the allelic polypeptide variants so encoded. As used herein, "endogenous GPCR" and "native GPCR" are used interchangeably. By contrast, the term NON-ENDOGENOUS in this context shall mean that which is not naturally produced by a mammal (for example, and not limitation, a human). For example, and not limitation, a receptor which is not constitutively active in its endogenous form, but when manipulated becomes constitutively active, is most preferably referred to herein as a "non-endogenous, constitutively activated receptor."

EXPRESSION VECTOR is defined herein as a DNA sequence that is required for the transcription of cloned DNA and the translation of the transcribed mRNAs in an appropriate host cell recombinant for said EXPRESSION VECTOR. An appropriately constructed EXPRESSION VECTOR should contain an origin of replication for autonomous replication in host cells, selectable markers, a limited number of useful restriction enzyme sites, a potential for high copy number, and active promoters. Said cloned DNA to be transcribed is operably linked to a constitutively or conditionally active promoter within said expression vector. By way of illustration and not limitation, pCMV is an expression vector.

G PROTEIN COUPLED RECEPTOR FUSION PROTEIN and GPCR FUSION PROTEIN, in the context of the invention disclosed herein, each mean a non-endogenous protein comprising an endogenous, constitutively active GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous GPCR. For example, and not limitation, in an endogenous state, if the G protein "$G_s\alpha$" is the predominate G protein that couples with the GPCR, a GPCR Fusion Protein based upon the specific GPCR would be a non-endogenous protein comprising the GPCR fused to $G_s\alpha$; in some circumstances, as will be set forth below, a non-predominant G protein can be fused to the GPCR. The G protein can be fused directly to the C-terminus of the constitutively active GPCR or there may be spacers between the two.

HOST CELL shall mean a cell capable of having a vector incorporated therein. In certain embodiments, the vector is an expression vector. Exemplary host cells include but are not limited to 293, 293T, CHO, MCB3901, and COS-7 cells, as well as melanophore cells.

HUMANIN ACTIVITY as relates to a compound shall mean said compound binds to and is a modulator of a Humanin receptor, wherein said receptor preferably is endogenous and more preferably FPRL2, and wherein said modulator preferably is agonist.

IN NEED OF PREVENTION OR TREATMENT as used herein refers to a judgement made by a caregiver (e.g. physician, nurse, nurse practitioner, etc. in the case of humans; veterinarian in the case of animals, including non-human mammals) that an individual or animal requires or will benefit from treatment. This judgement is made based on a variety of factors that are in the realm of a caregiver's expertise, but that include the knowledge that the individual or animal is ill, or will be ill, as the result of a condition that is treatable by the compounds of the invention.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean materials (e.g., ligand, candidate compound) that bind either to the endogenous form or to the constitutively activated form of the receptor so as to reduce the baseline intracellular response of the receptor observed in the absence of agonists.

ISCHEMIC HEART DISEASE shall refer to a disorder caused by lack of oxygen to the tissues of the heart, in which muscles of the heart are affected and the heart cannot pump properly. Ischemic heart disease is the most common cardiomyopathy in the United States.

ISOLATED shall mean that the material is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such a polynucleotide could be part of a vector and/or such a polynucleotide or polypeptide could be part of a composition, and still be isolated in that the vector or composition is not part of its natural environment.

LIGAND shall mean a molecule that specifically binds to a GPCR. A ligand may be, for example, a polypeptide, a lipid, a small molecule, an antibody. An endogenous ligand is a ligand that is an endogenous, natural ligand for a native GPCR. A ligand may be a GPCR "antagonist", "agonist", "partial agonist", or "inverse agonist", or the like.

As used herein, the terms MODULATE or MODIFY are meant to refer to an increase or decrease in the amount, quality, or effect of a particular activity, function or molecule. By way of illustration and not limitation, agonists, partial agonists, inverse agonists, and antagonists of a G protein-coupled receptor are modulators of the receptor.

MOTOR NEURON DISEASE shall refer to a disease characterized by a selective degeneration of the motor neurons of the spinal cord, brainstem, or motor cortex. Clinical subtypes are distinguished by the major site of degeneration.

MYOCARDIAL INFARCTION shall refer to the damage or death of an area of heart muscle because of an inadequate supply of oxygen to that area. Myocardial infarctions are often caused by a clot that blocks one of the coronary arteries (the blood vessels that bring blood and oxygen to heart muscle). The clot prevents blood and oxygen from reaching that area of the heart, leading to the death of heart cells in that area.

MYOPROTECTIVE shall refer to the property of protecting against muscle cell death in one or more contexts. It follows that a modulator of a myoprotective GPCR is a modulator of myoprotection.

NEUROPROTECTIVE shall refer to the property of protecting against neuronal cell death in one or more contexts. It follows that a modulator of a neuroprotective GPCR is a modulator of neuroprotection.

PARKINSON'S DISEASE is a chronic, progressive neurodegenerative disorder characterized by motor symptoms such as tremor, bradykinesia, muscle rigidity, gait dysfunction, and postural instability. Although researchers have identified degeneration of dopaminergic neurons in the substantia nigra as the primary pathophysiological mechanism, they believe that other neurotransmitter systems—such as the serontonergic and glutamatergic systems—are also intricately involved in the disease process.

PARTIAL AGONISTS shall mean materials (e.g. ligands, candidate compounds) that activate the intracellular response when they bind to the receptor to a lesser degree/extent than do full agonists.

PERIPHERAL NEUROPATHY is a broad term used to describe a variety of disorders which manifest as painful or uncomfortable sensations usually in the extremities and are of neuropathic origin. This condition is found commonly amongst end stage renal disease and diabetic patients. Distal symmetrical polyneuropathy (DSP)—a neuropathy affecting both diodes of the body and attacking the distal sensory nerves—is the most common clinical manifestation of diabetic neuropathy and accounts for approximately 80-85% of all neuropathy observed in diabetic patients.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

POLYNUCLEOTIDES shall mean RNA, DNA, or RNA/DNA hybrid sequences of more than one nucleotide in either single chain or duplex form. The polynucleotides of the invention may be prepared by any known method, including synthetic, recombinant, ex vivo generation, or a combination thereof, as well as utilizing any purification methods known in the art.

POLYPEPTIDE shall refer to a polymer of amino acids without regard to the length of the polymer. Thus, PEPTIDES, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term POLYPEPTIDE.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

PRION-ASSOCIATED DISEASE is intended herein to encompass, but not be limited to, bovine spongiform encephalopathy, Creutzfeldt-Jakob disease, kuru, Gerstmann-Straussler-Scheinker syndrome, and fatal familial insomnia.

PURIFIED is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). In certain embodiments, a polynucleotide is substantially pure when at least about 50%, at least about 60%, at least about 75%, at least about 85%, at least about 90%, at least about 95%, at least about 96%, at least about 97%, at least about 98%, at least about 99%, or at least about 99.5% of a sample contains a single polynucleotide sequence. In some embodiments, a substantially pure polynucleotide typically comprises about 50%, about 60%, about 70%, about 80%, about 90%, about 95%, about 96%, about 97%, about 98%, about 99% or about 99.5% weight/weight of a polynucleotide sample.

Similarly, the term PURIFIED is used herein to describe a polypeptide of the invention that has been separated from other compounds including, but not limited to, nucleic acids, lipids, carbohydrates and other proteins. In certain embodiments, a polypeptide is substantially pure when at least about 50%, at least about 60%, at least about 75%, at least about 85%, at least about 90%, at least about 95%, at least about 96%, at least about 97%, at least about 98%, at least about 99%, or at least about 99.5% of the polypeptide molecules of a sample have a single amino acid sequence. In some embodiments, a substantially pure polypeptide typically comprises about 50%, about 60%, about 70%, about 80%, about 90%, about 95%, about 96%, about 97%, about 98%, about 99% or about 99.5% weight/weight of a protein sample.

Similarly, the term PURIFIED is used herein to describe a modulator of the invention. In certain embodiments, a substantially pure modulator typically comprises at least about 70%, at least about 80%, at least about 90%, at least about 95%, at least about 96%, at least about 97%, at least about 98%, at least about 99% or at least about 99.5% weight/weight of a preparation of said modulator. In certain embodiments, the modulator has an "at least" purity ranging from any number, to the thousandth position, between 90% and 100% (e.g., at least 99.995% pure).

Further, as used herein, the term PURIFIED does not require absolute purity; rather, it is intended as a relative definition.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins.

SECOND MESSENGER shall mean an intracellular response produced as a result of receptor activation. A second messenger can include, for example, inositol triphosphate ($IP_3$), diacylglycerol (DAG), cyclic AMP (cAMP), cyclic GMP (cGMP), and $Ca^{2+}$. Second messenger response can be measured for a determination of receptor activation. In addition, second messenger response can be measured for the identification of candidate compounds as, for example, inverse agonists, partial agonists, agonists, and antagonists.

SIGNAL TO NOISE RATIO shall mean the signal generated in response to activation, amplification, or stimulation wherein the signal is above the background noise or the basal level in response to non-activation, non-amplification, or non-stimulation.

SPACER shall mean a translated number of amino acids that are located after the last codon or last amino acid of a gene, for example a GPCR of interest, but before the start codon or beginning regions of the G protein of interest, wherein the translated number amino acids are placed in-frame with the beginnings regions of the G protein of interest. The number of translated amino acids can be one, two, three, four, etc., and up to twelve.

STIMULATE or STIMULATING, in relationship to the term "response" shall mean that a response is increased in the presence of a compound as opposed to in the absence of the compound.

STROKE is a cardiovascular disease that affects the blood vessels supplying blood to the brain and is intended herein to include cerebral thrombosis, the most common type of STROKE. Cerebral thrombosis occurs when a blood clot (thrombus) forms and blocks blood flow in an artery bringing blood to part of the brain. Blood clots usually form in arteries damaged by atherosclerosis.

SUBJECT shall mean primates, including but not limited to humans and baboons, as well as pet animals such as dogs and cats, laboratory animals such as rats and mice, and farm animals such as horses, sheep, and cows.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

VARIANT as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. A typical variant of a polypeptide differs in amino acid sequence from another, reference polypeptide. A variant and reference polypeptide may differ in amino acid sequence by one or more substitutions, additions, deletions in any combination. A variant of a polynucleotide or polypeptide may be a naturally occurring one such as an ALLELIC VARIANT, or it may be a variant that is not known to occur naturally. Non-naturally occurring variants of polynucleotides and polypeptides may be made by mutagenesis techniques or by direct synthesis.

A. Introduction

The order of the following sections is set forth for presentational efficiency and is not intended, nor should be construed, as a limitation on the disclosure or the claims to follow.

B. Receptor Expression

1. GPCR Polypeptides of Interest

As used herein, "an FPRL2 amino acid sequence" is intended to encompass the endogenous human FPRL2 amino acid sequence of SEQ ID NO:2 as well as a variant amino acid sequence at least about 75%, at least about 80%, at least about 85%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2. In other words, a GPCR comprising a variant of the amino acid sequence of SEQ ID NO:2 also may be used in the subject methods. In certain embodiments, a GPCR that may be used in the subject methods may comprise an allelic variant of the amino acid sequence of SEQ ID NO:2. By way of illustration and not limitation, an allelic variant of the amino acid sequence of SEQ ID NO:2 may comprise a substitution of alanine for glycine at amino acid position 94 of SEQ ID NO:2, a substitution of threonine for serine at amino acid position 211 of SEQ ID NO:2, a substitution of histidine for aspartic acid at amino acid position 338 of SEQ ID NO:2, or may comprise any combination of said amino acid substitutions (GenBank® Accession No. AAA58482). In certain embodiments, an allelic variant of the amino acid sequence of SEQ ID NO:2 is encoded by an endogenous FPRL2 nucleotide sequence obtainable by performing polymerase chain reaction (PCR) on a human DNA sample using specific primers SEQ ID NO:3 and SEQ ID NO:4. In some embodiments, an allelic variant of the amino acid sequence of SEQ ID NO:2 is encoded by an endogenous FPRL2 nucleotide sequence obtainable by performing polymerase chain reaction (PCR) on a human DNA sample using a specific primer comprising SEQ ID NO:3 and a specific primer comprising SEQ ID NO:4. In certain embodiments, a variant amino acid sequence that may be used in the subject methods is a mammalian ortholog of the amino acid sequence of SEQ ID NO:2. By way of illustration and not limitation, the FPRL2 amino acid sequences of Pan troglodytes (GenBank® Accession No. P79243, e.g.), Gorilla gorilla gorilla (GenBank® Accession No. P79178, e.g.), Pongo pygmaeus (GenBank® Accession No. P79237, e.g.), and Macaca mulatto (GenBank® Accession No. P79191) are envisioned to be within the scope of "an FPRL2 amino acid sequence". In certain embodiments, a GPCR that may be used in the subject methods may comprise a non-endogenous, constitutively activated mutant of the amino acid sequence of SEQ ID NO:2, an allele of SEQ ID NO:2, or a mammalian ortholog of SEQ ID NO:2. As is known in the art, a constitutively activated GPCR may be made using a variety of methods (see, e.g., PCT Application Number PCT/US98/07496 published as WO 98/46995 on 22 Oct. 1998; and U.S. Pat. No. 6,555,339; the disclosure of each of which is hereby incorporated by reference in its entirety.) A biologically active fragment of the amino acid sequence of SEQ ID NO:2, of an allele of SEQ ID NO:2, of a mammalian ortholog of SEQ ID NO:2, of a non-endogenous, constitutively activated mutant of endogenous FPRL2, or of an amino acid sequence at least about 75%, at least about 80%, at least about 85%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2 may be used in the subject invention. By way of illustration and not limitation, deletion of an N-terminal methionine or an N-terminal signal peptide is envisioned to provide a biologically active fragment that may be used in the subject methods.

In certain embodiments, a GPCR that may be used in the subject methods may comprise an amino acid sequence at least about 75%, at least about 80%, at least about 85%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:2. In certain embodiments, a GPCR that may be used in the subject methods may comprise an amino acid sequence at least about 95%, at least about 96%, at least about 97%, at least about 98% or at least about 99% identical to the amino acid sequence of SEQ ID NO:2. In certain embodiments, a GPCR that may be used in the subject methods may comprise an amino acid sequence at least about 75% identical to the amino acid sequence of SEQ ID NO:2. In certain embodiments, a GPCR that may be used in the subject methods may comprise an amino acid sequence at least about 80% identical to the amino acid sequence of SEQ ID NO:2. In certain embodiments, a GPCR that may be used in the subject methods may comprise an amino acid sequence at least about 85% identical to the amino acid sequence of SEQ ID NO:2. In certain embodiments, a GPCR that may be used in the subject methods may comprise an amino acid sequence at least about 90% identical to the amino acid sequence of SEQ ID NO:2. In certain embodiments, a GPCR that may be used in the subject methods may comprise an amino acid sequence at least about 91% identical to the amino acid sequence of SEQ ID NO:2. In certain embodiments, a GPCR that may be used in the subject methods may comprise an amino acid sequence at least about 92% identical to the amino acid sequence of SEQ ID NO:2. In certain embodiments, a GPCR that may be used in the subject methods may comprise an amino acid sequence at least about 93% identical to the amino acid sequence of SEQ ID NO:2. In certain embodiments, a GPCR that may be used in the subject methods may comprise an amino acid sequence at least about 94% identical to the amino acid sequence of SEQ ID NO:2. In certain embodiments, a GPCR that may be used in the subject methods may comprise an amino acid sequence at least about 95% identical to the amino acid sequence of SEQ ID NO:2. In certain embodiments, a GPCR that may be used in the subject methods may comprise an amino acid sequence at least about 96% identical to the amino acid sequence of SEQ ID NO:2. In certain embodiments, a GPCR that may be used in the subject methods may comprise an amino acid sequence at least about 97% identical to the amino acid sequence of SEQ ID NO:2. In certain embodiments, a GPCR that may be used in the subject methods may comprise an amino acid sequence at least about 98% identical to the amino acid sequence of SEQ ID NO:2. In certain embodiments, a GPCR that may be used in the subject methods may comprise an amino acid sequence at least about 99% identical to the amino acid sequence of SEQ ID NO:2. By an amino acid sequence having at least, for example, 95% "identity" to the amino acid sequence of SEQ ID NO:2 is meant that the amino acid sequence is identical to the amino acid sequence of SEQ ID NO:2 except that it may include up to five amino acid alterations per each 100 amino acids of the amino acid sequence of SEQ ID NO:2. Thus, to obtain an amino acid sequence having at least 95% identity to that of SEQ ID NO:2, up to 5% (5 of 100) of the amino acid residues in the sequence may be inserted, deleted, or substituted with another amino acid compared with the amino acid sequence of SEQ ID NO:2. These alternations may occur at the amino or carboxy termini or anywhere between those terminal positions, interspersed either individually among residues in the sequence or in one or more contiguous groups within the sequence.

In some embodiments, an FPRL2 amino acid sequence that may be used in the subject methods is an amino acid sequence of a G protein-coupled receptor encoded by a complementary sequence to the sequence of a polynucleotide that hybridizes under stringent conditions to filter-bound DNA having the sequence set forth in SEQ ID NO:1. Hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 5 mM sodium phosphate (pH 7.6), 5×Denhardt's solution, 10% dextran sulfate, and 20 g/ml denatured, sheared salmon sperm DNA; followed by washing the filter in 0.1×SSC at about 65° C.

a. Sequence Identity

A preferred method for determining the best overall match between a query sequence (e.g., the amino acid sequence of SEQ ID NO:2) and a sequence to be interrogated, also referred to as a global sequence alignment, can be determined using the FASTDB computer program based on the algorithm of Brutlag et al. [Comp App Biosci (1990) 6:237-245; the disclosure of which is hereby incorporated by reference in its entirety]. In a sequence alignment the query and interrogated sequences are both amino acid sequences. The results of said global sequence alignment is in percent identity. Preferred parameters used in a FASTDB amino acid alignment are: Matrix=PAM 0, k-tuple=2, Mismatch Penalty=1, Joining Penalty=20, Randomization Group=25, Length=0, Cutoff Score=1, Window Size=sequence length, Gap Penalty=5, Gap Size Penalty=0.05, Window Size=247 or the length of the interrogated amino acid sequence, whichever is shorter.

If the interrogated sequence is shorter than the query sequence due to N- or C-terminal deletions, not because of internal deletions, the results, in percent identity, must be manually corrected because the FASTDB program does not account for N- and C-terminal truncations of the interrogated sequence when calculating global percent identity. For interrogated sequences truncated at the N- and C-termini, relative to the query sequence, the percent identity is corrected by calculating the number of residues of the query sequence that are N- and C-terminal of the interrogated sequence, that are not matched/aligned with a corresponding interrogated sequence residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the interrogated sequence, which are not matched/aligned with the query sequence, are considered for the purposes of manually adjusting the percent identity score. That is, only query amino acid residues outside the farthest N- and C-terminal residues of the interrogated sequence.

For example, a 90 amino acid residue interrogated sequence is aligned with a 100-residue query sequence to determine percent identity. The deletion occurs at the N-terminus of the interrogated sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched, the final percent identity would be 90%.

In another example, a 90-residue interrogated sequence is compared with a 100-residue query sequence. This time the deletions are internal so there are no residues at the N- or C-termini of the interrogated sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other corrections are made for the purposes of the present invention.

b. Fusion Proteins

In certain embodiments, a polypeptide of interest is a fusion protein, and may contain, for example, an affinity tag domain or a reporter domain. Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor. It is expressly contemplated that such a fusion protein may contain a heterologous N-terminal domain (e.g., an epitope tag) fused in-frame with a GPCR that has had its N-terminal methionine residue either deleted or substituted with an alternative amino acid.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula, Renilla reniformis* or *Renilla muelleri*), or light emitting variants thereof. Other suitable reporter domains include fluorescent proteins, (from e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase.

Also as is known in the art, an affinity tags or a reporter domain may be present at any position in a polypeptide of interest. However, in most embodiments, they are present at the C- or N-terminal end of a polypeptide of interest.

2. Nucleic Acids Encoding GPCR Polypeptides of Interest

Since the genetic code and recombinant techniques for manipulating nucleic acid are known, and the amino acid sequences of GPCR polypeptides of interest described as above, the design and production of nucleic acids encoding a GPCR polypeptide of interest is well within the skill of an artisan. In certain embodiments, standard recombinant DNA technology (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.) methods are used. For example, GPCR coding sequences may be isolated from a library of GPCR coding sequence using any one or a combination of a variety of recombinant methods that do not need to be described herein. Subsequent substitution, deletion, and/or addition of nucleotides in the nucleic acid sequence encoding a protein may also be done using standard recombinant DNA techniques.

For example, site directed mutagenesis and subcloning may be used to introduce/delete/substitute nucleic acid residues in a polynucleotide encoding a polypeptide of interest. In other embodiments, PCR may be used. Nucleic acids encoding a polypeptide of interest may also be made by chemical synthesis entirely from oligonucleotides (e.g., Cello et al., Science (2002) 297:1016-8).

In some embodiments, the codons of the nucleic acids encoding polypeptides of interest are optimized for expression in cells of a particular species, particularly a mammalian, e.g., mouse, rat, hamster, non-human primate, or human, species. In some embodiments, the codons of the nucleic acids encoding polypeptides of interest are optimized for expression in cells of a particular species, particularly an amphibian species.

a. Vectors

The invention further provides vectors (also referred to as "constructs") comprising a subject nucleic acid. In many embodiments of the invention, the subject nucleic acid sequences will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

A variety of expression vectors are available to those in the art for purposes of producing a polypeptide of interest in a cell. One suitable vector is pCMV, which is used in certain embodiments. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, kanr or neor (aminoglycoside phosphotransferase genes), the hygromycin B phosphotransferase gene, and the like.

As mentioned above, polypeptides of interest may be fusion proteins that contain an affinity domain and/or a reporter domain. Methods for making fusions between a reporter or tag and a GPCR, for example, at the C- or N-terminus of the GPCR, are well within the skill of one of skill in the art (e.g. McLean et al, Mol. Pharma. Mol Pharmacol. 1999 56:1182-91; Ramsay et al., Br. J. Pharmacology, 2001, 315-323) and will not be described any further. It is expressly contemplated that such a fusion protein may contain a heterologous N-terminal domain (e.g., an epitope tag) fused in-frame with a GPCR that has had its N-terminal methionine residue either deleted or substituted with an alternative amino acid. It is appreciated that a polypeptide of interest may first be made from a native polypeptide and then operably linked to a suitable reporter/tag as described above.

The subject nucleic acids may also contain restriction sites, multiple cloning sites, primer binding sites, ligatable ends, recombination sites etc., usually in order to facilitate the construction of a nucleic acid encoding a polypeptide of interest.

b. Host Cells

The invention further provides host cells comprising a vector comprising a subject nucleic acid. Suitable host cells include prokaryotic, e.g., bacterial cells (for example *E. coli*), as well as eukaryotic cells e.g. an animal cell (for example an insect, mammal, fish, amphibian, bird or reptile cell), a plant cell (for example a maize or *Arabidopsis* cell), or a fungal cell (for example a *S. cerevisiae* cell). In certain embodiments, any cell suitable for expression of a polypeptide of interest-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293 ["293"], Graham et al. J. Gen Virol. 36:59 (1977)); HEK-293T ["293T"] cells; baby hamster kidney cells (BHK, ATCC CCL 10); chinese hamster ovary-cells (CHO, Urlaub and Chasin, Proc. Natl. Acad. Sci. (USA) 77:4216, (1980); Syrian golden hamster cells MCB3901 (ATCC CRL-9595); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44-68 (1982)); NIH/3T3 cells (ATCC CRL-1658); and mouse L cells (ATCC CCL-1). In certain embodiments, melanophores are used. Melanophores are skin cells found in lower vertebrates. Relevant materials and methods will be followed according to the disclosure of U.S. Pat. No. 5,462,856 and U.S. Pat. No. 6,051,386. These patent disclosures are hereby incorporated by reference in their entirety. Additional cell lines will become apparent to those of ordinary skill in the art, and a wide variety of cell lines are available from the American Type Culture Collection, 10801 University Boulevard, Manassas, Va. 20110-2209.

C. Screening of Candidate Compounds

1. Generic GPCR Screening Assay Techniques

When a G protein receptor becomes active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, activated receptors continue to exchange GDP to GTP. A non-hydrolyzable analog of GTP, [$^{35}$S]GTPγS, can be used to monitor enhanced binding to membranes which express activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g. an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, an activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid PIP$_2$, releasing two intracellular messengers: diacycloglycerol (DAG) and inistol 1,4,5-triphoisphate (IP$_3$). Increased accumulation of IP$_3$ is associated with activation of Gq- and Go-associated receptors. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Assays that detect IP$_3$ accumulation can be utilized to determine if a candidate compound is, e.g., an inverse agonist to a Gq- or Go-associated receptor (i.e., such a compound would decrease the levels of IP$_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively active GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian expression system, as such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR. The GPCR Fusion Protein is preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Based upon convenience, it is preferred to use a spacer. In some embodiments it is preferred, that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 5(a) below) be available for insertion of an endogenous GPCR sequence therein; this provides for further efficiency in the context of large-scale screening of a variety of different endogenous GPCRs having different sequences.

As noted above, activated GPCRs that couple to Gi, Gz and Go are expected to inhibit the formation of cAMP making assays based upon these types of GPCRs challenging [i.e., the cAMP signal decreases upon activation, thus making the direct identification of, e.g., agonists (which would further decrease this signal) challenging]. As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE B

| G protein | Effect of cAMP Production upon Activation of GPCR (i.e., constitutive activation or agonist binding) | Effect of IP$_3$ Accumulation upon Activation of GPCR (i.e., constitutive activation or agonist binding) | Effect of cAMP Production upon contact with an Inverse Agonist | Effect on IP$_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein. In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will forces the endogenous Gi coupled receptor to couple to its non-endogenous G protein, Gq, such that the second messenger, for example, inositol triphosphate or diacylglycerol, can be measured in lieu of cAMP production.

4. Co-Transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In certain embodiments, an effective technique in measuring the decrease in production of cAMP as an indication of activation of a receptor that predominantly couples Gi upon activation can be accomplished by co-transfecting a signal enhancer, e.g., a non-endogenous, constitutively activated receptor that predominantly couples with Gs upon activation (e.g. TSHR-A623I; see infra), with the Gi linked GPCR. As is apparent, activation of a Gs coupled receptor can be determined based upon an increase in production of cAMP. Activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with expression vector alone provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with the "target receptor", an inverse agonist of the Gi coupled target receptor will increase the measured cAMP signal, while an agonist of the Gi coupled target receptor will decrease this signal.

Candidate compounds that are directly identified using this approach should be assessed independently to ensure that these do not target the signal enhancing receptor (this can be done prior to or after screening against the co-transfected receptors).

D. Medicinal Chemistry

Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation-based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of individual members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Candidate Compounds Identified as Modulators

Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

In certain embodiments, said identified modulator is bioavailable. A number of computational approaches available to those of ordinary skill in the art have been developed for prediction of oral bioavailability of a drug [Ooms et al., Biochim Biophys Acta (2002) 1587:118-25; Clark & Grootenhuis, Curr Opin Drug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is hereby incorporated by reference in its entirety). Furthermore, positron emission tomography GET) has been successfully used by a number of groups to obtain direct measurements of drug distribution, including an assessment of oral bioavailability, in the mammalian body following oral administration of the drug, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is hereby incorporated by reference in its entirety]. Also, see infra, including Example 18.

In certain embodiments, said bioavailable identified modulator further is able to cross the blood-brain barrier. A number of computational approaches available to those of ordinary skill in the art have been developed for prediction of the permeation of the blood-brain barrier [Ooms et al., Biochim Biophys Acta (2002) 1587:118-25; Clark & Grootenhuis, Curr Opin Drug Discov Devel (2002) 5:382-90; Cheng et al., J Comput Chem (2002) 23:172-83; Norinder & Haeberlein, Adv Drug Deliv Rev (2002) 54:291-313; Matter et al., Comb Chem High Throughput Screen (2001) 4:453-75; Podlogar & Muegge, Curr Top Med Chem (2001) 1:257-75; the disclosure of each of which is hereby incorporated by reference in its entirety). A number of in vitro methods have been developed to predict blood-brain barrier permeability of drugs [Lohmann et al., J Drug Target (2002) 10:263-76; Hansen et al., J Pharm Biomed Anal (2002) 27:945-58; Otis et al., J Pharmacol Toxicol Methods (2001) 45:71-7; Dehouck et al, J Neurochem (1990) 54:1798-801; the disclosure of each of which is hereby incorporated by reference in its entirety]. Furthermore, a number of strategies have been developed to enhance drug delivery across the blood-brain barrier [Scherrmann, Vascul Pharmacol (2002) 38:349-54; Pardridge, Arch Neurol (2002) 59:35-40; Pardridge, Neuron (2002) 36:555-8; the disclosure of each of which is hereby incorporated by reference in its entirety]. Finally, positron emission tomography (PET) has been successfully used by a number of groups to obtain direct measurements of drug distribution, including that within brain, in the mammalian body, including non-human primate and human body [Noda et al., J Nucl Med (2003) 44:105-8; Gulyas et al., Eur J Nucl Med Mol Imaging (2002) 29:1031-8; Kanerva et al., Psychopharmacology (1999) 145:76-81; the disclosure of each of which is hereby incorporated by reference in its entirety].

E. Compounds of the Invention

Compounds of the Invention

One aspect of the present invention pertains to certain Dimethyl octahydro-phenanthrene carboxylic acid amide derivatives of Formula (I):

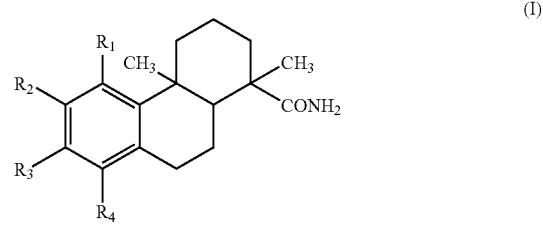

(I)

wherein:

$R_1$-$R_4$ are each independently selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{2-6}$ alkynyl, $C_{1-4}$ alkylamino, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and thiol; or a pharmaceutically acceptable salt, solvate or hydrate thereof.

In some embodiments, at least one $R_1$-$R_4$ group is not H.

In some embodiments, when $R_1$, $R_3$, and $R_4$ are each H, then $R_2$ is not —OAc or —OCH$_3$.

In some embodiments, when $R_1$, and $R_4$ are both H, and $R_3$ is —CH$_3$, then $R_2$ is not —OH.

In some embodiments, when $R_1$, and $R_4$ are both H, and $R_2$ is H or Br, then $R_3$ is not —CH(CH$_3$)$_2$.

In some embodiments, when $R_1$, $R_2$, and $R_3$ are each H, then $R_4$ is not —OAc.

In some embodiments, $R_1$ is H or halogen. In some embodiments, $R_1$ is H and can be represented by Formula Ib) as shown below:

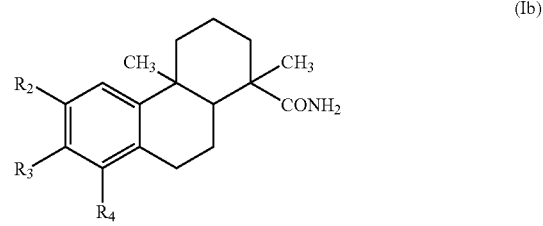

(Ib)

wherein each variable in Formula (Ib) has the same meaning as described herein, supra and infra.

In some embodiments, $R_4$ is H or halogen. In some embodiments, $R_4$ is H and can be represented by Formula (Id) as shown below:

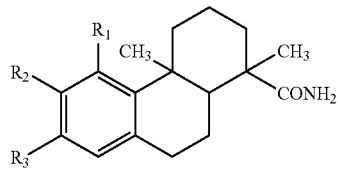

(Id)

wherein each variable in Formula (Id) has the same meaning as described herein, supra and infra. In some embodiment, compound of the present invention are of Formula (Id) wherein $R_1$ is H; these compound can be represented by Formula (If) as shown below:

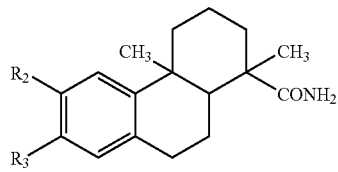

(If)

wherein each variable in Formula (Id) has the same meaning as described herein, supra and infra.

In some embodiment, $R_2$ is selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{2-6}$ dialkylamino, halogen, hydroxyl, nitro, and thiol.

In some embodiment, $R_2$ is selected form the group consisting of H, $C_{2-6}$ alkynyl, $C_{1-4}$ alkylamino, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, $C_{1-4}$ haloalkoxy, $C_{1-4}$ haloalkyl, $C_{1-4}$ haloalkylsulfinyl, $C_{1-4}$ haloalkylsulfonyl, and $C_{1-4}$ haloalkylthio.

In some embodiment, $R_2$ is H or halogen. In some embodiments, $R_2$ is H.

In some embodiment, $R_3$ is selected form the group consisting of H, $C_{1-5}$ acyl, $C_{1-5}$ acyloxy, C alkenyl, $C_{1-4}$ alkoxy, $C_{1-6}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{2-6}$ dialkylamino, halogen, hydroxyl, nitro, and thiol. In some embodiment, $R_3$ is $C_{1-6}$ alkyl. In some embodiment, $R_3$ is selected form the group consisting of H, $C_{2-6}$ alkynyl, $C_{1-4}$ alkylamino, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, $C_{1-4}$ haloalkoxy, $C_{1-4}$ haloalkyl, $C_{1-4}$ haloalkylsulfinyl, $C_{1-4}$ haloalkylsulfonyl, and $C_{1-4}$ haloalkylthio.

One aspect of the present invention pertains to pharmaceutical composition comprising a pharmaceutically acceptable carrier or excipient and a compound of Formula (I):

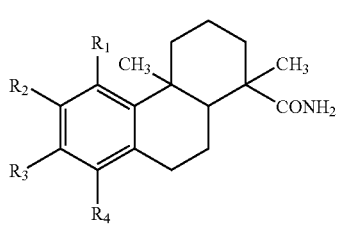

(I)

wherein:

$R_1$-$R_4$ are each independently selected form the group consisting of H, $C_{1-5}$ acyl, $C_{1-5}$ acyloxy, $C_{2-6}$ alkenyl, $C_{1-4}$ alkoxy, $C_{1-6}$ alkyl, $C_{1-4}$ alkylcarboxamide, $C_{2-6}$ alkynyl, $C_{1-4}$ alkylamino, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and thiol; or a pharmaceutically acceptable salt, solvate or hydrate thereof.

F. Synthetic Methods for Making Compounds of the Invention

The compounds of the present invention can be readily prepared according to a variety of synthetic regimes, all of which would be familiar to one skilled in the art. One method for preparing compounds of the invention can be through electrophilic aromatic substitution reactions wherein the aromatic ring can be substituted (i.e., at least one $R_1$-$R_4$ group is other than H) or unsubstituted (i.e., the $R_1$-$R_4$ groups are all H). By way of illustration, starting with 1,4a-dimethyl-1,2,3,4,4a,9,10,10a-octahydro-phenanthrene-1-carboxylic acid amide (A) or a protected derivative thereof, a variety of aromatic substitutions can be introduced to the aromatic ring. Compound (A) has been described by Wenkert and co-workers in the Journal of the American Chemical Society (1958), 80 211-17 and the Journal of the American Chemical Society (1958), 80 217-19, both incorporated by reference in their entirety. One example of an aromatic substitution reaction that can be used is the nitration reaction. A large number of nitration reagents and procedures are available in the literature, for example, $H_2SO_4$/$HNO_3$ in the presence or absence of solvent, nitronium tetrafluoroborate in polar solvent(s) such as sulfolane, and the like. The nitro group of Compound (B) can be reduced to amine (c) using, for example, $SnCl_4$, $H_2$ in the presence of a Pd catalyst, and the like. These examples are shown below:

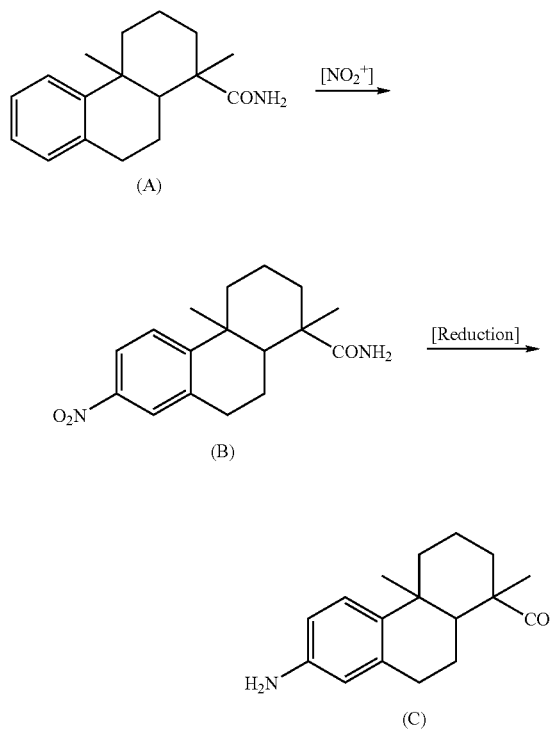

Amine (C) can be allowed to react with a variety of reagents. For example, $C_{1-4}$ alkyl carboxylic acids can be coupled with amine (C) using known coupling reagents to give amide (D). Alternatively, the carboxylic acids can be first converted to their corresponding acid chlorides and subsequently allowed to react with amine (C) to give amide (D). In another procedure, $C_{1-4}$ alkyl isocyanates can be allowed to react with amine (C) to give urea (E). In still another procedure, amine (C) can be converted to $C_{1-4}$ alkylamino or $C_{2-6}$ dialkylamino (F) via methods know in the art, for example, treatment with paraformaldehyde (for methylation), or a higher order aldehyde or ketone, followed by reduction with $NaBH_3CN$ or similar reducing agent known in the art. Alternatively, amine (C) can be readily alkylated, for example, by using an $C_{1-4}$ allyl halide in the presence of a base. It is understood that the equivalents of reagent will influence whether the $C_{1-4}$ alkylamino or $C_{2-6}$ dialkylamino is the product, the use of about 1.0 to about 1.2 equivalents will provide Compound F wherein the substituents is —$NHC_{1-4}$ alkyl, whereas the use of at least 2 equivalents will provide Compound (F) where the substituents is —$N(C_{1-4}$ alkyl$)_2$. Further, unsymmetrical a —$N(C_{1-4}$ alkyl$)_2$ substituent, where the alkyl groups are different, can be obtained by conducting independent single alkylation steps. These examples are shown below:

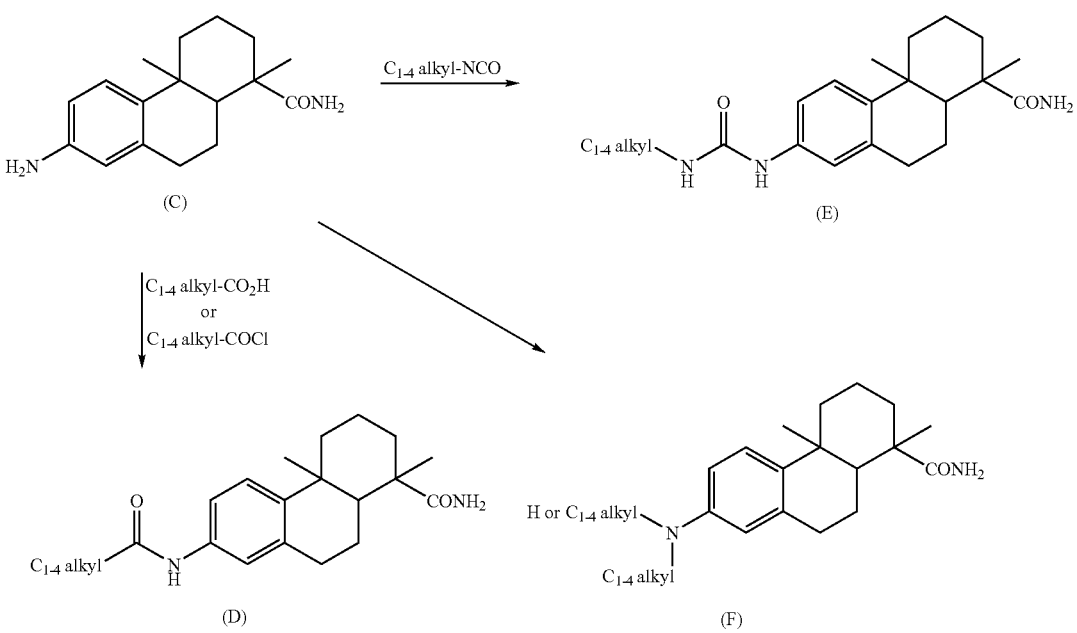

In yet another procedure, amine (C) can be converted to the diazonium salt intermediate (G), using for example, NaNO$_2$/H$_3$O$^+$, and subsequently allowed to react with a variety of reagents, for example, CuCl, CuBr, CuCN, fluoroboric acid, H$_2$O, Cu(I)/C$_{1-4}$ alkylSH, and the like. A few illustrative examples are shown below:

a base, and the like. In a subsequent procedure, Compound (M) can be rearranged under Fries rearrangement conditions to give Compounds (N') and/or (N"); suitable conditions include for example, Lewis Acid, AlCl$_3$, Sc(OTf)$_3$, and the like. A similar rearrangement can also take place for the amide group of Compound (D) under photo (hv) conditions.

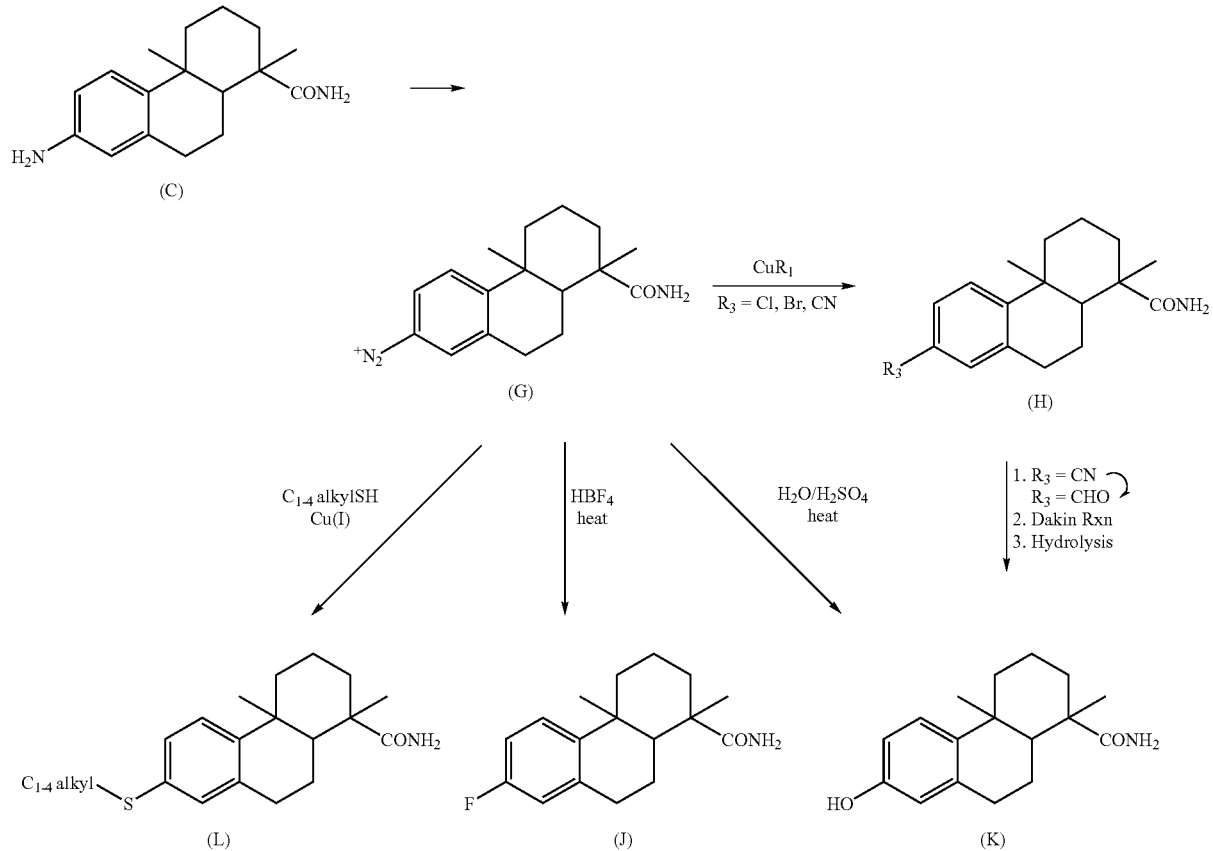

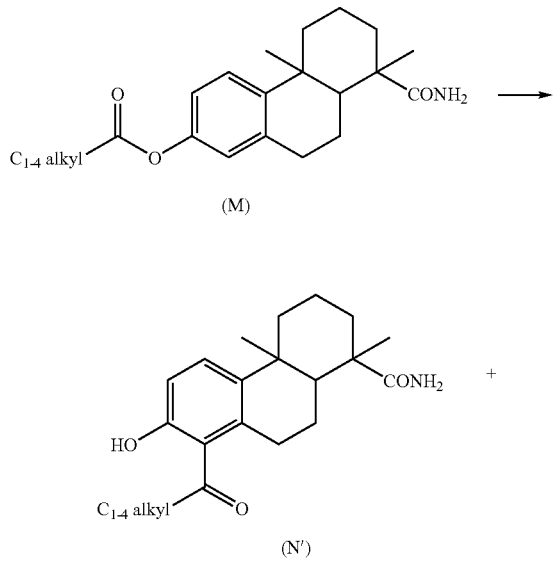

Compound (L) can be further oxidized to give C$_{1-4}$ alkylsulfinyl and C$_{1-4}$ alkylsulfonyl using H$_2$O$_2$, mCPBA, and the like. In an alternative manner, Compound (H) [R$_3$=Br] can be prepared directly from Compound (A) via halogenation reactions using methods known in the art, for example, Br$_2$, Br$_2$/AlBr$_3$, Br$_2$/FeBr$_3$ and like reagents. In a similar manner, Compound (A) can be iodinated using, for example, I$_2$, I$_2$/HNO$_3$, and like reagents. In another example, the nitrile of Compound (H), R$_3$=CN, can be readily hydrolyzed to a carboxamide using acidic or basic conditions known in the art. In another example, the nitrile of Compound (H), R$_3$=CN, can be converted to an aldehyde (R$_3$=CHO) using methods known in the art, for example, DIBAL and the like. In a subsequent step, the aldehyde can be oxidized to the carboxyl group (R$_3$=CO$_2$H). In an alternative manner compared to that described above, Compound (K) can be prepared from Compound (H), R$_3$=CHO, via the Dakin Rxn and after hydrolysis. In another example, Compound (K) can be readily alkylated with a C$_{1-4}$ alkylhalide or like reagent in the presence of base to give a C$_{1-4}$ alkoxy group. In still another example, Compound (K) can be acylated to give the C$_{1-5}$ acyloxy group of Compound (M) using a method known in the art, for example, an alkyl acid chloride in the presence of -continued

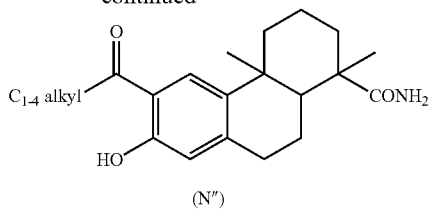

(N″)

Another method of preparing compounds of the invention can be through the Friedel-Crafts Acylation reaction. By way of example, Compound (A) can be acylated using a $C_{1-5}$ acylhalide in the presence of a Lewis Acid, such as $AlCl_3$ and the like to give Compound (O). In the example where an acetylhalide is used in this reaction, the resulting compound is Acetophenone (P). Representative examples are shown below:

can be readily converted to a number of groups using amidation or esterification methods known in the art to give, for example, carboxamide, $C_{1-4}$ alkylcarboxamide, $C_{2-6}$ dialkylcarboxamide, and carbo-$C_{1-6}$-alkoxy. In another example, the carbonyl group in Compounds (O) or (P) can be reduced with, for example, Zn(Hg)/HCl, $NH_2NH_2$/base, and the like to give the alkyl group. In another example, Compound (H) where $R_3$=Br or I, or Compound S as a triflate (—$OSO_2CF_3$), can be converted to a $C_{2-6}$ alkenyl (Compound (Q)), $C_{1-6}$ alkyl (Compound (R)), or $C_{2-4}$ alkynyl (Compound (S)) group using coupling methods known in the art, for example, the Heck Reaction, Suzuki Reaction, Stille Reaction, Sonogashira Coupling and the like; suitable catalysts include Pd(O-$COCH_3)_2$, $PdCl_2$, Pd(dba)$_3$, Pd(PPh$_3$)$_4$, $PhCH_2Pd$, Pd(dppf)$Cl_2$, $PhCH_2Pd(PPh_3)_2Cl_2$, and the like, other ligands (i.e. L) that are also suitable include $PAr_3$, dppp, binap and the like,

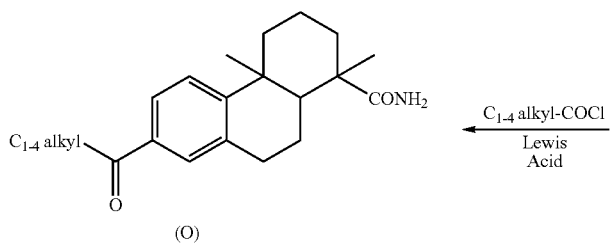

(O)

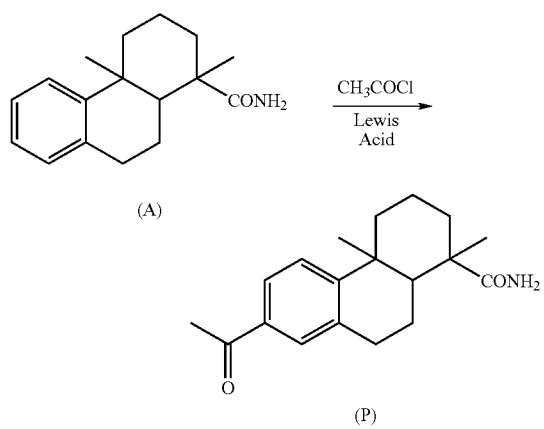

(A)

(P)

Further, Compound (P) can be oxidized to give the corresponding carboxyl group using methods in the art, for example, KOCl, KOI, KOBr, and the like. The carboxyl group typically these coupling reactions include the use of a base, for example, TEA, $Na_2CO_3$, $K_2CO_3$, $NaOCOCH_3$, $K_3PO_4$, TlOH, $NaOCH_2CH_3$, and the like.

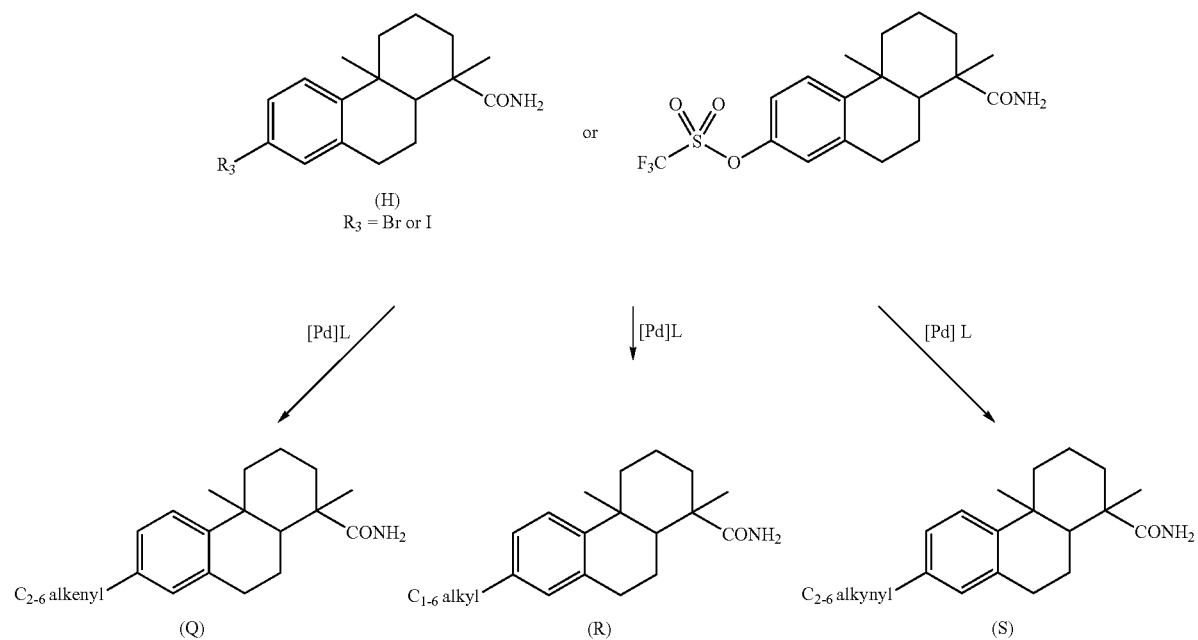

Another method includes sulfonating the aromatic ring. For example, Compound (A) can be reacted with chlorosulfonylchloride to give Compound (T). Other suitable methods are know in art, for example, $H_2SO_4/SO_3$ to give the sulfonic acid which in turn can be converted to Compound (T). A variety of amines can be allowed to react with Compound (T), for example $C_{1-4}$ alkylamines to give the $C_{1-4}$ alkylsulfonamide group of Compound (U).

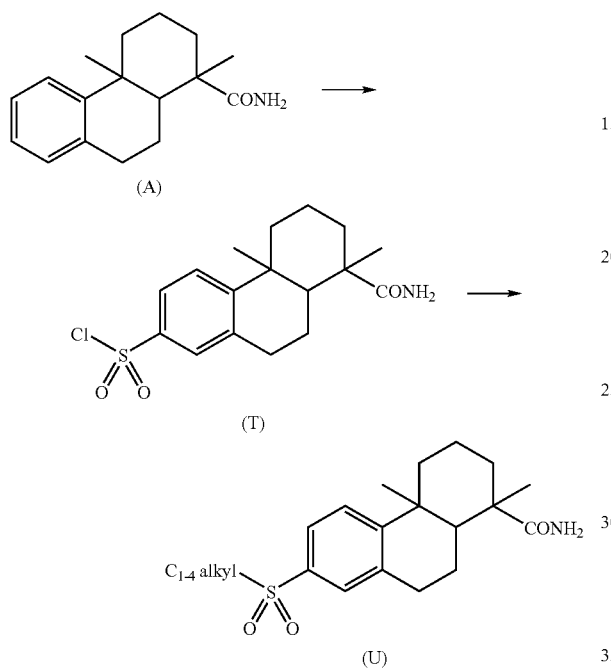

It is understood that various protecting schemes may be needed during the course of preparing compounds of the invention. The term "protected derivative", as defined herein, refers to a molecule where at least one chemical group that is part of the molecule has been changed so as to render this group essentially stable during a synthetic step. One example can be the carboxamide group at C(1) that may need to be protected, converted to a different functional group, or converted to a different functional group and further protected during the course of a synthesis. The "protecting" of the carboxamide or the group that can be converted into the carboxamide at C(1) renders the carboxamide or the group essentially stable to the reaction conditions used in modifying the aromatic ring and is subsequently "deprotected" or "deprotected and reconverted" upon completion of the reaction back to the carboxamide.

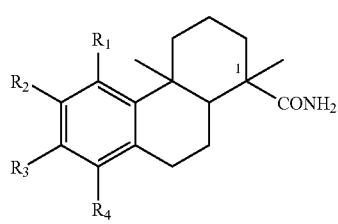

Accordingly, representative protecting groups that are suitable for a wide variety of synthetic transformations are disclosed in Greene and Wuts, *Protective Groups in Organic Synthesis,* 3rd edition, John Wiley & Sons, New York, 1999, the disclosure of which is incorporated herein by reference in its entirety.

References for other synthetic procedures that can be utilized for the preparation of intermediates or compounds disclosed herein can be found in, for example, Smith, M. B.; and March, J., *Advanced Organic Chemistry,* 5$^{th}$ Edition, Wiley-Interscience (2001); or Larock, R. C., *Comprehensive Organic Transformations, A Guide to Functional Group Preparations,* 2$^{nd}$ Edition, VCH Publishers, Inc. (1999), both citations are incorporated herein by reference in their entirety.

Although the above synthetic illustrations show one isomer, it is understood that they are merely illustrative and that there may be more than one regioisomer formed from any given reaction. For example, the nitration of Compound (A) can give more than one regioisomer as shown below:

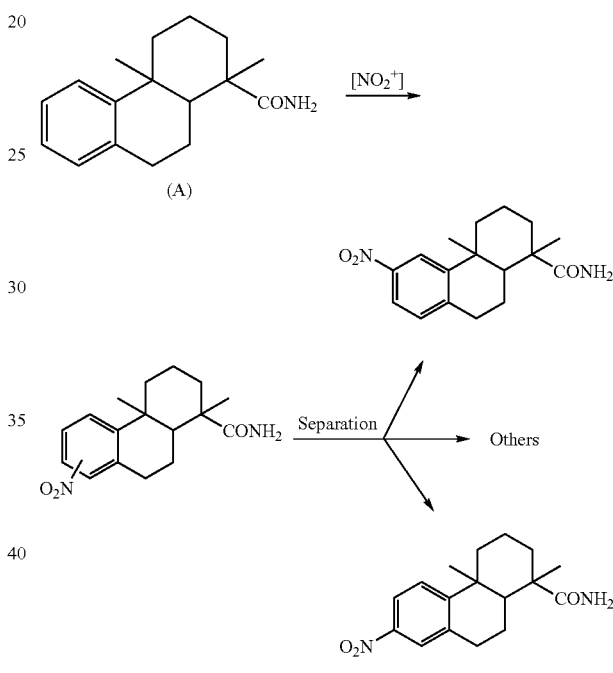

Separation of regioisomers can be conducted by chromatography, for example but not limited to, flash chromatography, low pressure chromatography, HPLC and the like; fractional crystallization; and other methods which are well known to practitioners in the art. It is understood that a variety of conditions exist in the literature that can influence the ratio of regioisomers, for example, solvent, temperature, presence or absence of catalyst, presence of electron-withdrawing or donating group(s), and the like.

The synthetic procedure and method examples for the preparation of the compounds of the present invention are understood to be representative and in no way limited to the specific details as other variations thereof will be known, or apparent in light of the instant disclosure, to one of ordinary skill in the art.

Various reactions, including electrophilic aromatic substitutions reaction and coupling reactions as described herein, can be improved through the use of microwave technology. Accordingly, reactions described herein can be assisted through the use of microwave irradiation. Irradiation with microwaves may be generated from a number of different microwaves sources. One particularly useful instrument in generating microwaves used in organic synthesis is the Smith Synthesizer and related instruments from Personal Chemistry AB, Uppsala Sweden.

Additionally, compounds of Formula (I) encompass all pharmaceutically acceptable salts, solvates and particularly hydrates thereof. The present invention also encompasses diastereomers as well as optical isomers, e.g. mixtures of enantiomers including racemic mixtures, as well as individual enantiomers and diastereomers, which arise as a consequence of structural asymmetry in certain compounds of Formula (I). Separation of the individual isomers can be obtained via chromatography, including chiral chromatography, chiral resolution through the use of a chiral acid or base, or via various other methods which are well known to practitioners in the art. More specifically, racemic mixtures can be resolved into the optical pure enantiomers by known methods, for example, by separation of diastereomeric salts thereof with an optically active acid, and liberating the optically active amine compound by treatment with a base. Similarly, racemic mixtures can be resolved by separation of diastereomeric salts thereof with an optically active base, and liberating the optically active acid compound by treatment with an acid. Another method for resolving racemates into the optical pure enantiomers is based upon chromatography on an optically active matrix or chiral support. Certain racemic compounds of the present invention can thus be resolved into their optical antipodes, e.g., by fractional crystallization of d- or l-(tartrates, mandelates, or camphorsulphonate) salts for example. The compounds of the present invention may also be resolved by the formation of diastereomeric amides or esters by reaction of the compounds of the present invention with an optically active amine or alcohol such as that derived from (+) or (−) α-methylbenzylamine or the like, separated via fractional recrystallization, chiral chromatography or similar method, and subsequently hydrolyzed.

Additional methods for the resolution of optical isomers known to those skilled in the art can be used and will be apparent to the average worker skilled in the art. Such methods include those discussed by J. Jaques, A. Collet, and S. Wilen in "Enantiomers, Racemates, and Resolutions", John Wiley and Sons, New York (1981).

It is understood that the chemistry described herein is representative and is not intended to be limiting in any manner.

Representative examples of compound of the invention are shown below in TABLE 1.

TABLE 1

| Cmpd | Chemical Structure | Chemical Name |
|---|---|---|
| 1 | 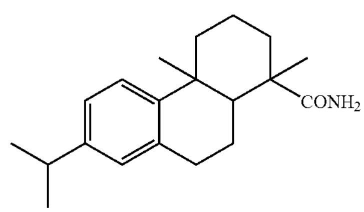 | 7-Isopropyl-1,4a-dimethyl-1,2,3,4,4a,9,10,10a-octahydro-phenanthrene-1-carboxylic acid amide |
| 2 | 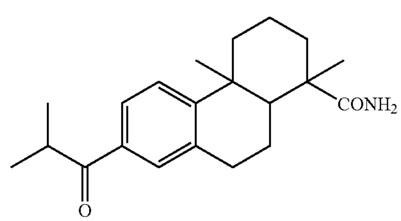 | 7-Isobutyryl-1,4a-dimethyl-1,2,3,4,4a,9,10,10a-octahydro-phenanthrene-1-carboxylic acid amide |
| 3 | 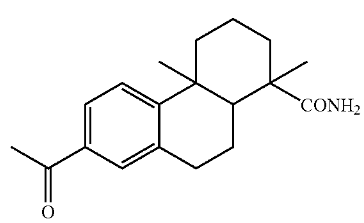 | 7-Acetyl-1,4a-dimethyl-1,2,3,4,4a,9,10,10a-octahydro-phenanthrene-1-carboxylic acid amide |
| 4 | 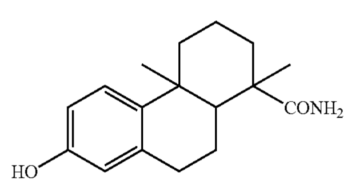 | 7-Hydroxy-1,4a-dimethyl-1,2,3,4,4a,9,10,10a-octahydro-phenanthrene-1-carboxylic acid amide |

TABLE 1-continued

| Cmpd | Chemical Structure | Chemical Name |
| --- | --- | --- |
| 5 | 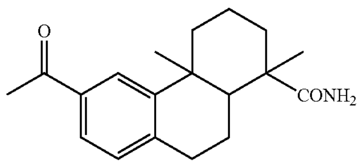 | 6-Acetyl-1,4a-dimethyl-1,2,3,4,4a,9,10,10a-octahydro-phenanthrene-1-carboxylic acid amide |
| 6 | 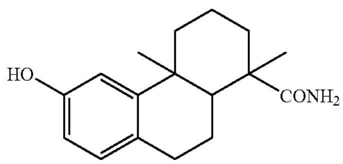 | 6-Hydroxy-1,4a-dimethyl-1,2,3,4,4a,9,10,10a-octahydro-phenanthrene-1-carboxylic acid amide |
| 7 | 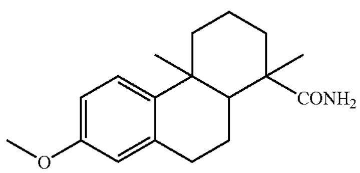 | 7-Methoxy-1,4a-dimethyl-1,2,3,4,4a,9,10,10a-octahydro-phenanthrene-1-carboxylic acid amide |
| 8 | 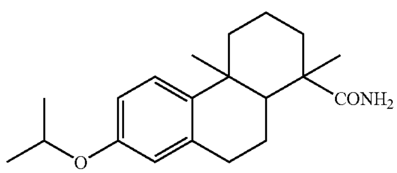 | 7-Isopropoxy-1,4a-dimethyl-1,2,3,4,4a,9,10,10a-octahydro-phenanthrene-1-carboxylic acid amide |
| 9 | 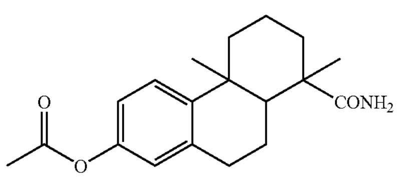 | Acetic acid 8-carbamoyl-4b,8-dimethyl-4b,5,6,7,8,8a,9,10-octahydro-phenanthren-2-yl ester |
| 10 | 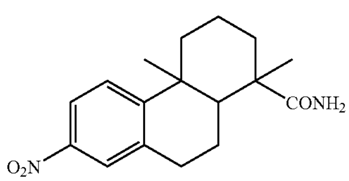 | 1,4a-Dimethyl-7-nitro-1,2,3,4,4a,9,10,10a-octahydro-phenanthrene-1-carboxylic acid amide |
| 11 | 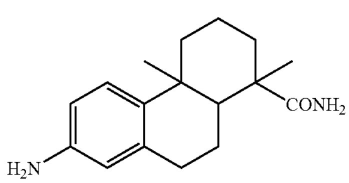 | 7-Amino-1,4a-dimethyl-1,2,3,4,4a,9,10,10a-octahydro-phenanthrene-1-carboxylic acid amide |
| 12 | 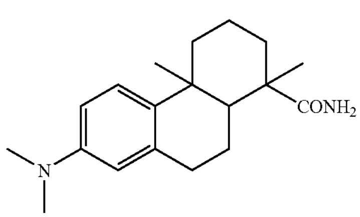 | 7-Dimethylamino-1,4a-dimethyl-1,2,3,4,4a,9,10,10a-octahydro-phenanthrene-1-carboxylic acid amide |

TABLE 1-continued

| Cmpd | Chemical Structure | Chemical Name |
| --- | --- | --- |
| 13 | 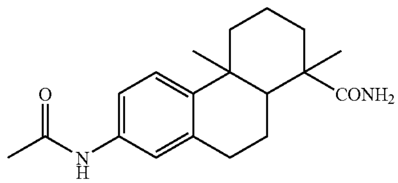 | 7-Acetylamino-1,4a-dimethyl-1,2,3,4,4a,9,10,10a-octahydro-phenanthrene-1-carboxylic acid amide |
| 14 | 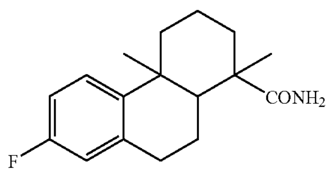 | 7-Fluoro-1,4a-dimethyl-1,2,3,4,4a,9,10,10a-octahydro-phenanthrene-1-carboxylic acid amide |
| 15 | 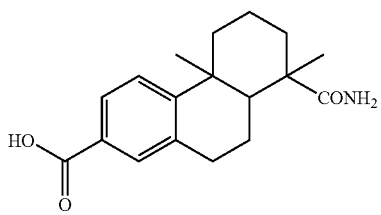 | 8-Carbamoyl-4b,8-dimethyl-4b,5,6,7,8,8a,9,10-octahydro-phenanthrene-2-carboxylic acid |
| 16 | 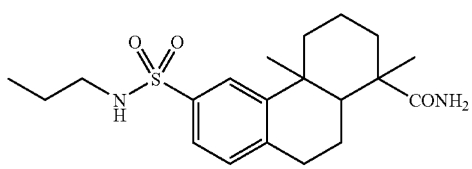 | 1,4a-Dimethyl-6-propylsulfamoyl-1,2,3,4,4a,9,10,10a-octahydro-phenanthrene-1-carboxylic acid amide |
| 17 | 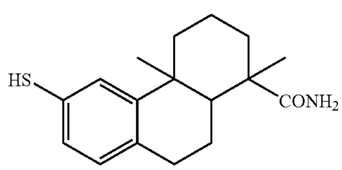 | 6-Mercapto-1,4a-dimethyl-1,2,3,4,4a,9,10,10a-octahydro-phenanthrene-1-carboxylic acid amide |
| 18 | 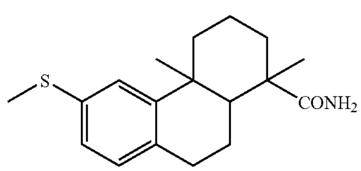 | 1,4a-Dimethyl-6-methylsulfanyl-1,2,3,4,4a,9,10,10a-octahydro-phenanthrene-1-carboxylic acid amide |
| 19 | 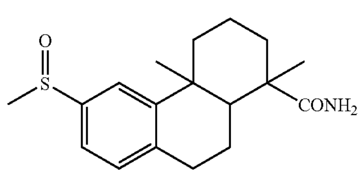 | 6-Methanesulfinyl-1,4a-dimethyl-1,2,3,4,4a,9,10,10a-octahydro-phenanthrene-1-carboxylic acid amide |
| 20 | 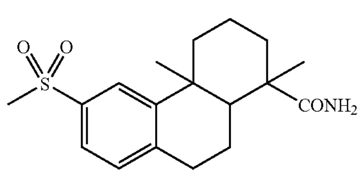 | 6-Methanesulfonyl-1,4a-dimethyl-1,2,3,4,4a,9,10,10a-octahydro-phenanthrene-1-carboxylic acid amide |

TABLE 1-continued

| Cmpd | Chemical Structure | Chemical Name |
|---|---|---|
| 21 | 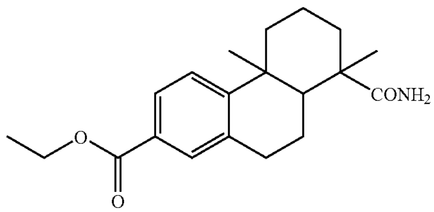 | 8-Carbamoyl-4b,8-dimethyl-4b,5,6,7,8,8a,9,10-octahydro-phenanthrene-2-carboxylic acid ethyl ester |
| 22 | 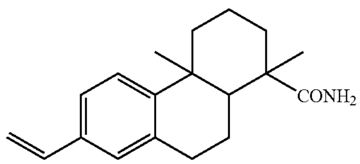 | 1,4a-Dimethyl-7-vinyl-1,2,3,4,4a,9,10,10a-octahydro-phenanthrene-1-carboxylic acid amide |
| 23 | 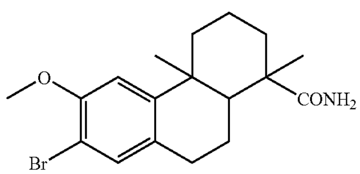 | 7-Bromo-6-methoxy-1,4a-dimethyl-1,2,3,4,4a,9,10,10a-octahydro-phenanthrene-1-carboxylic acid amide |
| 24 | 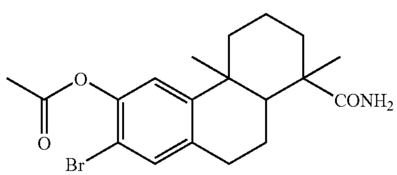 | Acetic acid 2-bromo-8-carbamoyl-4b,8-dimethyl-4b,5,6,7,8,8a,9,10-octahydro-phenanthren-3-yl ester |
| 25 | 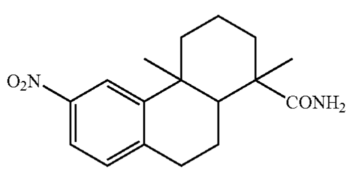 | 1,4a-Dimethyl-6-nitro-1,2,3,4,4a,9,10,10a-octahydro-phenanthrene-1-carboxylic acid amide |
| 26 | 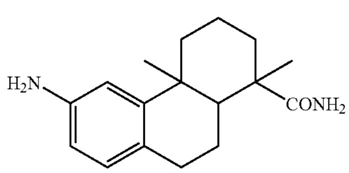 | 6-Amino-1,4a-dimethyl-1,2,3,4,4a,9,10,10a-octahydro-phenanthrene-1-carboxylic acid amide |
| 27 | 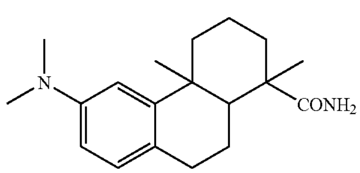 | 6-Dimethylamino-1,4a-dimethyl-1,2,3,4,4a,9,10,10a-octahydro-phenanthrene-1-carboxylic acid amide |
| 28 | 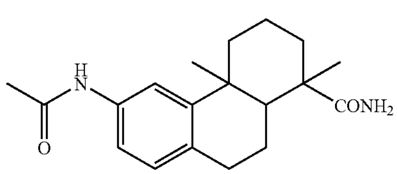 | 6-Acetylamino-1,4a-dimethyl-1,2,3,4,4a,9,10,10a-octahydro-phenanthrene-1-carboxylic acid amide |

TABLE 1-continued

| Cmpd | Chemical Structure | Chemical Name |
|---|---|---|
| 29 | 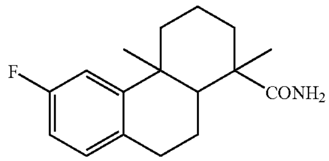 | 6-Fluoro-1,4a-dimethyl-1,2,3,4,4a,9,10,10a-octahydro-phenanthrene-1-carboxylic acid amide |
| 30 | 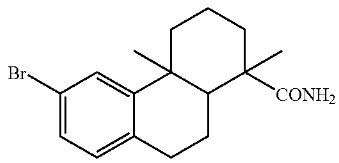 | 6-Bromo-1,4a-dimethyl-1,2,3,4,4a,9,10,10a-octahydro-phenanthrene-1-carboxylic acid amide |
| 31 | 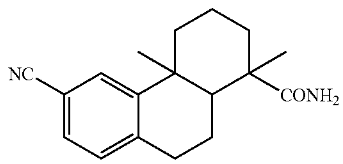 | 6-Cyano-1,4a-dimethyl-1,2,3,4,4a,9,10,10a-octahydro-phenanthrene-1-carboxylic acid amide |
| 32 | 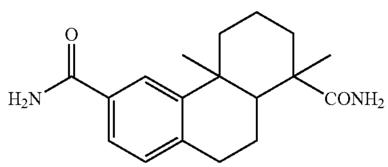 | 1,4a-Dimethyl-1,2,3,4,4a,9,10,10a-octahydro-phenanthrene-1,6-dicarboxylic acid diamide |
| 33 | 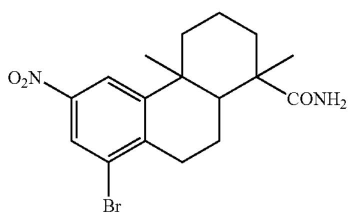 | 8-Bromo-1,4a-dimethyl-6-nitro-1,2,3,4,4a,9,10,10a-octahydro-phenanthrene-1-carboxylic acid amide |
| 34 | 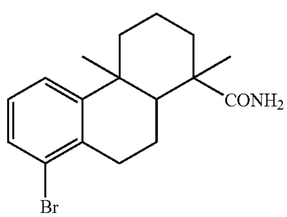 | 8-Bromo-1,4a-dimethyl-1,2,3,4,4a,9,10,10a-octahydro-phenanthrene-1-carboxylic acid amide |

G. Pharmaceutical Compositions

The invention provides methods of treatment (and prevention) by administration to an individual in need of said treatment (or prevention) a therapeutically effect amount of a modulator of the invention [also see, e.g., PCT Application Number PCT/IB02/01461 published as WO 02/066505 on 29 Aug. 2002; the disclosure of each of which is hereby incorporated by reference in its entirety]. In a preferred aspect, the modulator is substantially purified. The individual is preferably an animal including, but not limited to animals such as cows, pigs, horses, chickens, cats, dogs, rabbits, rats, mice, etc., and is preferably a mammal, and most preferably human.

Modulators of the invention can be administered to non-human animals [see Examples, infra] and/or humans, alone or in pharmaceutical or physiologically acceptable compositions where they are mixed with suitable carriers or excipient(s) using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

The pharmaceutical or physiologically acceptable composition is then provided at a therapeutically effective dose. A therapeutically effective dose refers to that amount of a modulator sufficient to result in prevention or amelioration of symptoms or physiological status of cell death-related disorders or disorders of neuronal cell death or muscle cell death as determined illustratively and not by limitation by the methods described herein.

It is expressly considered that the modulators of the invention may be provided alone or in combination with other pharmaceutically or physiologically acceptable compounds.

Other compounds for the treatment of disorders of the invention are currently well known in the art. One aspect of the invention encompasses the use according to embodiments disclosed herein further comprising one or more agents selected from the group consisting of donepezil, rivastigmine, galantamine, tacrine, piracetam aniracetamn, *ginkgo biloba*, nicergoline, minodipine, memantine, risperidone, olanzapine, haloperidol, paroxetine, citalopram, fluoxetine, fluvoxamine, sertaline, trazodone and tiapride. In some embodiments, the agent is selected from the group consisting of levodopa, levodopa-carbidopa, levodopa-benserazide, bromocriptine, pergolide, lisuride, cabergoline, pramipexole, ropinirole, talipexole, apomorphine, entacapone, tolcapone, selegiline, trihexyphenidyl, benztropine, biperiden, arantadine and budipine. In some embodiments, the agent is selected from the group consisting of amiloride hydrochloride, spironolactone, atenolol, bisoprolol, carvekilol, metoprolol tartrate and digoxin.

In some embodiments the cell death-related disorder is a neuronal cell death-related disorder selected from the group consisting of Alzheimer's disease, Parkinson's disease, prion-associated disease, stroke, motor-neuron disease, learning or memory impairment, traumatic brain injury, spinal cord injury, and peripheral neuropathy. In some embodiments, Alzheimer's disease encompasses mild cognitive impairment (MCI). Motor neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy.

In some embodiments the cell death-related disorder is a muscle cell death-related disorder selected from the group consisting cerebral amyloid angiopathy, myocardial infarction, and congestive heart failure.

Routes of Administration

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated. In certain embodiments, route of administration is oral.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carrier and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsule made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in multi-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a particular embodiment, the compounds can be delivered via a controlled release system. In one embodiment, a pump may be used (Langer, supra; Se-ton, 1987, CRC Crit. Ref. Biomed. Eng. 14:201-240; Buchwald et al., 1980, Surgery 88:507-516; Saudek et al., 1989, N. Engl. J. Med. 321: 574-579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, New York, 1984; Ranger and Peppas, 1983, Macromol. Sci. Rev. Macromol. Chem. 23:61; Levy et al., 1985, Science 228:190-192; During et al., 1989, Ann. Neurol. 25:351-356; Howard et al., 1989, J.

Neurosurg. 71:858-863). Other controlled release systems are discussed in the review by Langer (1990, Science 249: 1527-1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or recipients include but are not limited to calcium carbonate, calcium phosphate, various sugars, starches, cellulose derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to cell death-protective in an in vitro system. [See Examples, infra, for in vitro assays and in vivo animal models.] Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the test population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to prevent or treat a disorder of the invention, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10-90% of the time, preferably between 30-99%, and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results, including but not limited to reduction of neuronal cell death or prevention of or treatment for muscle cell death, is 0.1-100 mg/kg body mass. Other preferred dosage range is 0.1-30 mg/kg body mass. Other preferred dosage range is 0.1-10 mg/kg body mass. Other preferred dosage range is 0.1-3.0 mg/kg body mass. Of course, these daily dosages can be delivered or administered in small amounts periodically during the course of a day. It is noted that these dosage ranges are only preferred ranges and are not meant to be limiting to the invention.

H. Methods of Treatment

The invention is drawn inter alia to methods of reducing cell death-related disorders, particularly neuronal cell death-related disorders and muscle cell death-related disorders, comprising providing an individual in need of such treatment with a modulator of the invention. In some embodiments, said modulator is orally bioavailable. In some embodiments, said orally bioavailable modulator is further able to cross the blood-brain barrier. In certain embodiments, the modulator is provided to the individual in a pharmaceutical or physiologically acceptable composition that is taken orally. In certain embodiments, the individual is a mammal. In certain embodiments, the individual or mammal is a human.

In certain embodiments, the cell death-related disorder is a neuronal cell death-related disorder. In certain embodiments, said neuronal cell death-related disorder is selected from the group consisting of Alzheimer's disease, Parkinson's disease, prion-associated disease, stroke, motor-neuron disease, learning or memory impairment, traumatic brain injury, spinal cord injury, and peripheral neuropathy. In some embodiments, Alzheimer's disease encompasses mild cognitive impairment (MCI). Motor-neuron disease includes, but is not limited to, amyotrophic lateral sclerosis, progressive spinal muscular atrophy, progressive bulbar palsy, and primary lateral sclerosis. Peripheral neuropathy includes, but is not limited to, diabetic neuropathy and neuropathy involving the sciatic nerve. Diabetic neuropathy includes, but is not limited to, distal symmetrical polyneuropathy (DSP).

In certain embodiments, the cell death-related disorder is a muscle cell death-related disorder. In certain embodiments, said muscle cell death-related disorder is selected from the group consisting of cerebral amyloid angiopathy, myocardial infarction, and congestive heart failure.

The invention is also drawn inter alia to methods of preventing or treating cell proliferative disorders, particularly neuronal cell proliferative disorders and muscle cell proliferative disorders, comprising providing an individual in need of such treatment with a modulator of the invention. Preferably said modulator is orally bioavailable. In some embodiments, it is preferable that said orally bioavailable modulator is further able to cross the blood-brain barrier. Preferably the modulator is provided to the individual in a pharmaceutical composition that is preferably taken orally. Preferably the individual is a mammal, and most preferably a human.

In certain embodiments, the cell proliferative disorder is a neuronal cell proliferative disorder. In certain embodiments, said neuronal cell proliferative disorder is neuroblastoma. In other embodiments, said neuronal cell proliferative disorder is medulloblastoma.

In certain embodiments, the cell proliferative disorder is a muscle cell proliferative disorder. In certain embodiments, said muscle cell proliferative disorder is selected from the group consisting of atherosclerosis, restenosis, and tumor-supportive angiogenesis.

I. Other Utility

Agents that modulate (i.e., increase, decrease, or block) FPRL2 Humanin receptor functionality may be identified by contacting a candidate compound with an FPRL2 Humanin receptor and determining the effect of the candidate compound on FPRL2 Humanin receptor functionality. The selectivity of a compound that modulates the functionality of the FPRL2 Humanin receptor can be evaluated by comparing its effects on the FPRL2 Humanin receptor to its effects on other G protein-coupled receptors. Following identification of compounds that modulate FPRL2 Humanin receptor functionality, such candidate compounds may be further tested in other assays including, but not limited to, in vivo models, in order to confirm or quantitate their activity. Modulators of FPRL2 Humanin receptor functionality are therapeutically useful in treatment of diseases and physiological conditions in which normal or aberrant FPRL2 Humanin receptor functionality is involved.

Agents that are ligands of FPRL2 Humanin receptor may be identified by contacting a candidate compound with an FPRL2 Humanin receptor and determining whether the candidate compound binds to the FPRL2 Humanin receptor. The selectivity of a compound that binds to the FPRL2 Humanin receptor can be evaluated by comparing its binding to the FPRL2 Humanin receptor to its binding on other receptors. Ligands that are modulators of FPRL2 Humanin receptor functionality are therapeutically useful in treatment of diseases and physiological conditions in which normal or aberrant FPRL2 Humanin receptor functionality is involved.

The present invention also relates to radioisotope-labeled versions of compounds of the invention identified as modulators or ligands of Humanin receptor that would be useful not only in radio-imaging but also in assays, both in vitro and in vivo, for localizing and quantitating FPRL2 Humanin receptor in tissue samples, including human, and for identifying FPRL2 Humanin receptor ligands by inhibition binding of a radioisotope-labeled compound. It is a further object of this invention to develop novel FPRL2 Humanin receptor assays which comprise such radioisotope-labeled compounds.

The present invention embraces radioisotope-labeled versions of compounds of the invention identified as modulators or ligands of FPRL2 Humanin receptor.

The present invention also relates to radioisotope-labeled versions of test ligands that are useful for detecting a ligand bound to FPRL2 Humanin receptor. In some embodiments, the present invention expressly contemplates a library of said radiolabeled test ligands useful for detecting a ligand bound to the FPRL2 Humanin receptor. In certain embodiments, said library comprises at least about 10, at least about $10^2$, at least about $10^3$, at least about $10^5$, or at least about $10^6$ said radiolabeled test compounds. It is a further object of this invention to develop novel FPRL2 Humanin receptor assays which comprise such radioisotope-labeled test ligands.

In some embodiments, a radioisotope-labeled version of a compound is identical to the compound, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{7}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro FPRL2 Humanin receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$C]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I A represented procedure was reported by Zhu, D.-G. and co-workers in J. Org. Chem. 2002, 67, 943-948.

B. Ortho $^{125}$Iodination of phenols—This procedure allows for the incorporation of $^{125}$I at the ortho position of a phenol as reported by Collier, T. L. and co-workers in J. Labeled Compd Radiopharm. 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn (CH$_3$)$_3$]. A represented procedure was reported by Bas, M.-D. and co-workers in *J. Labeled Compd Radiopharm.* 2001, 44, S280-S282.

In some embodiments, a radioisotope-labeled version of a compound is identical to the compound, but for the addition of one or more substituents comprising a radionuclide. In some further embodiments, the compound is a polypeptide. In some further embodiments, the compound is an antibody or an antigen-binding fragment thereof. In some further embodiments, said antibody is monoclonal. Suitable said radionuclide includes but is not limited to $^2$H (deuterium), $^3$H (tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compound will depend on the specific application of that radio-labeled compound. For example, for in vitro FPRL2 Humanin receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful. In some embodiments, the radionuclide is selected from the group consisting of $^3$H, $^{11}$C, $^{18}$F, $^{14}$C, $^{125}$I, $^{124}$I, $^{131}$I, $^{35}$S and $^{82}$Br.

Methods for adding one or more substituents comprising a radionuclide are within the purview of the skilled artisan and include, but are not limited to, addition of radioisotopic iodine by enzymatic method [Marchalonic J J, Biochemical Journal (1969) 113:299-305; Thorell J I and Johansson B G, Biochimica et Biophysica Acta (1969) 251:363-9; the disclosure of each of which is hereby incorporated by reference in its entirety] and or by Chloramine-T/Iodogen/Iodobead methods [Hunter W M and Greenwood F C, Nature (1962) 194: 495-6; Greenwood F C et al., Biochemical Journal (1963) 89:114-23; the disclosure of each of which is hereby incorporated by reference in its entirety].

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. The mutational approach disclosed herein does not rely upon this approach but is instead based upon an algorithmic approach and a positional distance from a conserved proline residue located within the TM6 region of human GPCRs. Once this approach is secured, those in the art are credited with the ability to make minor modifications thereto to achieve substantially the same results (i.e., constitutive activation) disclosed herein. Such modified approaches are considered within the purview of this disclosure.

The following Examples are provided for illustrative purposes and not as a means of limitation. One of ordinary skill in the art would be able to design equivalent assays and methods based on the disclosure herein, all of which form part of the present invention.

Recombinant DNA techniques relating to the subject matter of the present invention and well known to those of ordinary skill in the art can be found, e.g, in Maniatis T et al., *Molecular Cloning: A Laboratory Manual* (1989) Cold Spring Harbor Laboratory; U.S. Pat. No. 6,399,373; and PCT Application Number PCT/IB02/01461 published as WO 02/066505 on 29 Aug. 2002; the disclosure of each of which is hereby incorporated by reference in its entirety.

Example 1

Full-Length Cloning of Human GPCRs a. Endogenous Human FPRL2 (SEQ ID NOs:1 & 2)

Polynucleotide sequence encoding full-length FPRL2 (GenBank® Accession No. L14061) was cloned as described here. SEQ ID NO:1 is human FPRL2 polynucleotide coding sequence. SEQ ID NO:2 is the encoded FPRL2 polypeptide. Those in the art are credited with the ability to make minor modification of the experimental protocol presented here in order to analogously clone endogenous human FPRL1 (GenBank® Accession No. AF054013) polynucleotide and endogenous human FPR (GenBank® Accession No. M60627) polynucleotide.

PCR was performed using genomic DNA as template and rTth polymerase (Perkin Elmer) with the buffer system provided by the manufacturer, 0.25 mM of each primer, and 0.2 mM of each 4 nucleotides. The cycle condition was 30 cycles of 94° C. for 1 min, 64° C. for 1 min and 72° C. for 1 min and 20 sec.

The 5' PCR primer contains an EcoRI site with the sequence:

5'-AAAGAATTCAGGTGTGGGAAGATGGAAACC-3'. (SEQ ID NO:3)

The 3' primer contains a BamHI site with the sequence:

5'-AAAGGATCCCCGACCTCACATTGCTTGTA-3'. (SEQ ID NO:4)

The 1.1 kb PCR fragment was digested with EcoRI and 3BamHI and cloned into EcoRI-BamHI site of pCMV expression vector.

b. HA/V5 Double Tagged Endogenous Human FPRL2 (SEQ ID NOs:5 & 6)

Polynucleotide encoding full-length FPRL2 polypeptide with N-terminal HA epitope tag and C-terminally disposed V5 epitope tag was cloned as follows. HA epitope tag is amino acid sequence MYPYDVPDYA; V5 epitope tag is amino acid sequence GKPIPNPLLGLDST. SEQ ID NO:5 is human FPRL2 polynucleotide coding sequence with 5'-terminal HA epitope tag and 3' disposed V5 epitope tag. SEQ ID NO:6 is the encoded HA/V5 double tagged FPRL2 polypeptide. Those in the art are credited with the ability to make minor modification of the experimental protocol presented here in order to analogously clone HA/V5 double tagged endogenous human FPRL1 (GenBank® Accession No. AF054013) polynucleotide and HA/V5 double tagged endogenous human FPR (GenBank® Accession No. M60627) polynucleotide.

PCR was performed using the cloned FPRL2 polynucleotide of (a) above as template and pfu polymerase (Stratagene) with the buffer system provided by the manufacturer supplemented with 10% DMSO, 0.25 mM of each primer, and 0.5 mM of each 4 nucleotides. The cycle condition was 25 cycles of 94° C. for 1 min, 60° C. for 1 min and 72° C. for 2 min.

The 5' PCR primer contains a HindIII site with the sequence:

(SEQ ID NO:7)
5'-CCCAAGCTTCATGGAACCAACTTCTCCATTCCTC-3'.

The 3' primer contains a BamHI site with the sequence:

(SEQ ID NO:8)
5'-CCCGGATCCCATTGCTTGTAACTCCGTCTCCTC-3'.

The 1.06 kb PCR fragment was digested with HindIII and BamHI and cloned into HindIII-BamHI site of HA/V5 double tagged pCMV expression vector.

Example 2

Preparation of Non-Endogenous, Constitutively Activated Human FPRL2 (SEQ ID NOS:11&12)

Those skilled in the art are credited with the ability to select techniques for mutation of a nucleic acid sequence. Presented below are approaches utilized to create non-endogenous versions of human GPCRs. The mutation disclosed below for FPRL2 is based upon an algorithmic approach whereby the $16^{th}$ amino acid (located in the IC3 region of the GPCR) from a conserved proline (or an endogenous, conservative substitution therefor) residue (located in the TM6 region of the GPCR, near the TM6/IC3 interface) is mutated, preferably to an alanine, histidine, arginine or lysine amino acid residue, most preferably to a lysine amino acid residue.

Non-endogenous, constitutively activated human FPRL2 was accomplished by mutation of the leucine residue at amino acid position 240 to lysine (L240K), using the sequence primers:

5'-TCCAGCCGTCCC<u>AAA</u>CGTGTCTTGGCTGG-3'; (SEQ ID NO:9)

the mutation sequence is underlined) and (SEQ ID NO:10)
5'-CTCCTTCGGTCCTCCTATCGTTGTCAGAAGT-3'.

SEQ ID NO:11 is nonendogenous, constitutively activated (L240K) FPRL2 polynucleotide coding sequence. SEQ ID NO:12 is the encoded non-endogenous, constitutively activated (L240K) FPRL2 polypeptide. See, e.g., PCT Application Number PCT/US02/05625 published as WO02068600 on 6 Sep. 2002, the disclosure of which is hereby incorporated by reference in its entirety).

1. Transformer Site-Directed™ Mutagenesis

Preparation of Non-Endogenous Human GPCRs May be Accomplished on human GPCRs using, inter alia, Transformer Site-Directed™ Mutagenesis Kit (Clontech) according to the manufacturer instructions. Two mutagenesis primers are utilized, most preferably a lysine mutagenesis oligonucleotide that creates the lysine mutation, and a selection marker oligonucleotide. For convenience, the codon mutation to be incorporated into the human GPCR is also noted, in standard form.

2. QuikChange™ Site-Directed™ Mutagenesis

Preparation of Non-Endogenous Human GPCRs can Also be Accomplished by using QuikChange™ Site-Directed™ Mutagenesis Kit (Stratagene, according to manufacturer's instructions). Endogenous GPCR is preferably used as a template and two mutagenesis primers utilized, as well as, most preferably, a lysine mutagenesis oligonucleotide and a selection marker oligonucleotide (included in kit). For convenience, the codon mutation incorporated into the novel human GPCR and the respective oligonucleotides are noted, in standard form.

Example 3

Receptor Expression

Although a variety of cells are available to the art for the expression of proteins, it is most preferred that mammalian cells or melanophores be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells or melanophores. Of the mammalian cells, CHO, COS-7, MCB3901, 293 and 293T cells are particularly preferred, although the specific mammalian cell utilized can be predicated upon the particular needs of the artisan. In some embodiments, cardiomyocytes are preferred. See infra as relates to melanophores, including Example 11.

a. Transient Transfection

On day one, $6 \times 10^6$/10 cm dish of 293 cells are were plated out. On day two, two reaction tubes are prepared (the proportions to follow for each tube are per plate): tube A is prepared by mixing 4 μg DNA (e.g., pCMV vector; pCMV vector with receptor cDNA, etc.) in 0.5 ml serum free DMEM (Gibco BRL); tube B is prepared by mixing 24 μl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1×PBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 μg of DNA (e.g. pCMV vector with receptor cDNA). The 12 μg of DNA is combined with 60 μl of lipofectamine and 2 mL of DME High Glucose Medium without serum. The medium is aspirated from the plates and the cells are washed once with medium without serum. The DNA, lipofectamine, and medium mixture are added to the plate along with 10 mL of medium without serum. Following incubation at 37 degrees Celsius for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 μg of DNA (e.g., pCMV vector with receptor cDNA). The 12 μg of DNA is combined with 60 μl of lipofectamine and 2 mL of DME High Glucose Medium without serum. The medium is aspirated from the plates and the cells are washed once with medium without serum. The DNA, lipofectamine, and medium mixture are added to the plate along with 10 mL of medium without serum. Following incubation at 37 degrees Celsius for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 μg/mL. The transfected cells now undergo selection for positively transfected cells containing the G418 resistance gene. The medium is replaced every four to five days as selection occurs. During selection, cells are grown to create stable pools, or split for stable clonal selection.

Example 4

Assays for Determination of GPCR Activation

A variety of approaches are available for assessment of activation of human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to endogenous GPCRs and non-endogenous, constitutively activated GPCRs. The assay is generic and has application to drug discovery at all G protein-coupled receptors.

The [$^{35}$S]GTPγS assay is incubated in 20 mM HEPES and between 1 and about 20 mM MgCl$_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 μg membrane protein (e.g, 293 cells expressing the Gs Fusion Protein; this amount can be adjusted for optimization) and 10 μM GDP (this amount can be changed for optimization) for 1 hour. Wheatgerm agglutinin beads (25 μl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 min. The cell pellet is carefully re-suspended into an appropriate volume of PBS (about 3 ml/plate). The cells are then counted using a hemocytometer and additional PBS is added to give the appropriate number of cells (with a final volume of about 50 μl/well).

cAMP standards and Detection Buffer (comprising 1 μCi of tracer [$^{125}$I cAMP (50 μl] to 11 ml Detection Buffer) is prepared and maintained in accordance with the manufacturer's instructions. Assay Buffer is prepared fresh for screening and contains 50 μl of Stimulation Buffer, 3 ul of test compound (12 μM final assay concentration) and 50 μl cells, Assay Buffer is stored on ice until utilized. The assay is initiated by addition of 50 μl of cAMP standards to appropriate wells followed by addition of 50 ul of PBSA to wells H-11 and H12. 50 μl of Stimulation Buffer is added to all wells. DMSO (or selected candidate compounds) is added to appropriate wells using a pin tool capable of dispensing 3 μl of compound solution, with a final assay concentration of 12 μM test compound and 100 μl total assay volume. The cells are then added to the wells and incubated for 60 min at room temperature. 100 μl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP for Gi Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of constitutive activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi linked target GPCR to establish a baseline level of cAMP. Upon creating a non-endogenous version of the Gi coupled receptor, this non-endogenous version of the target GPCR is then co-transfected with the signal enhancer, and it is this material that can be used for screening. We will utilize such approach to effectively generate a signal when a cAMP assay is used; this approach is preferably used in the direct identification of candidate compounds against Gi coupled receptors. It is noted that for a Gi coupled GPCR, when this approach is used, an inverse agonist of the target GPCR will increase the cAMP signal and an agonist will decrease the cAMP signal.

On day one, $2 \times 10^4$ 293 cells/well will be plated out. On day two, two reaction tubes will be prepared (the proportions to follow for each tube are per plate): tube A will be prepared by mixing 2 µg DNA of each receptor transfected into the mammalian cells, for a total of 4 µg DNA (e.g., pCMV vector; pCMV vector with mutated THSR (TSHR-A623I); TSHR-A623I and GPCR, etc.) in 1.2 ml serum free DMEM (Irvine Scientific, Irvine, Calif.); tube B will be prepared by mixing 120 µl lipofectamine (Gibco BRL) in 1.2 ml serum free DMEM. Tubes A and B will then be admixed by inversions (several times), followed by incubation at room temperature for 30-45 min. The admixture is referred to as the "transfection mixture". Plated 293 cells will be washed with 1×PBS, followed by addition of 10 ml serum free DMEM. 2.4 ml of the transfection mixture will then be added to the cells, followed by incubation for 4 hrs at 37° C./5% $CO_2$. The transfection mixture will then be removed by aspiration, followed by the addition of 25 ml of DMEM/10% Fetal Bovine Serum Cells will then be incubated at 37° C./5% $CO_2$. After 24 hr incubation, cells will then be harvested and utilized for analysis.

A Flash Plate™ Adenylyl Cyclase kit (New England Nuclear; Cat. No. SMP004A) is designed for cell-based assays, however, can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty four hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50 µl/well).

cAMP standards and Detection Buffer (comprising 1 µCi of tracer [$^{125}$I cAMP (50 µl] to 11 ml Detection Buffer) will be prepared and maintained in accordance with the manufacturer's instructions. Assay Buffer should be prepared fresh for screening and contained 50 µl of Stimulation Buffer, 31 µl of test compound (12 µM final assay concentration) and 50 µl cells, Assay Buffer can be stored on ice until utilized. The assay can be initiated by addition of 50 µl of cAMP standards to appropriate wells followed by addition of 50 µl of PBSA to wells H-11 and H12. Fifty µl of Stimulation Buffer will be added to all wells. Selected compounds (e.g. TSH) will be added to appropriate wells using a pin tool capable of dispensing 3 µl of compound solution, with a final assay concentration of 12 µM test compound and 100 µl total assay volume. The cells will then be added to the wells and incubated for 60 min at room temperature. 100 µl of Detection Mix containing tracer cAMP will then be added to the wells. Plates were then incubated additional 2 hours followed by counting in a Wallac MicroBeta scintillation counter. Values of cAMP/well will then be extrapolated from a standard cAMP curve which is contained within each assay plate.

4. Reporter-Based Assays a. CRE-LUC Reporter Assay (Gs-Associated Receptors)

293 and 293T cells are plated-out on 96 well plates at a density of $2 \times 10^4$ cells per well and were transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consists of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see, 7 *Human Gene Therapy* 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture is added to each well. 100 µl of DMEM with 10% FCS are added to each well after a 4 hr incubation in a cell culture incubator. The following day the transfected cells are changed with 200 µl/well of DMEM with 10% FCS. Eight (8) hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. API Reporter Assay (Gq-associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue #219073) can be utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP.

c. SRF-LUC Reporter Assay (Gq-associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with 1 µM Angiotensin, where indicated. Cells are then lysed and assayed for luciferase activity using a Luclite™ Kit (Packard, Cat. #6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular IP$_3$ Accumulation Assay (G$_q$-associated Receptors)

On day 1, cells comprising the receptors (endogenous and/or non-endogenous) can be plated onto 24 well plates, usually 1×10$^5$ cells/well (although his umber can be optimized. On day 2 cells can be transfected by firstly mixing 0.25 µg DNA in 50 µl serum free DMEM/well and 2 µl lipofectamine in 50 µl serum free DMEM/well. The solutions are gently mixed and incubated for 15-30 min at room temperature. Cells are washed with 0.5 ml PBS and 400 µl of serum free media is mixed with the transfection media and added to the cells. The cells are then incubated for 3-4 first at 37° C./5% CO$_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 µCi of $^3$H-myo-inositol/well and the cells are incubated for 16-18 hrs o/n at 37° C./5% CO$_2$. On Day 4 the cells are washed with 0.5 ml PBS and 0.45 ml of assay medium is added containing inositol-free/serum free media 10 µM pargyline 10 mM lithium chloride or 0.4 ml of assay medium and 50 µl of 10× ketanserin (ket) to final concentration of 10 µM. The cells are then incubated for 30 min at 37° C. The cells are then washed with 0.5 ml PBS and 200 µl of fresh/ice cold stop solution (1M KOH; 18 mM Na-borate; 3.8 mM EDTA) is added/well. The solution is kept on ice for 5-10 min or until cells were lysed and then neutralized by 200 µl of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100-200 mesh). Firstly, the resin is washed with water at 1:1.25 W/V and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd H$_2$O and stored at 4° C. in water.

Example 5

Fusion Protein Preparation a. GPCR:Gs Fusion Construct

The design of the GPCR-G protein fusion construct can be accomplished as follows: both the 5' and 3' ends of the rat G protein Gsα (long form; Itoh, H. et al., 83 *PNAS* 3776 (1986)) are engineered to include a HindIII (5'-AAGCTT-3') sequence thereon. Following confirmation of the correct sequence (including the flanking HindIII sequences), the entire sequence is shuttled into pcDNA3.1(−) Invitrogen, cat. no. V795-20) by subcloning using the HindIII restriction site of that vector. The correct orientation for the Gsα sequence is determined after subcloning into pcDNA3.1(−). The modified pcDNA3.1(−) containing the rat Gsα gene at HindIII sequence is then verified; this vector is now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq(6 Amino Acid Deletion)/Gi Fusion Construct

The design of a Gq(del)/Gi fusion construct can be accomplished as follows: the N-terminal six (6) amino acids (amino acids 2 through 7, having the sequence of TLESIM G$_α$q-subunit will be deleted and the C-terminal five (5) amino acids, having the sequence EYNLV will be replaced with the corresponding amino acids of the G$_α$i Protein, having the sequence DCGLF. This fusion construct will be obtained by PCR using the following primers:

(SEQ ID NO:13)
5'-gatcAAGCTTCCATGGCGTGCTGCCTGAGCGAGGAG-3'
and (SEQ ID NO:14)
5'-gatcGGATCCTTAGAACAGGCCGCAGTCCTTCAGGTTCAGCTGCAGG
ATGGTG-3' and Plasmid 63313 which contains the mouse G$_α$q-wild type version with a hemagglutinin tag as template. Nucleotides in lower caps are included as spacers.

TaqPlus Precision DNA polymerase (Stratagene) will be utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product will be cloned into a pCRII-TOPO vector (Invitrogen) and sequenced using the ABI Big Dye Terminator kit (P.E. Biosystems). Inserts from a TOPO clone containing the sequence of the fusion construct will be shuttled into the expression vector pcDNA3.1(+) at the HindIII/BamHI site by a 2 step cloning process. Also see, PCT Application Number PCT/US02/05625 published as WO02068600 on 6 Sep. 2002, the disclosure of which is hereby incorporated by reference in its entirety.

Example 6

[$^{35}$S]GTPγS Assay

A. Membrane Preparation

In some embodiments membranes comprising the Target GPCR of interest and for use in the identification of candidate compounds as, e.g., inverse agonists, agonists, or antagonists, are preferably prepared as follows:

a. Materials

"Membrane Scrape Buffer" is comprised of 20 mM HEPES and 10 nM EDTA, pH 7.4; "Membrane Wash Buffer" is comprised of 20 nM HEPES and 0.1 mM EDTA, pH 7.4; "Binding Buffer" is comprised of 20 mM HEPES, 100 mM NaCl, and 10 mM MgCl$_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 µl Binding Buffer. Thereafter, 10 µl of Bradford Protein Standard (1 mg/ml) will be added to each tube, and 10 µl of membrane Protein will then be added to just one tube (not the blank). Thereafter, 200 µl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

Identification Assay a. Materials

GDP Buffer consisted of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 µg/well). Thereafter, 100 µl GDP Buffer was added to each well of a Wallac Scintistrip™ (Wallac). A 5 ul pin-tool will then be used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein will be added to each well (a control well comprising membranes without the Target GPCR was also utilized), and pre-incubated for 5-10 minutes at room temperature. Thereafter, 50 µl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer instructions).

Example 7

Cyclic AMP Assay

Another assay approach for identifying candidate compounds as, e.g. inverse agonists, agonists, or antagonists, is accomplished by utilizing a cyclase-based assay. In addition to direct identification, this assay approach can be utilized as an independent approach to provide confirmation of the results from the [$^{35}$S]GTPγS approach as set forth in Example 6, supra.

A modified Flash Plate™ Adenylyl Cyclase kit (New England Nuclear; Cat. No. SMP004A) is preferably utilized for direct identification of candidate compounds as inverse agonists and agonists to endogenous or non-endogenous, constitutively activated GPCRs in accordance with the following protocol.

Transfected cells are harvested approximately three days after transfection. Membranes were prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 µCi of tracer {[$^{125}$I]cAMP (100 µl) to 11 ml Detection Buffer} are prepared and maintained in accordance with the manufacturer's instructions. Assay Buffer was prepared fresh for screening and contained 20 mM HEPES, pH 7.4, 10 mM MgCl$_2$, 20 mM phosphocreatine (Sigma), 0.1 units/ml creatine phosphokinase (Sigma), 50 µM GTP (Sigma), and 0.2 mM ATP (Sigma); Assay Buffer was then stored on ice until utilized.

Candidate compounds are added, preferably, to 96-well plate wells (3 µl/well; 12 µM final assay concentration), together with 40 µl Membrane Protein (30 µg/well) and 50 µl of Assay Buffer. This admixture was then incubated for 30 minutes at room temperature, with gentle shaking.

Following the incubation, 100 µl of Detection Buffer is added to each well, followed by incubation for 2-24 hours.

Plates are then counted in a Wallac MicroBeta™ plate reader using "Prot. #31" (as per manufacturer's instructions).

Figure 1:
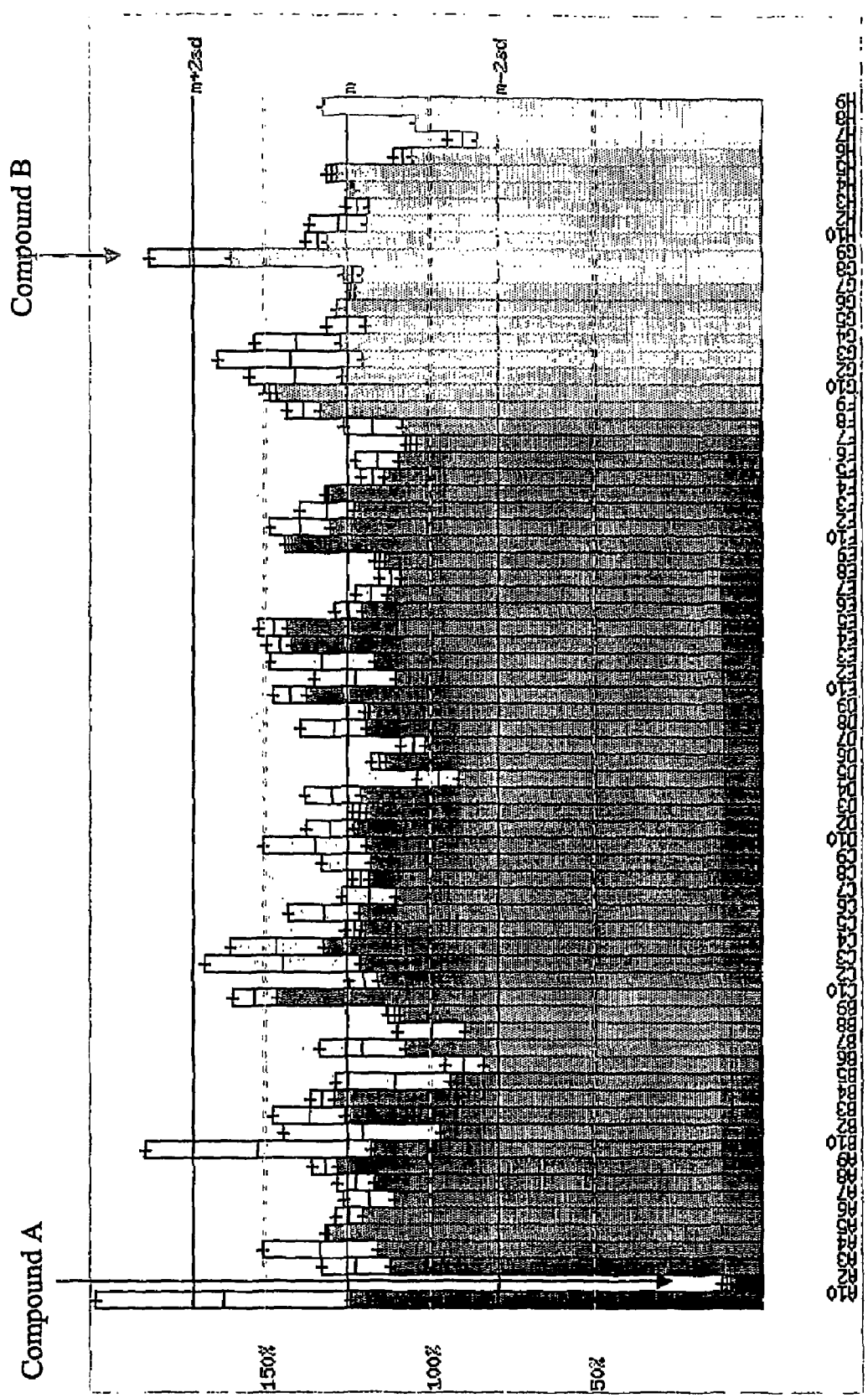
FIG. 1. By way of example and not limitation.

By way of example and not limitation, a representative screening assay plate (96 well format) result obtained is presented in FIG. 1. Each bar represents the result for a compound that differs in each well, the "Target GPCR" being a Gsα Fusion Protein construct of an endogenous, constitutively active Gs-coupled GPCR. The representative results presented in FIG. 1 also provide standard deviations based upon the mean results of each plate ("m") and the mean plus two arbitrary preference for selection of inverse agonists as "leads" from the primary screen involves selection of candidate compounds that that reduce the percent response by at least the mean plate response, minus two standard deviations. Conversely, an arbitrary preference for selection of agonists as "leads" from the primary screen involves selection of candidate compounds that increase the percent response by at least the mean plate response, plus the two standard deviations. Based upon these selection processes, the candidate compounds in the following wells were directly identified as putative inverse agonist (Compound A) and agonist (Compound B) to said endogenous GPCR in wells A2 and G9, respectively. See, FIG. 1. It is noted for clarity: these compounds have been directly identified without any knowledge of the endogenous ligand for this GPCR. By focusing on assay techniques that are based upon receptor function, and not compound binding affinity, we are able to ascertain compounds that are able to reduce the functional activity of this receptor (Compound A) as well as increase the functional activity of the receptor (Compound B).

Example 8

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at $5.5 \times 10^4$ cells/well with complete culture medium (DMEM with 10% FBS, 2 mM L-glutamine, 1 mM sodium pyruvate) for assay the next day. To prepare Fluo4-AM Molecular Probe, #F14202) incubation buffer stock, 1 mg Fluo4-AM is dissolved in 467 μl DMSO and 467 μl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 μl of 4 μM Fluo4-AM/2.5 mM Probenicid (Sigma, #P8761)/20 mM HEPES/complete medium at pH 7.4. Incubation at 37° C./5% CO2 is allowed to proceed for 60 min.

After the 1 hr incubation, the Fluo4-AM incubation buffer is removed and the cells are washed 2× with 100 μl wash buffer. In each well is left 100 μl wash buffer. The plate is returned to the incubator at 37° C./5% CO2 for 60 min.

FLIPR (Fluorometric Imaging Plate Reader; Molecular Device) is programmed to add 50 μl candidate compound on the 30th second and to record transient changes in intracellular calcium concentration ([Ca2+]) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target Receptor further comprise Gα15, Gα16, or the chimeric Gq/Gi alpha unit.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example 9

Tissue Distribution of Human FPRL2

Affymetrix GeneChip® Technology

Amino acid sequences were submitted to Affymetrix for the designing and manufacturing of microarray containing oligonucleotides to monitor the expression levels of G protein-coupled receptors (GPCRs) using their GeneChip® Technology. Also present on the microarray were probes for characterized human brain tissues from Harvard Brain Band or obtained from commercially available sources. RNA samples were amplified, labeled, hybridized to the microarray, and data analyzed according to manufacturer's instructions.

Figure 2:
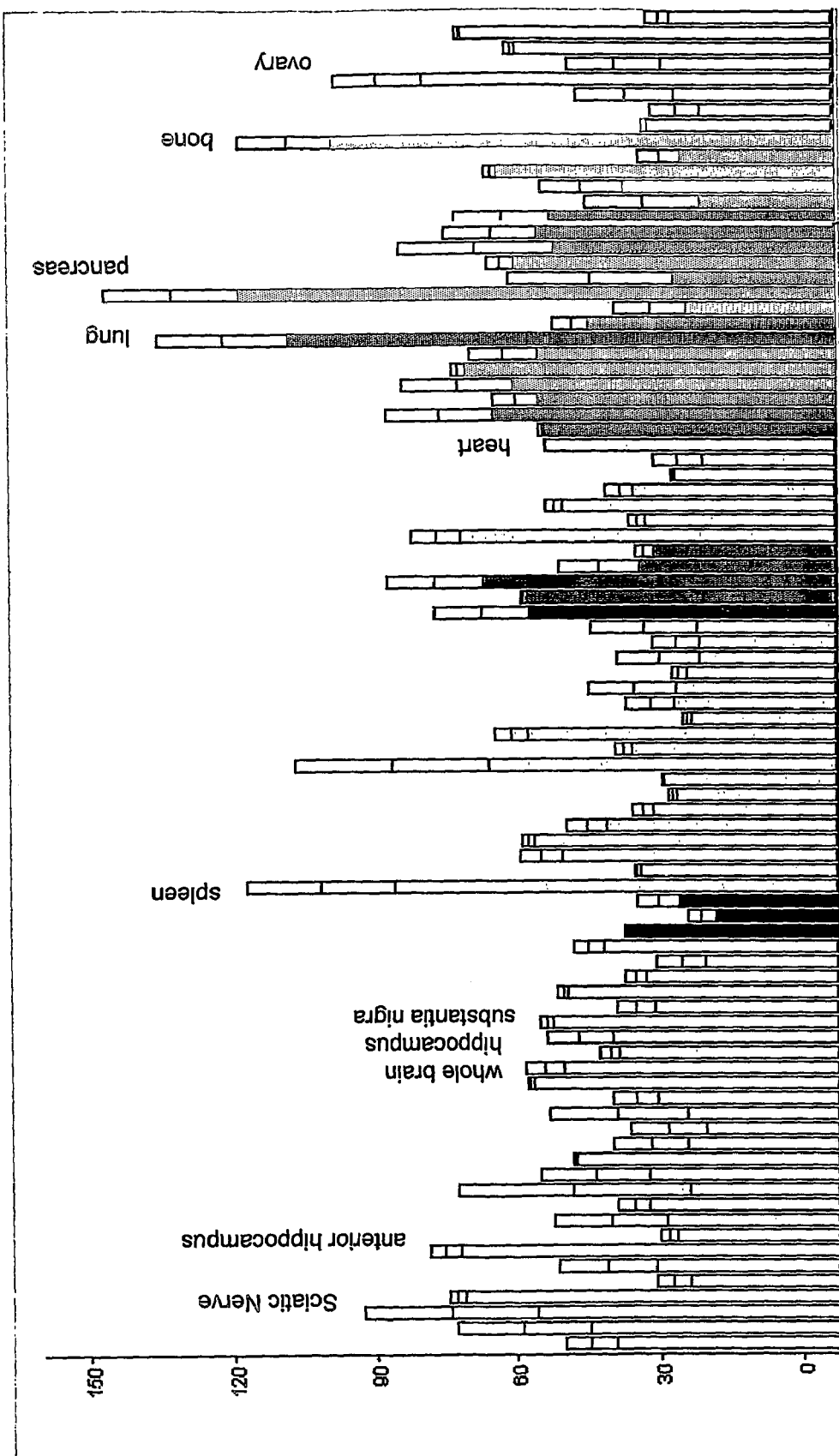
FIG. 2. Microarray analysis was performed on human tissue samples using a custom high-density oligonucleotide microarray, which contains probes that monitor the expression of FPRL2. The histogram plot provides the relative expression levels (Average Difference) and standard errors of duplicate measurements of FPRL2 for each of the tissues profiled. Relative expression level is indicated on the vertical axis. Tissue identity is displayed on the horizontal axis and is (from left to right): Pons, upper; Pituitary gland, female; Sciatic Nerve; Olfactory bulb; Pituitary gland, male; Corpus Callosum, Anterior Hippocampus, Cingulate gyrus, Ventral Tegmental Area (VTA); Neural progenitor; Pons, lower; Spinal cord; Hypothalamus, anterior; Astrocytes, resting; Cerebellum; Frontal Cortex, Superior BM9; Amygdala; Whole brain; Hippocampus; Globus pallidus; Medulla Oblongata; Substantia Nigra; Dorsal Root Ganglion; Thalamus; Astocytes, activated; Fetal Brain; Caudate Putamen; monocytes, adherent; Jurkat; U87; Spleen; Monocytes, CD14+; Thymus; dendritic precursors; Neutrophils; eosinophils; Natural Killer Cells; Bone Marrow; platelets; erythroid progenitors; Lymph Node; T-cells, CD4+ resting; AC133+; T-cells, CD4+ activated; T-cells, CD8+ resting; B-cells, CD19+; T-cells, CD8+ activated; CD34+ progenitor cells; cartilage; Adipocyte, primary; Adipose; Preadipocyte, cultured; Adipocyte, cultured; Pericardium; Aortic Endothelial Cells; Aorta; HUVEC; Aortic Smooth Muscle Cells, proliferative; Aortic smooth muscle cells, contractile; Heart; Rectum; Small Intestine; Colon; Stomach; Liver; Fetal Liver; Lung; Skeletal muscle; Esophagus; Pancreas; Bladder; Thyroid; Trachea; Kidney; Salivary Gland; Skin; Adrenal Gland; pancreatic islets; Mesenchymal stem cell; Bone; Uterus; Prostate; Testis; Ovary; Placenta; Cervix; Breast; Prostate epithelial.

Using the GeneChip, the expression profile of human FPRL2 was interrogated. See FIG. 2. FIG. 2 is a plot representing the expression level of human FPRL2 in various tissues. It is evident that the expression of human FPRL2 encompasses brain, peripheral nerve, and heart. Expression within brain encompasses anterior hippocampus, hippocampus, and substantia nigra. Expression within peripheral nerve encompasses sciatic nerve. Significant FPRL2 expression was also observed, e.g., for spleen, lung, pancreas, bone, and ovary.

Example 10

Identification of Humanin as a Selective Agonist of Human FPRL2

The activity of Humanin and [Gly14]-Humanin at human FPRL2, FPRL1 and FPR was determined by [35S]GTPγS binding assay using transiently transfected CHO cells.

The plasmids used were HA/V5 doubled tagged endogenous FPRL2 in pCMV, HA/V5 double-tagged endogenous FPRL1 in pCMV, HAN5 double-tagged endogenous FPR in pCMV, and pCMV alone (See, Example 1). Transient transfections were carried out on CHO-K1 cells. To a 15 cm dish of confluent cells, 12 μg of plasmid DNA and 60 μl Lipofectamine (Invitrogen, Carlsbad, Calif.) were added to each plate. Twenty-four hours post-infection, plasma membranes were isolated as described below. Assays were then run as described below.

1. Membrane Preparation a. Materials

"Membrane Scrape Buffer" consists of 20 mM HEPES and 10 mM EDTA, pH 7.4; "Membrane Wash Buffer" consists of 20 ml HEPES and 0.1 mM EDTA, pH 7.4; "Binding. Buffer" consists of 20 mM HEPES, 100 mM NaCl, and 10 mM $MgCl_2$, pH 7.4.

b. Procedure

All materials were kept on ice throughout the procedure. Firstly, the media was aspirated from a confluent monolayer of transfected cells, followed by rinse with 10 ml cold PBS, followed by aspiration. Thereafter, 10 ml of Membrane Scrape Buffer was added to scrape cells; this was followed by transfer of cellular extract into 50 ml centrifuge tubes (centrifuged at 20,000 rpm for 17 minutes at 4° C.). Thereafter, the supernatant was aspirated and the pellet was resuspended in 30 ml Membrane Wash Buffer followed by centrifuging at 20,000 rpm for 17 minutes at 4° C. The supernatant was then aspirated and the pellet resuspended in Binding Buffer. This was then homogenized using a Brinkman Polytron™ homogenizer (15-20 second bursts until the all material is in suspension). This is referred to herein as "Membrane Protein". A protein determination (Bradford Protein Assay) was carried out, and the protein concentration of the Membrane Protein was adjusted to 1.0 mg/ml with cold Binding Buffer for each of the experimental samples (FPRL2, FPRL1, FPR, pCMV).

2. Identification Assay a. Materials

GDP Buffer consisted of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [35S]GTPγS (0.6 nM) in Binding Buffer (2.5 µl [35S] GTPγS per 10 ml Binding Buffer).

b. Procedure

Humanin and [Gly14-Humanin] activity was interrogated using a 96-well plate format. First, 100 µl GDP Buffer was added to each well of a Wallac Scintistrip™ (Wallac). To each well was then added 5 ul of the appropriate concentration of Humanin or [Gly14-Humanin] or 5 µL solvent. Thereafter, 50 µl of Membrane Protein was added to each well (a control well comprising membranes without the GPCR Protein was also utilized), and pre-incubated for 5-10 minutes at room temperature. Thereafter, 50 µl of [$^{35}$S]GTPγS (0.6 nM) in Binding Buffer was added to each well, followed by incubation on a shaker for 60 minutes at room temperature (again, in this example, plates were covered with foil). The assay was then stopped by spinning of the plates at 4000 RPM for 15 minutes at 22° C. The plates were then aspirated with an 8 channel manifold and sealed with plate covers. The plates were then read on a Wallac 1450 using setting "Prot. #37" (as per manufacturer instructions).

3. Results

Humanin and [Gly14]-Humanin were unexpectedly found to be selective and robust agonists for FPRL2 (see, FIG. 3). Applicants provide Humanin as a first endogenous ligand for FPRL2 (FIG. 3). The EC50 of Humanin at FPRL2 is about 320 nm and that of [Gly14]-Humanin is about 72 nm (panel A). These values are more than an order of magnitude lower than the corresponding values at FPRL1 (panel B), which are about 9.24 µM for Humanin and about 1.5 µM for [Gly14]-Humanin. Neither Humanin nor [Gly14]-Humanin evidenced significant activity at FPR up to a dose of 10 µM (panel C). These results therefore further unexpectedly identify FPRL2 as a receptor selectively engaged by Humanin.

Example 11

Melanophore Technology a. Experimental System

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GPCR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods will be followed according to the disclosure of U.S. Pat. No. 5,462,856 and U.S. Pat. No. 6,051, 386. These patent disclosures are hereby incorporated by reference in their entirety.

The cells are plated in 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7×L-15 (Gibco). After one hour, the cells in serum-free media remain in a pigment-dispersed state while the melatonin-treated cells are in a pigment-aggregated state. At this point, the cells are treated with a dose response of a test/candidate compound. If the plated GPCRs bind to the test/candidate compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

b. FPRL2 Couples to Gi in Melanophores in Response to Humanin

Using melanophore technology, human FPRL2 was found to couple to Gi, or to a Gi-like G protein, in response to Humanin in a dose-dependent manner. A Gi-like G protein is a G protein that, like Gi, leads to a decrease in the level of intracellular cAMP. The EC50 of Humanin driven pigment aggregation in melanophore (Gi coupling) is about 239 nM (FIG. 4). Briefly, melanophore cells were harvested from confluent flasks (T-185 cm² flask) using Trypsin (0.7×), and transfected by electroporation. FPRL2-double tagged (HA/V5) DNA was used for transfection of melanophores. After electroporation, cells were preplated in flasks approximately 34 hours to rid of non-viable cells and debris. Upon completion, flasks were subsequently trypsinized and plated onto 96 well poly-D-lysine coated plates for assay. All assays were run 48 hours post transfection and assessed for FPRL-2 activity with Humanin. The cells were kept in conditioned fibroblasts media (CFM) throughout the 48 hour period. On the day of assay, the melanophore cells were removed from CFM and placed in (0.7×) L-15 media. The cells were exposed to room light for approximately one hour prior to assay to equilibrate. Initial T=0 readings were taken on a SpectraMax reader to assess background absorbance. Dose ranges of Humanin were added to the cells as denoted in FIG. 4. The cells were exposed to these dose concentrations for approximately 1 hour before taking T=60. The extent of melanophore cell aggregation denoting Gi coupling in melanophores transiently expressing FPRL2 is expressed as % change in absorbance from T=0 to T=60.

Example 12

Rescue of Mouse Primary Cortical Neurons from Aβ-Induced Toxicity

An agonist of the invention can be shown to rescue mouse primary cortical neurons from Aβ-induced toxicity using the in vitro model of Hashimoto et al. [J Neurosci (2001) 21:9235-45; the disclosure of which is hereby incorporated by reference in its entirety]. Said agonist is used at 0.1-100 µM. Some preferred said concentrations are selected from the group consisting of 0.1 µM, 0.3 µM, 1.0 µM, 3.0 µM, 10 µM, 30 µM and 100 µM. The placebo group is administered vehicle alone. Humanin and [Gly14]-Humanin are included in the protocol as controls.

The primary culture of mouse cortical neurons is performed in poly-D-lysine-coated 24-well plates (Sumitomo Bakelite, Akita, Japan), in the absence of serum and the presence of N2 supplement, as described elsewhere [Sudo et al., Mol Cell Neurosci (2000) 16:708-23; the disclosure of which is hereby incorporated by reference in its entirety]. The purity of neurons by this method is >98%. Prepared neurons (1.25×10⁵ cells per well and 250 µl of culture media per well) are preincubated with or without said agonist for 16 h and treated with 25 µM Aβ in the presence or absence of said agonist for 72 h. Aβ is purchased from Bachem (Budendorf, Switzerland) and Peptide Institute (Osaka, Japan). Cell viability is measured by trypan blue exclusion assay or by calcein staining. Calcein staining is performed as described elsewhere [Hashimoto et al., Proc Natl Acad Sci USA (2001) 98:6336-41; the disclosure of which is hereby incorporated by reference in its entirety]. In brief, 6 µM calcein AM {3',6'-di-(O-acetyl)-2',7'-bis[N,N-bis(carboxymethyl)aminomethyl]fluorescein, tetraacetoxymethyl ester; Dojindo} is added to neurons, and >30 min after calcein AM treatment, calcein-specific fluorescence (excitation, 485 nm; emission, 535 nm) is observed by fluorescence microscopy or measured by a spectrofluorometer (Wallac1420 ARVOsx Multi Label Counter).

All experiments described in this study are repeated at least three times with independent treatments. Statistical analysis is performed with Student's t test, in which p<0.05 is assessed as significant.

Example 13

Rescue of Human Cerebrovascular Smooth Muscle Cells from Aβ-Induced Toxicity

An agonist of the invention can be shown to rescue human cerebrovascular smooth muscle cells from Aβ-induced toxicity using the in vitro model of Jung and Van Nostrand [J Neurochem (2003) 84:266-72; the disclosure of which is hereby incorporated by reference in its entirety]. Said agonist is used at 0.1-100 µM. Some preferred said concentrations are selected from the group consisting of 0.1 µM, 0.3 µM, 1.0 µM, 3.0 µM, 10 µM, 30 µM, and 100 µM. The placebo group is administered vehicle alone. Humanin and [Gly14]-Humanin are included in the protocol as controls.

Primary cultures of human cerebrovascular smooth muscle (HCSM) cells are established and characterized as described elsewhere [Van Nostrand et al., Amyloid (1994) 1:1-7]. The HCSM cells are derived from leptomeningeal vessels of control adult subjects and show strong expression of the specific markers vascular smooth muscle cell α-actin, vascular smooth muscle cell myosin, and SM22α. HCSM cells are cultured in 24-well plates in Dulbecco's modified Eagle's medium (DMEM) supplemented with 10% fetal bovine serum (Gemini Bio-Products, Woodland, Calif.), 1 mM nonessential amino acids, 2 mM glutamine, 1000 U/mL penicillin, 1000 µg/mL streptomycin (Life Technologies, Rockville, Md.). For experiments, cells are grown to near-confluence (90%) and replaced with serum-free DMEM containing 0.1% bovine serum albumin (BSA) for 24 h prior to treatment. Cells are treated, in triplicate, with freshly solubilized Dutch variant beta-amyloid (Aβ40D, 25 µM, American Peptide Co., Sunnyvale, Calif.) for 6 days in the presence or absence of said agonist. Cells are examined routinely using an inverted system Olympus IX70 phase contrast microscope (Olympus America Inc., Lake Success, N.Y.).

Cell viability is assessed using a fluorescent live/dead assay following the manufacturer's protocol (Molecular Probes, Eugene, Oreg.). Briefly, after treatment with Aβ40D in the presence or absence of said agonist, cells are exposed to both calcein AM and ethidium homodimer-1 and viewed using an inverted system Olympus IX70 fluorescence microscope. Intracellular esterases in living cells convert the substrate calcein AM into a brightly green fluorescent product calcein. Dead cells are observed when the DNA chelator ethidium homodimer-1 enters cells with damaged cell membranes, resulting in a bright red fluorescence. Live an dead cells are counted from several fields (n=4-6) from at least three separate wells for each experiment.

Statistical analysis are performed using the GraphPad INSTAT program (San Diego, Calif.).

Example 14

Inhibition of Cell Death of Serum-Deprived PC12h Cells

An agonist of the invention can be shown to be inhibit cell death of serum-deprived PC12h cells using the in vitro model of Kariya et al. [NeuroReport (2002) 13:903-7; the disclosure of which is hereby incorporated by reference in its entirety]. Said agonist is used at 0.1-100 µM. Some preferred said concentrations are selected from the group consisting of 0.1 µM, 0.3 µM, 1.0 µM, 3.0 µM, 10 µM, 30 µM, and 100 µM. The placebo group is administered vehicle alone. Humanin and [Gly14]-Humanin are included in the protocol as controls.

Rat PC12h cells are maintained in serum-supplemented medium (DMEM, containing 0.45% glucose, 5% fetal bovine serum, and 10% horse serum) at 37° C. with 5% $CO_2$. These cells are then plated on collagen-coated 96-well plates at a density of $2\times10^4$ cells/well, and incubated for 24 h. To show the inhibition of cell death of serum-deprived PC12h cells by said agonist, the serum-supplemented medium in each well is exchanged for serum-free medium with or without said agonist. After preliminary incubation (0 h, 12 h, 24 h, 36 h, or 48 h), the media of all the wells is exchanged for the serum-supplemented media containing 20% MTS solution, and the plates are incubated for 90 min at 37° C. The color intensity, which is proportional to the number of metabolically active cells, is assessed at 492 nm on a plate reader. The effect of said agonist on healthy PC12h cells is also examined.

All experiments described in this study are repeated independently at last three times. Statistical analysis is performed with Student's t-test.

Example 15

Improvement of the Learning and Memory Impairment Induced by Scopolamine

An agonist of the invention can be shown to be improve the learning and memory impairment induced by scopolamine in an the in vivo mouse model of Mamiya and Ukai [Br J Pharmacol (2001) 134:1597-9; the disclosure of which is hereby incorporated by reference in its entirety]. Scopolamine (a muscarinic acetylcholine receptor antagonist)-induced impairment model is widely used to evaluate the effects of anti-amnesic drugs on learning ability in experimental models. Said agonist is administered by intraperitoneal injection. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. The placebo group is administered vehicle alone. Humanin and [Gly14]-Humanin are included in the protocol as controls.

Male ddY mice (Nihon SLC Co., Shizuoka, Japan), 6-8 weeks of age, are used. The animals are housed in a controlled environment (23±1° C., 50±5% humidity) and are allowed food and water ad libitum. The room lights are on between 0800 and 2000 h. Scopolamine HBr (1 mg/kg, s.c., Sigma) and said agonist are dissolved in saline. The i.c.v. injection is carried out under light ether anaesthesia as reported elsewhere [Hiramatsu et al., Br J Pharmacol (1998) 123:920-6; Mamiya et al., Neuropharmacology (2000) 39:2391-8; Ukai et al., Eur J Pharmacol (2000) 395:211-5; the disclosure of each of which is hereby incorporated by reference in its entirety]. To verify the locus of the injection, a group of mice is injected i.c.v. with Indian ink because of free hand injection. That the ink is diffused throughout the cerebral ventricle in more than 90% of the animals examined is then checked. Scopolamine HBr (0.1 ml per 10 g body weight) and said agonist (5 μl per mouse) are administered 30 and 15 min before the Y-maze test, respectively. The protocol is performed according to previous reports [Hiramatsu & Inoue, Br J Pharmacol (1999) 127:655-60; Ukai et al., Eur J Pharmacol (2000) 395:211-5; the disclosure of each of which is hereby incorporated by reference in its entirety]. Briefly, short-term memory performance is examined by monitoring spontaneous alternation behavior in the Y-maze test. The maze is made of black painted wood; each arm is 40 cm long, 12 cm high, 3 cm wide at the bottom and 10 cm wide at the top. The arms converge at an equilateral triangular central area that is 4 cm at its longest axis. The apparatus is placed on the floor of the experimental room and is illuminated with a 100-W bulb from 200 cm above. Each mouse is placed at the end of one arm and allowed to move freely through the maze during an 8-min session and the series of arm entries is recorded visually. Alternation is defined as successive entry into the three arms, on overlapping triplet sets. Alternation behavior (%) is calculated as the ratio of actual alternations to possible alternations (defined as the total number of arm entries minus two), multiplied by 100 [Mamiya et al., Neuropharmacology (2000) 39:2391-8; Ukai et al., Eur J Pharmacol (2000) 395: 211-5; the disclosure of each of which is hereby incorporated by reference in its entirety]. After the experiments, the number of arm entries and faces are counted. The results are expressed as the mean±s.e.mean. Statistical significance is determined by one-way ANOVE followed by the Dunnett multiple comparisons test. $P<0.05$ is taken as the significant level of difference.

Example 16

Cardioprotection

An agonist of the invention can be shown to be cardioprotective using the in vivo rat model of Fryer et al. [Circ Res (1999) 84:846-51; the disclosure of which is hereby incorporated by reference in its entirety]. Said agonist is administered by intraperitoneal injection. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. The placebo group is administered vehicle alone. Humanin and [Gly14]-Humanin are include in the protocol as controls.

Male Wistar rats, 350 to 450 g, are used for all phases of this study. Rats are administered said agonist or saline 1, 12, 24, 48, or 72 hours before the surgical protocol through intraperitoneal injection. Subsequently, rats are anesthetized via intraperitoneal administration of thiobutabarbital sodium (Inactin, Research Biochemical International; 100 mg/kg). A tracheotomy is performed, and the trachea is intubated with a cannula connected to a rodent ventilator (model CIV-101, Columbus Instruments, or model 683, Harvard Apparatus). Rats are ventilated with room air supplemented with $O_2$ at 60-65 breaths per minute. Atelectasis is prevented by maintaining a positive end-expiratory pressure of 5 to 10 mm H2O. Arterial pH, $P_{CO2}$, and $P_{O2}$ are monitored at control, 15 minutes of occlusion, and 60 and 120 minutes of reperfusion by a blood gas system (AVL 995 pH/blood gas analyzer, AVL Medical Instruments) and maintained within a normal physiological range (pH 7.35 to 7.45; $P_{CO2}$ 25 to 40 mm Hg; and $P_{O2}$ 80 to 110 mm Hg) by adjusting the respiratory rate and/or tidal volume. Body temperature is maintained at 38° C. by the use of a heating pad, and bicarbonate is administered intravenously as needed to maintain arterial blood pH within normal physiological levels.

The right carotid artery is cannulated to measure blood pressure and heart rate via a Gould PE50 or Gould PE23 pressure transducer connected to a Grass (model 7) polygraph. The right jugular vein is cannulated for saline, bicarbonate, and drug infusion. A left thoracotomy is performed at the fifth intercostals space followed by a pericardiotomy and adjustment of the left atrial appendage to reveal the location of the left coronary artery. A ligature (6-0 prolene) is passed below the coronary artery from the area immediately below the left atrial appendage to the right portion of the left ventricle. The ends of the suture are threaded through a propylene tube to form a snare. The coronary artery is occluded by pulling the ends of the suture taut and clamping the snare onto the epicardial surface with a hemostat. Coronary artery occlusion is verified by epicardial cyanosis and a subsequent decrease in blood pressure. Reperfusion of the heart is initiated via unclamping the hemostat and loosening the snare and is confirmed by visualizing an epicardial hyperemic response. Heart rate and blood pressure are allowed to stabilize before the experimental protocols are initiated.

Rats are randomly divided into the designated experimental groups. Control rats are administered saline 24 hours before 30 minutes of regional ischemia and 2 hours of reperfusion (I/R). To show acute cardioprotection induced by said agonist, said agonist is administered 1 hour before a prolonged ischemic insult. To show the delayed cardioprotection against an acute ischemic insult, said agonist is administered at the designated doses either 12 or 24 hours before I/R. Said agonist is also administered at the designated doses either 48 or 72 hours before I/R.

On completion of the above protocols, the coronary artery is occluded, and the area at risk (AAR) is determined by negative staining with patent blue dye administered via the jugular vein. The rat is euthanized with a 15% KCl solution. The heart is excised and the left ventricle is dissected from the remaining tissue and subsequently cut into 6 thin, cross-sectional pieces. This allows for the delineation of the normal area, stained blue, versus the AAR, which subsequently remained pink. The AAR is excised from the nonischemic area, and the tissues are placed in separate vials and incubated for 15 minutes with 1.0% 2,3,5-triphenyltetrazolium chloride (TTC) stain in 100 mmol/L phosphate buffer (pH 7.4) at 37° C. TTC is an indicator of viable and nonviable tissue. TTC is reduced by dehydrogenase enzymes present in viable myocardium and results in a formazan precipitate, which induces a deep red color, whereas the infected area remains gray {Klein et al., Virchows Arch [Pathol Anat] (1981) 393:287-97}. Tissues are stored in vials of 10% formaldehyde overnight, and the infracted myocardium is dissected from the AAR under the illumination of a dissecting microscope (Cambridge Instruments). Infarct size (IS), AAR, and left ventricular weight (LV) are determined by gravimetric analysis. AAR is expressed as a percentage of the LV (AAR/LV), and IS is expressed as a percentage of the AAR (IS/AAR).

Rats are excluded from data analysis if they exhibit severe hypotension (<30 mm Hg systolic blood pressure) or if adequate blood gas values within a normal physiological range are unable to be maintained because of metabolic acidosis or alkalosis.

All values are expressed as mean±SEM. One-way ANOVA with Bonferroni's test is used to determine whether any significant differences exist among groups for hemodynamics, IS, and AAR. Significant differences are determined at $P<0.05$.

It is envisioned that an agonist of the invention can alternatively be shown to be cardioprotective using, for example, an in vivo non-human primate model.

Example 17

Inhibition of In-Stent Neointimal Growth

Both rapamycin- and paclitaxel-eluting stents are associated with reduced restenosis rates in animals studies and initial human trials. Rapamycin has been shown to inhibit vascular smooth muscle cell proliferation in vitro. An application of effective systemic therapy for inhibition of in-stent neointimal growth is the ability to provide follow-up booster dosings once local stent-based drugs are exhausted (i.e., completely released from the stent).

An inverse agonist or an antagonist of the invention can be shown to inhibit in-stent intimal growth using the in vivo rabbit model of Farb et al. [Circulation (2002) 106:2379-84; the disclosure of which is hereby incorporated by reference in its entirety]. Said inverse agonist or antagonist can be shown to reduce neointimal thickness, neointimal area, and percent stent stenosis, and to increase lumen area. Said inverse agonist or antagonist is administered daily by oral gavage in a volume of 2 ml/kg. Preferred dose is 0.1-100 mg/kg. Other preferred dose is selected from the group consisting of: 0.1 mg/kg, 0.3 mg/kg; 1.0 mg/kg; 3.0 mg/kg; 10 mg/kg; 30 mg/kg and 100 mg/kg. Dosing is begun 1-3 days before stenting. The placebo group is administered vehicle alone.

Under fluoroscopic guidance, bilateral iliac artery balloon injury is performed in anesthetized rabbits followed by placement of a 2×12-mm MULTI-LINK (Guidant Corp) stent (6 ATM, 30-second balloon inflation, stent-to-artery ratio of 1.2:1) All animals receive aspirin 40 mg/d orally until euthanasia.

Twenty-eight days after stenting, animals are anesthetized, and a pre-euthanasia angiogram of the iliac arteries is completed followed by euthanasia and perfusion fixation. The stented arteries are embedded in methylmethacrylate with sections taken from the proximal, middle, and distal portions of each stent. A 3-mm arterial segment just proximal and distal to the stents was processed and stained to evaluate edge effects. All sections are stained with H&E and Movat pentachrome stain. To assess cellular proliferation, animals received bromodeoxyuridine (BrdU) before euthanasia, as described elsewhere [Farb et al., Int J Radiat Oncol Biol Phys (2000) 48:889-98]. Mid-stent sections are also stained with antibodies to RAM11 (Dako Corp) to identify macrophages and fibrin (American Diagnostica, Inc.). To evaluate stent endothelialization, additional rabbits undergo stenting, as described above, followed by longitudinally cut stents.

All arterial segments are examined blindly. Computerized planimetry is performed on all stented sections, as previously described [Farb et al., Int J Radiat Oncol Biol Phys (2000) 48:889-98]. Total cell number, RAM11-positive macrophages, and fibrin are quantitated from the entire neointima of midstent sections. The neointimal cell proliferation index (percent proliferating cells) is defined as the ratio of BrdU-positive neointimal cells to total neointimal cell number. The percent of the stent intimal surface that is endothelialized is measured from scanning electron microscopy images of the entire stent surface. Data are expressed as mean±SD. Incomplete neointimal healing is defined as the presence of fibrin or inflammation or the absence of endothelial cells. Statistical analysis of the histologic data is accomplished using ANOVA. $P<0.05$ is considered statistically significant.

Example 18

Inhibition of Neuroblastoma Tumor Growth

Neuroblastoma accounts for 14% of all cancers in children younger than five years of age. The majority of neuroblastomas are aggressive metastatic tumors with poor clinical outcome despite intensive multimodal therapy.

An inverse agonist or an antagonist of the invention can be shown to inhibit neuroblastoma tumor growth in vivo, using the xenogeneic rat model of Ponthan et al. [Int J Cancer (2003) 104:418-24; the disclosure of which is hereby incorporated by reference in its entirety]. Said inverse agonist or antagonist is administered by continuous oral treatment with a gastric feeding tube. Preferred dose is 0.1-100 mg/kg per day. Other preferred dose is selected from the group consisting of: 0.1 mg/kg per day, 0.3 mg/kg per day; 1.0 mg/kg per day; 3.0 mg/kg per day; 10 mg/kg per day; 30 mg/kg per day and 100 mg/kg per day. Dosing is begun 1-3 days before stenting. The placebo group is administered vehicle alone.

Nude rats are anaesthetized and injected with $20 \times 10^6$ human SH-SY5Y neuroblastoma cells in each hind leg. When tumor take is evident by palpation and/or visible, the tumor length (along the tumor long axis) and width (perpendicular to the long axis) are measured with a caliper every second day. Tumor volume is calculated by: length×width$^2$×0.44 [Wassberg et al., Pediatr Res (1997) 41:327-33]. The true tumor weight is recorded at autopsy. Tumor volume index is calculated using the measured volume divided with the volume measured at tumor take when treatment starts.

When a tumor in an animal reaches a volume of 0.3 ml (designated day 0), the rat is randomized into 1 of 2 groups, and treatment is started. Only those tumors that reach a volume of 0.3 ml when treatment is started are followed and evaluated for response. Treatment continues for 12 days. Tumor volume is determined at days 2, 4, 6, 8, 10 and 12, the tumor volume index is calculated, and the percent tumor volume index relative to that of vehicle alone is plotted.

Statistical analysis is performed by using the Mann-Whitney U test for 2 independent samples. All p-values refer to a 2-sided probability unless stated otherwise.

Recently, an alternative, noninvasive method for estimating tumor viability in a xenograft model of human neuroblastoma using proton magnetic resonance spectroscopy has been described [Lindskog et al., Br J Cancer (2003) 88:478-85].

Example 19

Oral Bioavailability

Physicochemico analytical approaches for directly assessing oral bioavailability are well known to those of ordinary skill in the art and may be used [see, e.g., without limitation: Wong P C et al., Cardiovasc Drug Rev (2002) 20:137-52; and Buchan P et al., Headache (2002) Suppl 2:S54-62; the disclosure of each of which is hereby incorporated by reference in its entirety]. By way of further illustration and not limitation, said alternative analytical approaches may comprise liquid chromatography-tandem mass spectrometry [Chavez-Eng C M et al., J ChromatogrB Analyt Technol Biomed Life Sci (2002) 767:117-29; Jetter A et al., Clin Phanmcol Ther (2002) 71:21-9; Zimmerman J J et al., J Clin Pharmacol (1999) 39:1155-61; and Barrish A et al., Rapid Commun Mass Spectrom (1996) 10:1033-7; the disclosure of each of which is hereby incorporated by reference in its entirety]. Recently, positron emission tomography (PET) has been successfully used to obtain direct measurements of drug distribution, including oral bioavailability, in the mammalian body following oral administration of the drug [Gulyas et al., Eur J Nucl Med Mol Imaging (2002) 29:1031-8; the disclosure of which is hereby incorporated by reference in its entirety].

Alternatively, based upon the in vivo data developed, as for example by way of illustration and not limitation, through the rat model of Example 16 directed to cardioprotection, supra, oral bioavailability of a modulator of the invention is determined. The modulator is administered by oral gavage at doses ranging from 0.1 mg kg$^{-1}$ to 100 mg kg$^{-1}$. Oral administration of the modulator is shown to confer cardioprotection. The effect of the modulator is shown to be dose-dependent and comparable to the effect after intraperitoneal administration. The dose of modulator required to achieve half-maximal reduction of IS/AAR through oral administration is compared to the dose of modulator required to achieve half-maximal reduction of IS/AAR through intraperitoneal administration. By way of illustration, if said oral dose is twice said intraperitoneal dose, then the oral bioavailability of the modulator is taken to be 50%. More generally, if said oral dose is $\theta$ mg kg$^{-1}$ and said intraperitoneal dose is $\rho$ mg kg$^{-1}$, then the oral bioavailability of the modulator as a percentage is taken to be $[(\rho/\theta) \times 100]$.

It is readily envisioned that the reference route of administration may be other than intraperitoneal. In some embodiments, said reference route of administration is intravenous.

It would be readily apparent to anyone of ordinary skill in the art that the aforesaid determination could be modified to utilize a different in vivo animal model other than cardioprotection. It would also be readily apparent to anyone of ordinary skill in the art that the bioactivity readout could be a parameter other than IS/AAR.

Example 20

Blood Brain Barrier Model

The ability of a compound of the invention to cross the blood-brain barrier can be determined using brain-derived cells. One method that is envisioned, by way of illustration and not limitation, is to use the blood/brain barrier model of Dehouck et al. [J Neurochem (1990) 54:1798-801; hereby incorporated by reference in its entirety] that uses a co-culture of brain capillary endothelial cells and astrocytes.

Bovine capillary endothelial (BBCE) cells are isolated and characterized as described by Meresse et al. [J Neurochem (1989) 53:1363-1371; hereby incorporated by reference in its entirety]. In brief, after isolation by mechanical homogenization from one hemisphere of bovine brain, microvessels are seeded onto dishes coated with an extracellular matrix secreted by bovine corneal endothelial cells. Five days after seeding, the first endothelial cells migrate out from the capillaries and begin to form microcolonies. When the colonies are sufficiently large, the five largest islands are trypsinized and seeded onto 35-mm-diameter gelatin-coated dishes (one clone per dish) in the presence of Dulbecco's modified Eagle's medium (DMEM supplemented with 15% calf serum (Seromed), 3 mM glutamine, 50 µg/ml of gentamicin, 2.5 µg/ml of amphotericin B (Fungizone), and bovine fibroblast growth factor (1 ng/ml added every other day). Endothelial cells from one 35-mm-diameter dish are harvested at confluence and seeded onto 60-mm-diameter gelatin-coated dishes. After 6-8 days, confluent cells are subcultured at the split ratio of 1:20. Cells at the third passage (~100 dishes) are stored in liquid nitrogen.

Primary cultures of astrocytes are made from newborn rat cerebral cortex. After the meninges have been cleaned off, the brain tissue is forced gently through a nylon sieve as described by Booher and Sensenbrenner [Neurobiology (1972) 2:97-105; hereby incorporated by reference in its entirety]. DMEM supplemented with 10% fetal calf serum (Seromed), 2 mM glutamine, and 50 µg/ml of gentamicin is used for the dissociation of cerebral tissue and development of astrocytes.

Culture plate inserts (Millicell-CM; pore size, 0.4 µM; diameter, 30 mm; Millipore) are coated on both sides with rat tail collagen prepared by a modification of the method of Bornstein [Lab Invest (1958) 7:134-139; hereby incorporated by reference in its entirety].

Astrocytes are plated at a concentration of $2.5 \times 10^5$ cells/ml on the bottom side using the filter upside down. After 8 days, filters are properly positioned, and the medium is changed twice a week. Three weeks after seeding, cultures of astrocytes become stabilized. Then, BBCE cells, frozen at passage 3, are recultured on a 60-mm-diameter gelatin-coated dish. Confluent cells are trypsinized and plated on the upper side of the fixtures at a concentration of $4 \times 10^5$ cells. The medium used for the coculture is DMEM supplemented with 15% calf serum 2 mM glutamine, 50 µg/ml of gentamicin, and 1 ng/ml of bovine fibroblast growth factor added every other day. Under these conditions, BBCE cells form a confluent monolayer in 8 days.

Culture plates are set into six-well plates with 2 ml of buffer added to the upper chamber and 2 ml added to the plate containing the inserts. The six-well plates are placed in a shaking water bath at 37° C. The compound of the invention is added to the upper chamber, and 100 µl is removed from the lower chamber at various time points. In certain embodiments, the test compound is radiolabeled. In certain embodiments, the radiolabel is $^3$H or $^{14}$C. In some embodiments, the final time point is about 20 min, about 30 min, about 40 min, about 50 min, about 60 min, about 70 min, about 80 min or about 90 min. The percentage of total test compound present in the lower chamber at the various time points is determined. Leucine is used as a permeability positive control. Inulin is used as a permeability negative control.

In certain embodiments, a determination of at least about 10%, at least about 20%, at least about 30%, at least about 40%, at least about 50%, at least about 60%, at least about 70%, at least about 80% or at least about 90% of the compound of the invention in the lower chamber at the final time point is indicative of the compound of the invention being able to cross the blood-brain barrier.

Example 21

Identification of Compound 1 as a Selective Agonist of Human FPRL2

The activity of Compound 1 at human FPRL2, FPRL1 and FPR was determined by [$^{35}$S]GTPγS binding assay using transiently transfected CHO cells and by melanophore assay. Details of the [$^{35}$S]GTPγS binding assay can be found in Example 10. Details of the melanophore assay can be found in Example 11. Compound 1 was found to be a robust and selective agonist of FPRL2 (FIG. 5).

That Compound 1 is a robust and selective agonist of FPRL2 is also apparent from inspection of FIG. 6. In FIG. 6, agonist activity was determined through adenylate cyclase activity. Briefly, HEK293 cells stably transfected with FPRL1 or FPRL2 were treated with Humanin, [Gly14]-Humanin or Compound 1 at the indicated concentration in the presence of 5 µM forskolin at $10^5$ cells/well. Samples were then assessed for the level of intracellular cAMP as described in Example 4, supra. Whereas Humanin and [Gly14]-Humanin were found to be agonists of both FPRL1 and FPRL2 (FIG. 6A), Compound 1 was found to be selectively an agonist of FPRL2 (FIG. 6B).

Example 22

Both Human and Compound 1 Signal Via a Pertussis Toxin-Sensitive Mechanism on Human FPRL2

The pertussis toxin sensitivity of Humanin signaling through human FPRL2 was determined by adenylate cyclase assay using HEK293 cells stably transfected with human FPRL2. The pertussis toxin sensitivity of Compound 1 signalling through human FPRL2 was determined similarly.

Briefly, HEK293 cells stably transfected with FPRL2 were treated with Humanin or Compound 1 at the indicated concentration in the presence of 5 µM forskolin at $10^5$ cells/well. Samples were then assessed for cAMP levels as described in Example 4, supra. To determine the pertussis toxin sensitivity of signaling, cells were pre-treated for 18 to 20 hrs with 50 ng/ml pertussis toxin, after which cells were washed with pre-warmed (37° C.) PBS prior to assay with Humanin or Compound 1.

From inspection of FIG. 7, it is apparent that the inhibition of cAMP mediated either by Humanin (FIG. 7A) or by Compound 1 (FIG. 7B) through FPRL2 was pertussis sensitive, indicating that FPRL2 couples to a pertussis-sensitive G protein in response to Humanin or Compound 1. Gi and Go are known to be pertussis-sensitive G proteins.

Example 23

FPRL2 Signals Through Gα16 in Response to Humanin Or Compound 1

The capacity of FPRL2 to couple to Gα16 in response to Humanin, [Gly14]-Humanin, or Compound 1 was determined by IP$_3$ assay. Briefly, HEK293 cells were transiently transfected with 6 µg FPRL2 plasmid DNA and 6 µg Gα16 plasmid DNA per $10^7$ cells per 15 cm culture dish using lipofectamine (Invitrogen). At 24 hr post transfection, the HEK293 cells were labeled overnight with 5 µCi/ml [$^3$H]-myo-inositol. The cells were then washed. The assay was initiated on contacting the HEK293 cells with either Humanin, [Gly14]-Humanin, or Compound 1. The level of intracellular IP$_3$ was determined as described in Example 4, supra.

Inspection of FIG. 8 indicates dose-dependent elevation of the level of intracellular IP$_3$ by Humanin, [Gly14]-Humanin and Compound 1. As a negative control, it was shown that there was no IP$_3$ response to either Humanin or Compound 1 by HEK293 cells transiently transfected with FPR (not shown).

Example 24

Expression of FPRL2 but not FPRL1 by SH-SY5Y Cells

The expression of FPRL2 and FPRL1 by the human neuroblastoma cell line SH-SY5Y, before or after differentiation by brain-derived nerve growth factor (BDNF), was determined. SH-SY5Y cells were differentiated into neuronal-like cells by treatment with retinoic acid (10 µM) for five days followed by treatment with BDNF (10 ng/ml) for two days. RT-PCR analysis was carried out on mRNA isolated from undifferentiated ("SH-SY5Y") or differentiated ("SH-/BDNF") SH-SY5Y cells, using primers specific to the coding region of either FPRL2 or FPRL1.

Conversion of mRNA to cDNA was carried out using MMLV reverse transcriptase. Amplification was carried out using Taq DNA polymerase. Visualization of the amplification product was carried out by agarose gel electrophesis and ethidium bromide staining. From FIG. 9A, it is apparent that whereas FPRL2 mRNA is detectable both in undifferentiated and differentiated SH-SY5Y cells ("+RT" samples), FPRL1 mRNA is not ("+RT" samples). In FIG. 9A, "FPRL2" and "FPRL1" are positive controls in which the template is FPRL2 or FPRL1 cDNA; respectively. "NT" is a negative control in which there is no DNA template. "−RT" is a negative control in which reverse transcriptase was omitted from the reaction converting mRNA to cDNA. "1 Kb" corresponds to molecular weight markers.

Specificity of the primers used for FPRL2 amplification is demonstrated in FIG. 9B, where the expected amplification product was observed when FPRL2 cDNA was used as template, but not when either FPRL1 or FPR cDNA was used as template. Results are presented in FIG. 9B as a reverse photographic image of an ethidium bromide-stained agarose gel.

Example 25

Inhibition of Cell Death of Serum-Deprived SH-SY5Y Cells

The capacity of Humanin or Compound 1 to inhibit the cell death of serum-deprived differentiated SH-SY5Y cells was determined. Briefly, SH-SY5Y cells were differentiated into neuronal-like cells by treatment with retinoic acid (10 μM) for five days followed by treatment with BDNF (10 ng/ml) for two days. The cells were then cultured in serum-free medium for 6 days with or without Humanin or Compound 1. Cell viability was determined by lactate dehydrogenase (LDH) assay (Roche, Indianapolis, Ind.; catalog no. 1644793) or by trypan blue staining. LDH is a stable cytoplasmic enzyme present in all cells which is rapidly released upon damage to the plasma membrane. The level of LDH is inversely proportional to the number of viable cells. The LDH assay was carried out as per manufacturer's instructions.

Results are presented in FIG. 10A for the LDH assay and in FIG. 10B for trypan blue staining. Inspection of FIG. 10 indicates that both Humanin and Compound 1 ("Cmpd1") inhibited cell death of serum-deprived SH-SY5Y cells.

Example 26

Inhibition of 22C11 (anti-APP Antibody)-Induced Cell Death of Primary Mouse Cortical Neurons The capacity of Humanin or Compound 1 to inhibit the cell death of primary mouse cortical neurons induced by antibody 22C11 was determined. 22C11 is a monoclonal antibody (mAb) which binds to the extracellular domain of the human, rat or mouse β-amyloid precursor protein (APP) (Boehringer Mannheim; Indianapolis, Ind.). 22C11 has been shown to induce apoptosis of primary rat cortical neurons [Rohn et al., J Neurochem (2000) 74:2331-2342; hereby incorporated by reference in its entirety].

The assay was set up essentially as described by Rohn et al. [Neurochem (2000) 74:2331-2342]. Briefly, the primary cultures of mouse cortical neurons were established from E17 embryos. The gestational pups were humanely decapitated, and the brain was harvested into Hanks Buffered Salt Solution (HBSS) buffer. The cortices were taken and processed with trypsin (0.05% in HBSS), after which the cells were mechanically dissociated using a 21 g needle. The cell suspension was then passed through a 70 μM filter, and the recovered cells plated on poly-D-lysine-treated 12-well plates. After five days of culture, the cells were used for assay. A photograph of the cells after five days of culture is presented in FIG. 11A. FIG. 11A also shows that, as expected for cortical neurons, the cells stained positively for neurofilament.

For the assay, four experimental groups were set up. To the "No Treatment" group was added neither Humanin, Compound 1 ("Cmpd1"), nor mAb 22C11. In the "22C11" group, cells were cultured in the presence of mAb 22C11 alone. In the "Humanin" and "Cmpd1" groups, the cells were cultured with Humanin or Cmpd1, respectively, beginning 1 h prior to the addition of mAb 22C11. The assay was allowed to proceed overnight (~18 h), after which cell viability was determined by LDH assay as described in Example 25.

Inspection of FIG. 11B indicates that Humanin and Compound 1 protected primary mouse cortical neurons from cell death induced by anti-APP mAb 22C11.

Example 27

Protection Against Aβ-Induced Cell Death of Differentiated SH-SY5Y Cells

The capacity of Humanin or Compound 1 to inhibit the Aβ-induced cell death of differentiated SH-SY5Y cells was determined. SH-SY5Y is a human neuroblastoma cell line. Differentiation of SH-SY5Y into neuronal-like cells was carried out by treatment with retinoic acid (10 μM) for five days followed by treatment with BDNF (10 ng/ml) for two days. Aβ (AB1-42) was purchased from Biosource International (Camarillo, Calif.; catalog no. 03-111).

Differentiated SH-SY5Y cells were cultured overnight (~18 h) either alone ("No Treatment"), in the presence of only AB1-42, in the presence of AB1-42 and Humanin, or in the presence of AB1-42 and Compound 1. The assay was carried out in serum-free medium. AB1-42 was used at 80 μg/ml. Humanin was used at 1 μM. Compound 1 was used at either 20 μM, 5 μM or 1 μM. Humanin and Compound 1 were added to culture beginning 1 h prior to the addition of AB1-42.

Cell survival was determined by Trypan Blue staining.

Inspection of FIG. 12 indicates that Humanin and Compound 1 protected differentiated SH-SY5Y cells from Aβ-induced cell death.

Example 28

Protection of Differentiated SH-SY5Y Cells and Primary Mouse Cortical Neurons from Hypoxia/Reoxygenation-Induced Cell Death The capacity of Humanin or Compound 1 to inhibit hypoxia/reoxygenation-induced cell death of differentiated SH-SY5Y cells and primary mouse cortical neurons is determined using an in vitro model. SH-SY5Y human neuroblastoma cells are differentiated as described in Example 24. Primary mouse cortical neurons are isolated as described in Example 26.

An outline of the hypoxia/reoxygenation in vitro model is presented in FIG. 13. Differentiated SH-SY5Y cells or primary mouse cortical neurons are cultured for 24-48 h in serum-free medium prior to hypoxia treatment. Hypoxia is achieved using an airtight chamber infused with 95% $N_2$ and 5% $CO_2$. Hypoxia is allowed to proceed for about 4 to about 8 h. After hypoxia treatment, cells are removed from the chamber to ambient air for a period of 24-48 hr, after which cell viability is determined either by LDH assay or DNA fragmentation. LDH assay is carried out as described in Example 25. DNA fragmentation of genomic DNA, isolated using PUREGENE® DNA isolation kit (Gentra Systems, Inc.; Minneapolis, Minn.), is detected by staining with ethidium bromide under ultraviolet light.

SH-SY5Y cells or primary mouse cortical neurons are cultured either alone or in the presence of Humanin or Compound 1. Humanin or Compound 1 is added either about 1-2 hours prior to the onset of hypoxia or immediately after the termination of hypoxia. Humanin or Compound 1 is used at about 0.5 μM to about 20 μM. By way of illustration and not limitation, Humanin or Compound 1 is used at 1 μM, 2 μM, 5 μM, 10 μM or 20 μM. In some embodiments, a compound which is an FPRL2 ligand other than Humanin or Compound 1 is assayed for the capacity to protect differentiated SH-SY5Y cells or primary mouse cortical neurons from hypoxia/reoxygenation-induced cell death.

Example 29

Upregulation of FPRL2 Expression in Alzheimer's Disease Brain Relative to that in Non-Alzheimer's Disease Brain The expression of FPRL2 in Alzheimer's disease brain relative to that in non-Alzheimer's disease brain was determined by immunohistochemistry. The human brain tissues used in this study were obtained with appropriate consent. Fresh brain tissues from the hippocampus region of a 58 year old non-Alzheimer's disease male individual ("Normal") and from the hippocampus region of a 65 year old Alzheimer's disease male patient ("AD") were obtained. The brain tissues were fixed in formalin and paraffin embedded. The paraffin embedded material was used to prepare 4 μM sections.

FPRL2 expression was interrogated using rabbit polyclonal antiserum raised against a peptide from the C-terminus of FPRL2. Specificity of staining was confirmed by blocking with the peptide used the generate the antibody.

The 4 μM paraffin sections were stained with a 1:100 dilution of the anti-FPRL2 antiserum. The slides were washed three times with phosphate buffered saline (PBS) and incubated with horseradish peroxidase (HRP)-conjugated goat anti-rabbit antibody (Dako; CA) for 30 min at room temperature. The slides were then washed three times and subjected to the color substrate diaminobenzidine (DAB) for 2 min. The color reaction was terminated with a water wash. The tissue sections were then counterstained with methyl green and covered with coverslip.

Inspection of FIG. 14 indicates that expression of FPRL2 in the Alzheimer's disease brain sample is up-regulated relative to that in the non-Alzheimer's disease brain sample. Expression of FPRL2 by the large pyramidal neurons of the Alzheimer's disease brain sample is up-regulated relative to that by the large pyramidal neurons of the non-Alzheimer's disease brain sample.

What is claimed is:

1. A method comprising:
   (a) contacting a candidate compound with a G protein-coupled receptor (GPCR) comprising an amino acid sequence having at least 90% identity to SEQ ID NO:2, wherein said GPCR is present on a cell or isolated membrane thereof;
   (b) determining the ability of the compound to inhibit or stimulate the GPCR; and
   (c) determining if said compound modulates neuronal cell death.

2. The method of claim 1, wherein said determining element (c) comprises contacting said compound with a neuron and determining if said compound modulates serum deprivation-induced neuronal cell death, Aβ-induced neuronal cell death or hypoxia/reoxygenation-induced neuronal cell death.

3. The method of claim 1, wherein element (c) comprises administering said compound to a mammal.

4. The method of claim 3, wherein element (c) comprises assaying said mammal for an effect on learning or memory.

5. The method of claim 3, wherein element (c) comprises assaying said compound for a neuroprotective activity.

6. The method of claim 3, wherein said mammal has a neuronal disorder.

7. The method of claim 1, wherein said determining element (b) comprises measuring a second messenger.

8. The method of claim 1, wherein said determining element (b) comprises measuring expression of a reporter.

9. The method of claim 1, wherein said GPCR comprises an amino acid sequence having at least 95% identity to SEQ ID NO:2.

10. The method of claim 1, wherein said GPCR is recombinant.

11. The method of claim 1, wherein said GPCR binds Humanin.

12. The method of claim 1, further comprising admixing said compound with a pharmaceutically acceptable carrier to produce a pharmaceutical composition.

13. The method of claim 12, wherein said method further comprises administering said pharmaceutical composition to a mammal having a neuronal disorder.

14. A method comprising:
   (a) contacting a compound with a G protein-coupled receptor comprising an amino acid sequence having at least 90% identity to SEQ ID NO:2, wherein said G protein-coupled receptor is present on a cell or isolated membrane thereof;
   (b) determining the ability of the compound to bind to said G protein-coupled receptor; and
   (c) determining if said compound modulates neuronal cell death.

15. A method comprising:
   (a) contacting a candidate compound with a G protein-coupled receptor (GPCR) comprising an amino acid sequence having at least 90% identical to SEQ ID NO:2, wherein said GPCR is present on a cell or isolated membrane thereof;
   (b) determining the ability of the compound to inhibit or stimulate the GPCR; and
   (c) determining if said compound modulates muscle cell death.

* * * * *

SEQUENCE LISTING

```
<160> NUMBER OF SEQ ID NOS: 16

<210> SEQ ID NO 1
<211> LENGTH: 1062
<212> TYPE: DNA
<213> ORGANISM: Human

<400> SEQUENCE: 1
atggaaacca acttctccat tcctctgaat gaaactgagg aggtgctccc tgagcctgct      60
ggccacaccg ttctgtggat cttctcattg ctagtccacg gagtcacctt tgtcttcggg     120
gtcctgggca atgggcttgt gatctgggtg gctggattcc ggatgacacg cacagtcaac     180
accatctgtt acctgaacct ggccctagct gacttctctt tcagtgccat cctaccattc     240
cgaatggtct cagtcgccat gagagaaaaa tggccttttg gctcattcct atgtaagtta     300
gttcatgtta tgatagacat caacctgttt gtcagtgtct acctgatcac catcattgct     360
ctggaccgct gtatttgtgt cctgcatcca gcctgggccc agaaccatcg caccatgagt     420
ctggccaaga gggtgatgac gggactctgg attttcacca tagtccttac cttaccaaat     480
ttcatcttct ggactacaat aagtactacg aatgggaca catactgtat tttcaacttt     540
gcattctggg gtgacactgc tgtagagagg ttgaacgtgt tcattaccat ggccaaggtc     600
tttctgatcc tccacttcat tattggcttc agcgtgccta tgtccatcat cacagtctgc     660
tatgggatca tcgctgccaa aattcacaga aaccacatga ttaaatccag ccgtccctta     720
cgtgtcttcg ctgctgtggt ggcttctttc ttcatctgtt ggttcctta tgaactaatt      780 ggcattctaa tggcagtctg gctcaaagag atgttgttaa atgcaaata caaaatcatt      840 cttgtcctga ttaacccaac aagctccttg gccttttta acagctgcct caacccaatt      900
ctctacgtct ttatgggtcg taacttccaa gaaagactga ttcgctcttt gcccactagt     960
ttggagaggg ccctgactga ggtccctgac tcagcccaga ccagcaacac agacaccact    1020
tctgcttcac ctcctgagga gacggagtta caagcaatgt ga                        1062

<210> SEQ ID NO 2
<211> LENGTH: 353
<212> TYPE: PRT
```

```
<213> ORGANISM: Human
<220> FEATURE:
<221> NAME/KEY: VARIANT
<222> LOCATION: 94
<223> OTHER INFORMATION: Xaa at position 94 is Gly or Ala
<220> FEATURE:
<221> NAME/KEY: VARIANT
<222> LOCATION: 211
<223> OTHER INFORMATION: Xaa at position 211 is Ser or Thr
<220> FEATURE:
<221> NAME/KEY: VARIANT
<222> LOCATION: 338
<223> OTHER INFORMATION: Xaa at position 338 is Asp or His

<400> SEQUENCE: 2
```

Met Glu Thr Asn Phe Ser Ile Pro Leu Asn Glu Thr Glu Glu Val Leu
1               5                   10                  15

Pro Glu Pro Ala Gly His Thr Val Leu Trp Ile Phe Ser Leu Leu Val
            20                  25                  30

His Gly Val Thr Phe Val Phe Gly Val Leu Gly Asn Gly Leu Val Ile
        35                  40                  45

Trp Val Ala Gly Phe Arg Met Thr Arg Thr Val Asn Thr Ile Cys Tyr
50                  55                  60

Leu Asn Leu Ala Leu Ala Asp Phe Ser Phe Ser Ala Ile Leu Pro Phe
65                  70                  75                  80

Arg Met Val Ser Val Ala Met Arg Glu Lys Trp Pro Phe Xaa Ser Phe
                85                  90                  95

Leu Cys Lys Leu Val His Val Met Ile Asp Ile Asn Leu Phe Val Ser
            100                 105                 110

Val Tyr Leu Ile Thr Ile Ile Ala Leu Asp Arg Cys Ile Cys Val Leu
        115                 120                 125

His Pro Ala Trp Ala Gln Asn His Arg Thr Met Ser Leu Ala Lys Arg
130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
            180                 185                 190

Val Phe Ile Thr Met Ala Lys Val Phe Leu Ile Leu His Phe Ile Ile
        195                 200                 205

Gly Phe Xaa Val Pro Met Ser Ile Ile Thr Val Cys Tyr Gly Ile Ile
    210                 215                 220

Ala Ala Lys Ile His Arg Asn His Met Ile Lys Ser Ser Arg Pro Leu
225                 230                 235                 240

Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
            260                 265                 270

Leu Asn Gly Lys Tyr Lys Ile Ile Leu Val Leu Ile Asn Pro Thr Ser
        275                 280                 285

Ser Leu Ala Phe Phe Asn Ser Cys Leu Asn Pro Ile Leu Tyr Val Phe
290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

```
Thr Xaa Thr Thr Ser Ala Ser Pro Pro Glu Glu Thr Glu Leu Gln Ala
        340                 345                 350
Met

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
aaagaattca ggtgtgggaa gatggaaacc                                    30

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 4
aaaggatccc cgacctcaca ttgcttgta                                     29

<210> SEQ ID NO 5
<211> LENGTH: 1242
<212> TYPE: DNA
<213> ORGANISM: Artificial Sequence
<220> FEATURE:
<223> OTHER INFORMATION: Polynucleotide encoding epitope-tagged human
      FPRL2 fusion protein

<400> SEQUENCE: 5
atgtacccat acgacgtccc agactacgct ggaagcttca tggaaaccaa cttctccatt     60
cctctgaatg aaactgagga ggtgctccct gagcctgctg ccacaccgt tctgtggatc     120 ttctcattgc tagtccacgg agtcaccttt gtcttcgggg tcctgggcaa tgggcttgtg    180
atctgggtgg ctggattccg gatgacacgc acagtcaaca ccatctgtta cctgaacctg    240
gccctagctg acttctcttt cagtgccatc ctaccattcc gaatggtctc agtcgccatg    300
agagaaaaat ggccttttgg ctcattccta tgtaagttag ttcatgttat gatagacatc    360
aacctgtttg tcagtgtcta cctgatcacc atcattgctc tggaccgctg tatttgtgtc    420
ctgcatccag cctgggccca gaaccatcgc accatgagtc tggccaagag ggtgatgacg    480
ggactctgga ttttcaccat agtccttacc ttaccaaatt tcatcttctg gactacaata    540
agtactacga tggggacac atactgtatt ttcaactttg cattctgggg tgacactgct    600
gtagagaggt tgaacgtgtt cattaccatg gccaaggtct ttctgatcct ccacttcatt    660
attggcttca gcgtgcctat gtccatcatc acagtctgct atgggatcat cgctgccaaa    720
attcacagaa accacatgat taaatccagc cgtcccttac gtgtcttcgc tgctgtggtg    780
gcttctttct tcatctgttg gttccccttat gaactaattg cattctaat ggcagtctgg    840 ctcaaagaga tgttgttaaa tgcaaatac aaaatcattc ttgtcctgat aacccccaaca   900 agctccttgg ccttttttaa cagctgcctc aacccaatt ctacgtctt tatgggtcgt     960 aacttccaag aaagactgat tcgctctttg cccactagtt tggagaggggc cctgactgag   1020 gtccctgact cagcccagac cagcaacaca gacaccactt ctgcttcacc tcctgaggag   1080
acggagttac aagcaatggg atccaagggc aattctgcag atatccagca cagtggcggc    1140
cgctcgagtc tagagggccc gcggttcgaa ggtaagccta tccctaaccc tctcctcggt    1200
```
ctcgattcta cgcgtaccgg tcatcatcac catcaccatt ga         1242

<210> SEQ ID NO 6
<211> LENGTH: 413
<212> TYPE: PRT
<213> ORGANISM: Artificial Sequence
<220> FEATURE:
<223> OTHER INFORMATION: Epitope-tagged human FPRL2 fusion protein

<400> SEQUENCE: 6

```
Met Tyr Pro Tyr Asp Val Pro Asp Tyr Ala Gly Ser Phe Met Glu Thr
1               5                   10                  15

Asn Phe Ser Ile Pro Leu Asn Glu Thr Glu Glu Val Leu Pro Glu Pro
            20                  25                  30

Ala Gly His Thr Val Leu Trp Ile Phe Ser Leu Leu Val His Gly Val
        35                  40                  45

Thr Phe Val Phe Gly Val Leu Gly Asn Gly Leu Val Ile Trp Val Ala
    50                  55                  60

Gly Phe Arg Met Thr Arg Thr Val Asn Thr Ile Cys Tyr Leu Asn Leu
65                  70                  75                  80

Ala Leu Ala Asp Phe Ser Phe Ser Ala Ile Leu Pro Phe Arg Met Val
                85                  90                  95

Ser Val Ala Met Arg Glu Lys Trp Pro Phe Gly Ser Phe Leu Cys Lys
            100                 105                 110

Leu Val His Val Met Ile Asp Ile Asn Leu Phe Val Ser Val Tyr Leu
        115                 120                 125

Ile Thr Ile Ile Ala Leu Asp Arg Cys Ile Cys Val Leu His Pro Ala
    130                 135                 140

Trp Ala Gln Asn His Arg Thr Met Ser Leu Ala Lys Arg Val Met Thr
145                 150                 155                 160

Gly Leu Trp Ile Phe Thr Ile Val Leu Thr Leu Pro Asn Phe Ile Phe
                165                 170                 175

Trp Thr Thr Ile Ser Thr Thr Asn Gly Asp Thr Tyr Cys Ile Phe Asn
            180                 185                 190

Phe Ala Phe Trp Gly Asp Thr Ala Val Glu Arg Leu Asn Val Phe Ile
        195                 200                 205

Thr Met Ala Lys Val Phe Leu Ile Leu His Phe Ile Ile Gly Phe Ser
    210                 215                 220

Val Pro Met Ser Ile Ile Thr Val Cys Tyr Gly Ile Ile Ala Ala Lys
225                 230                 235                 240

Ile His Arg Asn His Met Ile Lys Ser Ser Arg Pro Leu Arg Val Phe
                245                 250                 255

Ala Ala Val Val Ala Ser Phe Phe Ile Cys Trp Phe Pro Tyr Glu Leu
            260                 265                 270

Ile Gly Ile Leu Met Ala Val Trp Leu Lys Glu Met Leu Leu Asn Gly
        275                 280                 285

Lys Tyr Lys Ile Ile Leu Val Leu Ile Asn Pro Thr Ser Ser Leu Ala
    290                 295                 300

Phe Phe Asn Ser Cys Leu Asn Pro Ile Leu Tyr Val Phe Met Gly Arg
305                 310                 315                 320

Asn Phe Gln Glu Arg Leu Ile Arg Ser Leu Pro Thr Ser Leu Glu Arg
                325                 330                 335

Ala Leu Thr Glu Val Pro Asp Ser Ala Gln Thr Ser Asn Thr Asp Thr
            340                 345                 350
```

```
Thr Ser Ala Ser Pro Glu Glu Thr Glu Leu Gln Ala Met Gly Ser
        355                 360                 365

Lys Gly Asn Ser Ala Asp Ile Gln His Ser Gly Arg Ser Ser Leu
    370                 375                 380

Glu Gly Pro Arg Phe Glu Gly Lys Pro Ile Pro Asn Pro Leu Leu Gly
385                 390                 395                 400

Leu Asp Ser Thr Arg Thr Gly His His His His His His
                405                 410

<210> SEQ ID NO 7
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 7
cccaagcttc atggaaacca acttctccat tcctc                          35

<210> SEQ ID NO 8
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 8
cccggatccc attgcttgta actccgtctc ctc                            33

<210> SEQ ID NO 9
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 9
tccagccgtc ccaaacgtgt cttcgctgc                                 29

<210> SEQ ID NO 10
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 10
ctccttcggt cctcctatcg ttgtcagaag t                              31

<210> SEQ ID NO 11
<211> LENGTH: 1062
<212> TYPE: DNA
<213> ORGANISM: Artificial Sequence
<220> FEATURE:
<223> OTHER INFORMATION: Polynucleotide encoding mutated FPRL2

<400> SEQUENCE: 11
atggaaacca acttctccat tcctctgaat gaaactgagg aggtgctccc tgagcctgct      60
ggccacaccg ttctgtggat cttctcattg ctagtccacg gagtcacctt tgtcttcggg     120
gtcctgggca atgggcttgt gatctgggtg gctggattcc ggatgacacg cacagtcaac     180
accatctgtt acctgaacct ggccctagct gacttctctt tcagtgccat cctaccattc     240
cgaatggtct cagtcgccat gagagaaaaa tggccttttg gctcattcct atgtaagtta     300
```

```
gttcatgtta tgatagacat caacctgttt gtcagtgtct acctgatcac catcattgct    360
ctggaccgct gtatttgtgt cctgcatcca gcctgggccc agaaccatcg caccatgagt    420
ctggccaaga gggtgatgac gggactctgg attttcacca tagtccttac cttaccaaat    480
ttcatcttct ggactacaat aagtactacg aatggggaca catactgtat tttcaacttt    540
gcattctggg gtgacactgc tgtagagagg ttgaacgtgt tcattaccat ggccaaggtc    600
tttctgatcc tccacttcat tattggcttc agcgtgccta tgtccatcat cacagtctgc    660
tatgggatca tcgctgccaa aattcacaga aaccacatga ttaaatccag ccgtcccaaa    720
cgtgtcttcg ctgctgtggt ggcttctttc ttcatctgtt ggttccctta tgaactaatt    780
ggcattctaa tggcagtctg gctcaaagag atgttgttaa atggcaaata caaaatcatt    840
cttgtcctga ttaacccaac aagctccttg gcctttttta acagctgcct caacccaatt    900
ctctacgtct ttatgggtcg taacttccaa gaaagactga ttcgctcttt gcccactagt    960
ttggagaggg ccctgactga ggtccctgac tcagcccaga ccagcaacac agacaccact   1020
tctgcttcac ctcctgagga gacggagtta caagcaatgt ga                     1062
```

<210> SEQ ID NO 12
<211> LENGTH: 353
<212> TYPE: PRT
<213> ORGANISM: Artificial Sequence
<220> FEATURE:
<223> OTHER INFORMATION: Mutated FPRL2 protein

<400> SEQUENCE: 12

```
Met Glu Thr Asn Phe Ser Ile Pro Leu Asn Glu Thr Glu Glu Val Leu
  1               5                  10                  15

Pro Glu Pro Ala Gly His Thr Val Leu Trp Ile Phe Ser Leu Leu Val
             20                  25                  30

His Gly Val Thr Phe Val Phe Gly Val Leu Gly Asn Gly Leu Val Ile
         35                  40                  45

Trp Val Ala Gly Phe Arg Met Thr Arg Thr Val Asn Thr Ile Cys Tyr
     50                  55                  60

Leu Asn Leu Ala Leu Ala Asp Phe Ser Phe Ser Ala Ile Leu Pro Phe
 65                  70                  75                  80

Arg Met Val Ser Val Ala Met Arg Glu Lys Trp Pro Phe Gly Ser Phe
                 85                  90                  95

Leu Cys Lys Leu Val His Val Met Ile Asp Ile Asn Leu Phe Val Ser
            100                 105                 110

Val Tyr Leu Ile Thr Ile Ile Ala Leu Asp Arg Cys Ile Cys Val Leu
        115                 120                 125

His Pro Ala Trp Ala Gln Asn His Arg Thr Met Ser Leu Ala Lys Arg
    130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
            180                 185                 190

Val Phe Ile Thr Met Ala Lys Val Phe Leu Ile Leu His Phe Ile Ile
        195                 200                 205

Gly Phe Ser Val Pro Met Ser Ile Ile Thr Val Cys Tyr Gly Ile Ile
    210                 215                 220
```

```
Ala Ala Lys Ile His Arg Asn His Met Ile Lys Ser Ser Arg Pro Lys
225                 230                 235                 240

Arg Val Phe Ala Ala Val Val Ala Ser Phe Ile Cys Trp Phe Pro
            245                 250                 255

Tyr Glu Leu Ile Gly Ile Leu Met Ala Val Trp Leu Lys Glu Met Leu
                260                 265                 270

Leu Asn Gly Lys Tyr Lys Ile Ile Leu Val Leu Ile Asn Pro Thr Ser
            275                 280                 285

Ser Leu Ala Phe Phe Asn Ser Cys Leu Asn Pro Ile Leu Tyr Val Phe
290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr Asp Thr Thr Ser Ala Ser Pro Pro Glu Glu Thr Glu Leu Gln Ala
                340                 345                 350

Met

<210> SEQ ID NO 13
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 13
gatcaagctt ccatggcgtg ctgcctgagc gaggag                             36

<210> SEQ ID NO 14
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 14
gatcggatcc ttagaacagg ccgcagtcct tcaggttcag ctgcaggatg gtg          53

<210> SEQ ID NO 15
<211> LENGTH: 24
<212> TYPE: PRT
<213> ORGANISM: Homo sapiens

<400> SEQUENCE: 15

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Trp Lys Tyr Met Val Met
1               5
```